(12) United States Patent
Bowles et al.

(10) Patent No.: US 9,629,689 B2
(45) Date of Patent: Apr. 25, 2017

(54) ATTACHMENT APPARATUS FOR REMOTE ACCESS TOOLS

(71) Applicant: FlexDex, Inc., Brighton, MI (US)

(72) Inventors: Gregory Brian Bowles, Fenton, MI (US); James Duncan Geiger, Toledo, OH (US); James Michael Licht, Howell, MI (US); Shorya Awtar, Ann Arbor, MI (US); Zachary Zimmerman, Waterford, MI (US); Deepak Sharma, Ann Arbor, MI (US)

(73) Assignee: FlexDex, Inc., Brighton, MI (US)

( * ) Notice: Subject to any disclaimer, the term of this patent is extended or adjusted under 35 U.S.C. 154(b) by 0 days.

(21) Appl. No.: 15/130,915

(22) Filed: Apr. 15, 2016

(65) Prior Publication Data

US 2016/0303734 A1 Oct. 20, 2016

Related U.S. Application Data

(60) Provisional application No. 62/147,998, filed on Apr. 15, 2015, provisional application No. 62/236,805, filed on Oct. 2, 2015.

(51) Int. Cl.
*A61B 34/00* (2016.01)
*F16M 13/04* (2006.01)
(Continued)

(52) U.S. Cl.
CPC .......... *A61B 34/71* (2016.02); *A61B 17/2909* (2013.01); *A61B 90/53* (2016.02);
(Continued)

(58) Field of Classification Search
CPC .... B25J 1/02; B25J 13/02; B25J 13/00; A61B 34/71; A61B 34/70; A61B 34/75;
(Continued)

(56) References Cited

U.S. PATENT DOCUMENTS

| | | |
|---|---|---|
| 3,497,083 A | 2/1970 | Anderson et al. |
| 4,466,649 A | 8/1984 | Ozawa |

(Continued)

FOREIGN PATENT DOCUMENTS

| | | |
|---|---|---|
| GB | 0937587 A | 10/1964 |
| JP | 3-292879 A | 12/1991 |

(Continued)

OTHER PUBLICATIONS

Awtar et al.; U.S. Appl. No. 15/054,068 entitled "Parallel kinematic mechanisms with decoupled rotational motions," filed Feb. 25, 2016.

(Continued)

*Primary Examiner* — Katrina Stransky
(74) *Attorney, Agent, or Firm* — Shay Glenn LLP

(57) ABSTRACT

Apparatuses and methods for attaching a minimal access tool to a user's body (e.g., wrist or forearm) so that movements of the user's forearm, wrist, hand and fingers can control movements at a distal end of the minimal access tool. In particular, described herein are forearm attachment devices (which may be used with or integrated into) a minimal access tool including a cuff configured to secure to the user's forearm and a coupling joint configured to connect the cuff to the frame so that the cuff may move relative to the frame with between 1 and 4 degrees of freedom.

25 Claims, 34 Drawing Sheets

(51) Int. Cl.
*A61B 90/53* (2016.01)
*A61B 17/29* (2006.01)
*A61B 17/00* (2006.01)

(52) U.S. Cl.
CPC ... *F16M 13/04* (2013.01); *A61B 2017/00442* (2013.01); *A61B 2017/291* (2013.01)

(58) Field of Classification Search
CPC ... A61B 34/77; A61B 90/53; A61B 2034/306; A61B 2017/00323; A61B 2017/00424; A61B 2017/00442; A61B 2017/00464; A61B 2017/2917; A61B 2017/2929; A61B 2017/2931; A61B 2017/2937; A61B 2017/2939; A61B 2017/2944; A61B 34/37; A61B 17/2909; A61B 17/2841; F16M 13/04
USPC .......................................................... 606/130
See application file for complete search history.

(56) References Cited

U.S. PATENT DOCUMENTS

| | | | |
|---|---|---|---|
| 4,568,311 A | 2/1986 | Miyake | |
| 4,712,545 A | 12/1987 | Honkanen | |
| 4,750,475 A | 6/1988 | Yoshihashi | |
| 4,950,273 A | 8/1990 | Briggs | |
| 5,021,969 A | 6/1991 | Okamura et al. | |
| 5,147,357 A | 9/1992 | Rose et al. | |
| 5,209,747 A | 5/1993 | Knoepfler | |
| 5,323,570 A | 6/1994 | Kuhlman et al. | |
| 5,330,502 A | 7/1994 | Hassler et al. | |
| 5,350,391 A | 9/1994 | Iacovelli | |
| 5,368,600 A | 11/1994 | Failla et al. | |
| 5,374,277 A | 12/1994 | Hassler | |
| 5,454,827 A | 10/1995 | Aust et al. | |
| 5,456,695 A | 10/1995 | Herve Dallemagne | |
| 5,599,151 A | 2/1997 | Daum et al. | |
| 5,620,415 A | 4/1997 | Lucey et al. | |
| 5,626,608 A | 5/1997 | Cuny et al. | |
| 5,683,412 A | 11/1997 | Scarfone | |
| 5,713,505 A | 2/1998 | Huitema | |
| 5,716,352 A | 2/1998 | Viola et al. | |
| 5,735,874 A | 4/1998 | Measamer et al. | |
| 5,782,748 A | 7/1998 | Palmer et al. | |
| 5,807,376 A | 9/1998 | Viola et al. | |
| 5,817,084 A | 10/1998 | Jensen | |
| 5,820,009 A | 10/1998 | Melling et al. | |
| 5,853,412 A | 12/1998 | Mayenberger | |
| 5,860,995 A | 1/1999 | Berkelaar | |
| 5,908,436 A | 6/1999 | Cuschieri et al. | |
| 6,309,403 B1 | 10/2001 | Minor et al. | |
| 6,312,435 B1 | 11/2001 | Wallace et al. | |
| 6,330,837 B1 | 12/2001 | Charles et al. | |
| 6,714,839 B2 | 3/2004 | Salisbury et al. | |
| 6,853,879 B2 | 2/2005 | Sunaoshi | |
| 6,889,116 B2 | 5/2005 | Jinno | |
| 6,994,716 B2 | 2/2006 | Jinno et al. | |
| 7,101,363 B2 | 9/2006 | Nishizawa et al. | |
| 7,147,650 B2 | 12/2006 | Lee | |
| 7,708,756 B2 | 5/2010 | Nobis et al. | |
| 7,736,254 B2 | 6/2010 | Schena | |
| 8,029,531 B2 | 10/2011 | Lee et al. | |
| 8,465,475 B2 | 6/2013 | Isbell | |
| 8,528,440 B2 | 9/2013 | Morley et al. | |
| 8,540,748 B2 | 9/2013 | Murphy et al. | |
| 8,668,702 B2 | 3/2014 | Awtar et al. | |
| 8,992,422 B2 | 3/2015 | Spivey et al. | |
| 2001/0031983 A1 | 10/2001 | Brock et al. | |
| 2003/0036748 A1 | 2/2003 | Cooper et al. | |
| 2003/0135203 A1 | 7/2003 | Wang et al. | |
| 2003/0176880 A1 | 9/2003 | Long et al. | |
| 2003/0176948 A1 | 9/2003 | Green | |
| 2004/0253079 A1 | 12/2004 | Sanchez | |
| 2005/0004431 A1 | 1/2005 | Kogasaka et al. | |
| 2005/0038469 A1 | 2/2005 | Lang | |
| 2005/0107667 A1 | 5/2005 | Danitz et al. | |
| 2006/0259073 A1 | 11/2006 | Miyamoto et al. | |
| 2006/0282063 A1 | 12/2006 | Gotani | |
| 2007/0021738 A1 | 1/2007 | Hasser et al. | |
| 2007/0078565 A1 | 4/2007 | Ghodoussi et al. | |
| 2008/0065098 A1 | 3/2008 | Larkin | |
| 2010/0004606 A1 | 1/2010 | Hansen et al. | |
| 2010/0030018 A1 | 2/2010 | Fortier et al. | |
| 2010/0056863 A1 | 3/2010 | Dejima et al. | |
| 2011/0152881 A1 | 6/2011 | Conner et al. | |
| 2012/0095298 A1 | 4/2012 | Stefanchik et al. | |
| 2013/0012958 A1 | 1/2013 | Marczyk et al. | |
| 2013/0172860 A1 | 7/2013 | Szewczyk et al. | |
| 2013/0239734 A1 | 9/2013 | Hinman | |
| 2014/0135805 A1 | 5/2014 | Windgassen et al. | |
| 2014/0142595 A1 | 5/2014 | Awtar et al. | |
| 2015/0164601 A1* | 6/2015 | Sholev ............... | A61B 17/2909 606/1 |
| 2016/0135830 A1 | 5/2016 | Volkmer et al. | |
| 2016/0291383 A1 | 10/2016 | Han et al. | |

FOREIGN PATENT DOCUMENTS

| | | | |
|---|---|---|---|
| JP | 8-84702 A | 4/1996 | |
| JP | 2002102248 A | 4/2002 | |
| JP | 2003061969 A | 3/2003 | |
| JP | 2007130485 A | 5/2007 | |
| WO | WO2007/146894 A2 | 12/2007 | |
| WO | WO2008/020964 A2 | 2/2008 | |
| WO | WO 2014033717 A1 * | 3/2014 | ......... A61B 17/2909 |
| WO | WO2015/125140 A1 | 8/2015 | |
| WO | WO2016/161449 A1 | 10/2016 | |

OTHER PUBLICATIONS

Awtar et al.; A minimally invasive surgical tool with enhanced dexterity and intuitive actuation; J. Med. Devices; 4(3); 8 pages; Sep. 10, 2010 (Author's Draft; 12 pages).

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Sharma et al.; U.S. Appl. No. 15/284,345 entitled "Handle mechanism providing unlimited roll," filed Oct. 3, 2016.

Licht et al.; U.S. Appl. No. 15/286,489 entitled "Medical devices having smoothly articulating multi-cluster joints," filed Oct. 5, 2016.

Zimmerman et al.; U.S. Appl. No. 15/286,547 entitled "End-effector jaw closure transmission system for remote access tools," filed Oct. 5, 2016.

* cited by examiner

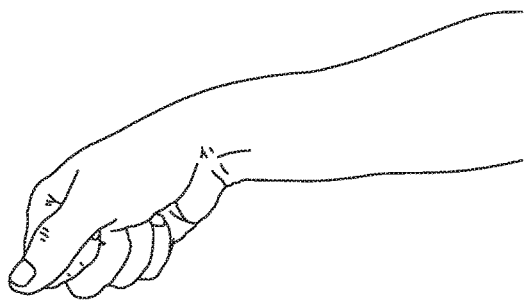
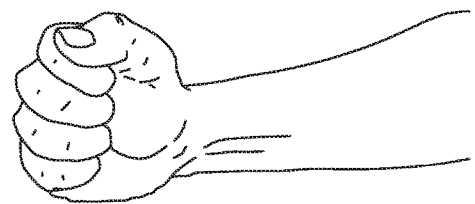
FIG. 7A  FIG. 7B
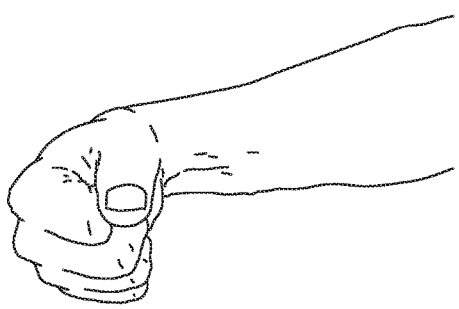
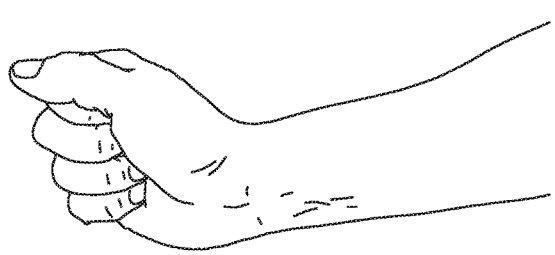
FIG. 8A  FIG. 8B
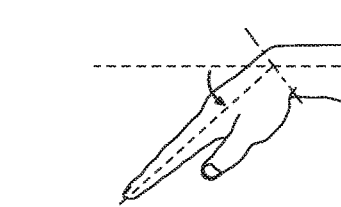
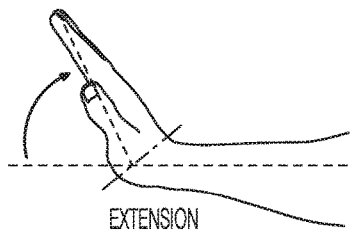
FLEXION  EXTENSION
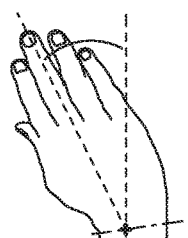
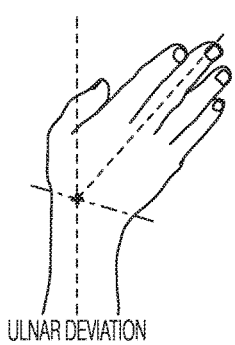
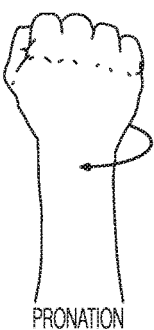
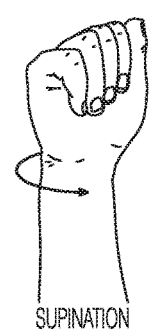
RADIAL DEVIATION  ULNAR DEVIATION  PRONATION  SUPINATION
FIG. 9

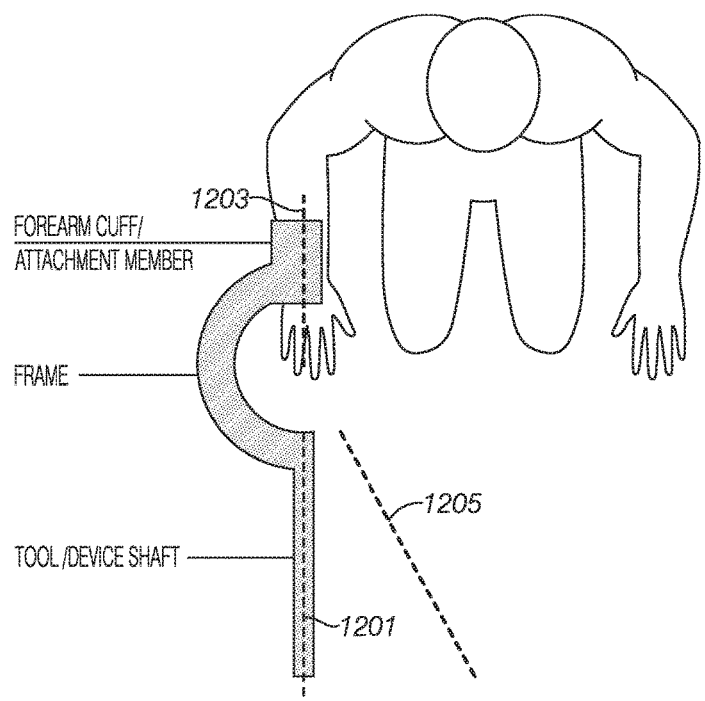
FIG. 12
  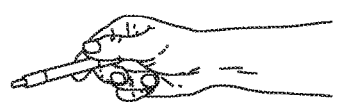
FIG. 13A  FIG. 13B  FIG. 13C
 
FIG. 14A  FIG. 14B

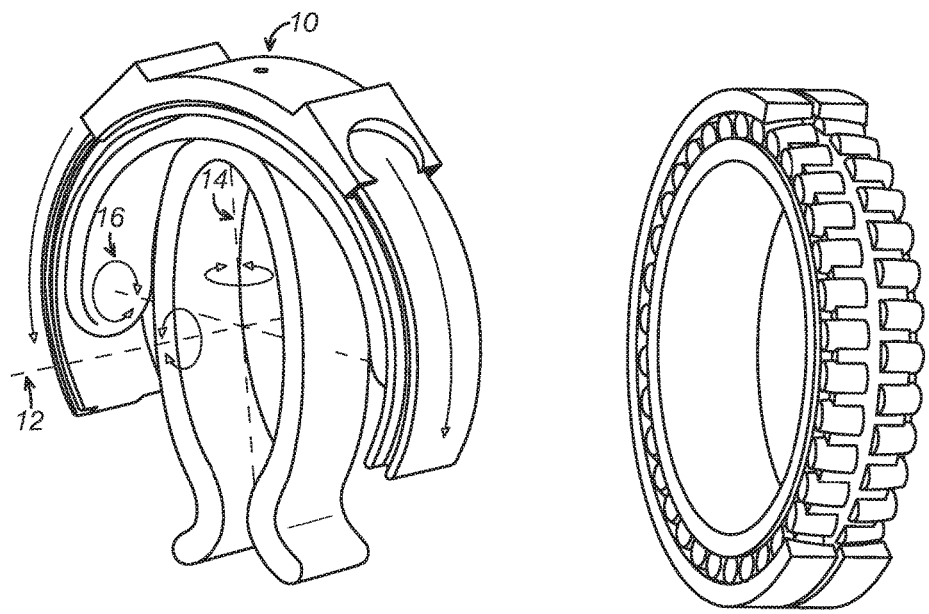
FIG. 19
FIG. 20
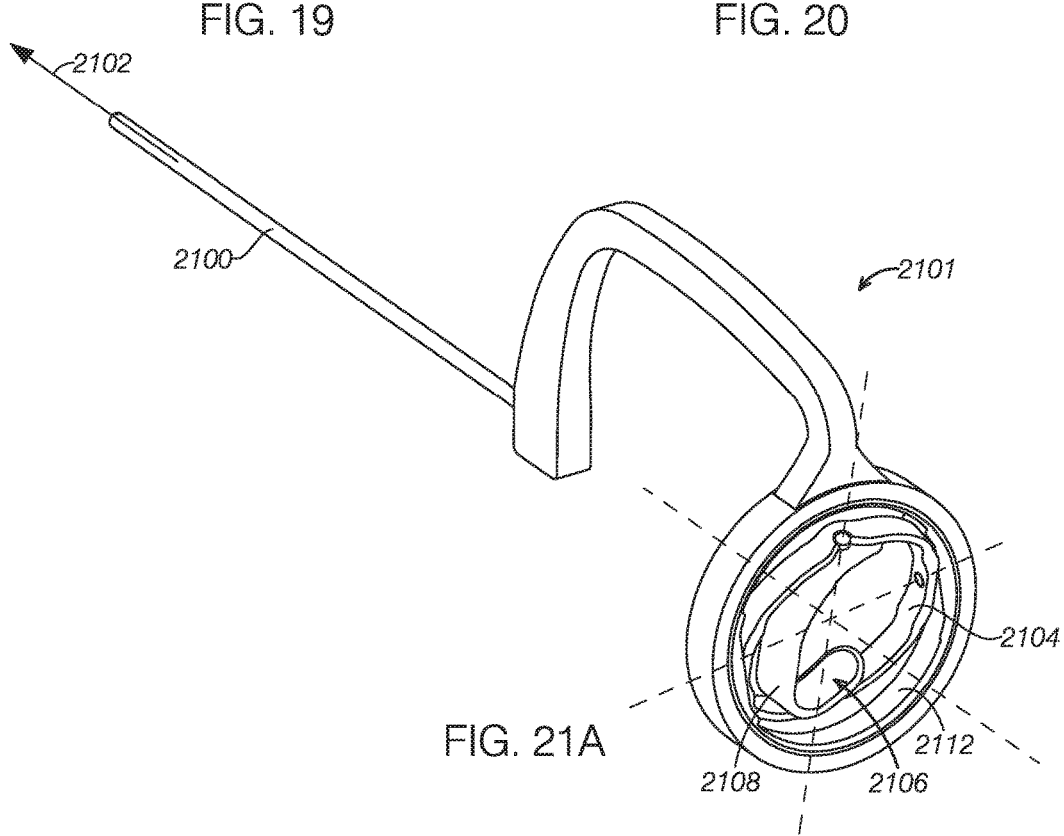
FIG. 21A

AXIAL DoF

HORIZONTAL DoF

VERTICAL DoF

ROLL DoF

PITCH DoF

YAW DoF

ATTACHMENT APPARATUS FOR REMOTE ACCESS TOOLS

CROSS REFERENCE TO RELATED APPLICATIONS

This application claims priority to U.S. Provisional Patent Application No. 62/147,998, filed Apr. 15, 2015 (and titled "FOREARM ATTACHMENT APPARATUS FOR REMOTE ACCESS TOOLS"), and U.S. Provisional Patent Application No. 62/236,805, filed Oct. 2, 2015 (titled "FOREARM ATTACHMENT APPARATUS FOR REMOTE ACCESS TOOLS") each of which is herein incorporated by reference in its entirety.

This application may be related to U.S. patent application Ser. No. 15/054,068, filed on Feb. 25, 2016, and titled "PARALLEL KINEMATIC MECHANISMS WITH DECOUPLED ROTATIONAL MOTIONS" which claims priority as a CIP to U.S. patent application Ser. No. 14/166,503, filed on Jan. 28, 2014, and titled "MINIMAL ACCESS TOOL," Publication No. US-2014-0142595-A1, which is a continuation of U.S. patent application Ser. No. 12/937,523, filed on Apr. 13, 2009, now U.S. Pat. No. 8,668,702, which claimed priority to U.S. provisional patent application No. 61/044,168, filed on Apr. 11, 2008. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Apparatuses and methods for attaching a minimal access tool to a user's arm (e.g., wrist and/or forearm) so that the tool shaft axis passes through the center of user's wrist and movements of the user's hand and fingers can separately control movements at a distal end of a minimal access tool.

BACKGROUND

A number of minimal access tools that may be controlled by a user's hand are known, such as, for example, U.S. Pat. No. 8,668,702 and U.S. patent application Ser. No. 14/166,503. These devices may include a frame, an input joint that provides two orthogonal rotations between a handle and the frame, a tool shaft that is connected to the frame, an output joint that provides two orthogonal rotations between the tool shaft and an end-effector, and a means (such as a transmission system) to transmit the two orthogonal rotations of the input joint to the output joint. These devices are exceptionally useful, and may allow highly dexterous control (e.g., articulation) of tool connected to the output joint at the end of the elongate shaft. In general, devices such as those described in U.S. Pat. No. 8,668,702 typically secure the frame directly to the arm of the user, and more generally the frame is typically attached to the forearm of the user. An example of an apparatus as taught in U.S. Pat. No. 8,668,702 is shown in FIGS. 1-3.

In these examples, the frame may be an extended structure that is rigidly connected to the tool shaft on one end and a forearm attachment member on the other end. The forearm attachment member interfaces with the forearm using a variety of means including Velcro, straps, etc. The forearm attachment may connect comfortably yet securely, i.e. to constrain, and therefore transmit, all degrees of freedom (DoF) or motions between the forearm and the forearm attachment member. Some relative motion may still be allowed to ensure comfort. As used herein, "forearm" may refer to the distal end of the arm, e.g., distal to the elbow and just before the wrist joint, as illustrated in FIG. 4.

This kind of arrangement may decouple two rotational DoF (pitch and yaw) associated with the wrist and one open/close DoF associated with thumb/fingers from the four DoF available at the forearm: three translations and 1 roll rotation. FIG. 5 illustrates the three orthogonal translations at the forearm. FIGS. 6A-6C show the roll rotation of a forearm (pronation/supination). The remaining two rotations associated with the wrist joint are also shown in FIGS. 7A-7B and 8A-8B. FIGS. 7A and 7B illustrate pitch rotation of the wrist joint (e.g., radial and ulnar deviation). FIGS. 8A and 8B illustrate yaw rotation of the wrist joint (flexion/extension). FIG. 9 shows additional illustrations of the rotational motions associated with the forearm and the wrist joint.

In these examples, note that the DoF are cumulative; i.e., there are four DoF available at the forearm; the wrist-joint provides another two; therefore, at the hand (palm), there are 6 DoF. There are additional DoF associated with the fingers/thumb. These include open/close motion, which was discussed in U.S. Pat. No. 8,668,702. These may also include other motions such as twirling and pecking, which will be described further below.

The forearm attachment described in U.S. Pat. No. 8,668,702 transmits 4 DoF at the forearm (three translations) and one roll rotation to the instrument shaft distal end, independent of the wrist rotations and finger/thumb closure motion. This may be accomplished because the forearm is attached to the frame via the forearm attachment member, and therefore the four motions at the forearm translate to the frame and then to the shaft and to the distal end of the shaft. Separately, an input joint, which may be configured as a virtual center (VC) mechanism, and may be employed to capture the two rotations of the wrist joint of the user. These two are then transmitted via a mechanical transmission comprising cables that are routed via the common ground (i.e. the frame and the tool-shaft) of the input joint and output joint (end-effector articulating join). As described in U.S. Pat. No. 8,668,702, the transmission system may be any general transmission system and not simply one that is based on cables.

Such schemes may allow for a one-to-one (1:1) motion mapping from the user's (e.g. a surgeon's) motion input to the corresponding output motions of a remote end-effector. FIG. 10 illustrates a mapping of the user input motions to the device output motions in this type of system. However, by rigidly attaching the frame to the forearm of the user, making the frame a rigid extension of the forearm, the axis of the instrument (specifically the axis of the shaft) becomes rigidly fixed (or not adjustable) with respect to the axis of the forearm. This may prove to be uncomfortable for the user in a situation when the tool shaft has to point in a certain direction and may require discrete re-adjustment with respect to the forearm during use. A rigid or non-adjustable alignment of the instrument axis with the forearm may not be ergonomically conducive for the user's forearm and shoulder. In one exemplary view in FIG. 11 (showing a side view), the two nearly horizontal lines 1101 and 1103 (axis of the device and axis of the forearm) are aligned with each other because of the "rigid" or locked forearm cuff attachment. If the instrument/device (e.g. its shaft) needs to be pointed in a certain direction (shown by line 1105) as may be required by some application (e.g. a surgical procedure), then the forearm will also have to follow the same extended line, which might be uncomfortable for the user's upper arm and shoulder. To correct for this, the device must be manually adjusted (if possible) to modify the angle of the apparatus relative to the user's body. What is needed is a device that may continuously adjust the alignment of the apparatus during use. As described herein, connecting the body part to the frame of the device through one or more coupling joints permitting predetermined degrees of freedom (while constraining others) may allow continuous adjustability.

A similar limitation may arise in the other plane as seen in the top view of FIG. 12. As shown in FIG. 12, the two lines 1201, 1203 (e.g. the axis of the device and the axis of the forearm) are aligned with each other because of the rigid (or locked) forearm cuff attachment. If the instrument/device/tool (e.g. its shaft) needs to be pointed in a direction such as the one shown by line 1205, as required by some applications (e.g. surgical procedures), then the forearm will also have to follow the same extended line, which might be uncomfortable for the user.

Further, attaching the frame rigidly to the forearm may limit the ability to transmit certain motions or DoF associated with the user's fingers, particularly twirling motion and pecking motion which are illustrated in FIGS. 13A-13C and 14A-14B. For example, FIGS. 13A-13C illustrate a hand making a twirling motion with an object (e.g., pen). In this example, the forearm and wrist joint do not move while the fingers/thumb produce the twirling motion. FIGS. 14A-14B illustrate a pecking motion. When making a pecking motion, the forearm and wrist joint do not move while the fingers/thumb produce the fore and aft pecking motion. These motions of the fingers/thumb may happen with respect to the wrist joint and forearm, but when the frame (and therefore tool shaft) is rigidly attached to the forearm, these motions are not directly transmitted to frame, e.g., the tool shaft including the tool-shaft distal end. These motions may be captured and transmitted in an indirect manner, e.g., when using a transmission system that is routed through the tool frame and shaft, as described in the U.S. Pat. No. 8,668,702 patent, in which the two wrist motions and the fingers/thumb open/close motion are captured and transmitted to corresponding output motion of an end-effector at the distal end of the tool shaft. Similarly, the pecking motion of the fingers/thumb may be translated to a similar motion between the handle and the tool frame (when the user holds the handle in his hand, fingers, and thumb); this relative motion between the handle and tool frame may be captured via a transmission system (e.g. a cable or other transmission system between the frame and distal end of the tool shaft) and transmitted to a corresponding motion between the end-effector and distal end of the tool shaft. Similar transmission may be conceived for the twirling motion as well. However, when the tool frame is secured to the forearm via a forearm attachment member, the yaw and pitch rotations of the hand/wrist or the twirling and pecking motion of the fingers/thumb/hand are not directly transmitted to the tool shaft distal end. As used herein, "direct" transmission means a transmission that may be achieved by virtue of a geometric extension as opposed to via a "transmission system" that comprises multiple components that move relative to each other.

Described herein are methods and apparatuses that may address the problems and goals discussed above. In particular, described herein are wrist and/or forearm attachment devices, and/or apparatuses such as tools and systems including these forearm attachment devices, that may allow for direct transmission of additional motions such as pecking and twirling motions.

The methods and apparatuses described herein may achieve these advantages by providing a coupling between a body portion, e.g., a wrist and/or a forearm, and a frame so that the body portion may be moved through one or more degrees of freedom relative to a portion of the frame.

SUMMARY OF THE DISCLOSURE

Described herein are apparatuses, including devices, systems and tools, that provide one or more degrees of freedom (DoF) between a frame (e.g., a frame of a minimal access tool) and an attachment region of the apparatus, such as a cuff, that couples the apparatus to a body part. In particular, described herein are tools such as minimal access tools that couple to the user's wrist and/or forearm to allow the user's wrist and/or forearm to move with one or more degrees of freedom relative to the frame of the tool.

Any of the apparatuses described herein may be configured to mount to a user's body, and particularly a user's appendages, such as an arm or leg. In particular, any of these apparatuses may be configured to mount to a user's arm, such as the user's wrist and/or forearm. Specifically, the apparatuses described herein may be configured to mount to a user's body (e.g., a wrist or forearm) so that the tool may roll about a roll axis that extends through (e.g., intersects) the user's wrist, forearm, and/or upper arm. The roll axis of the tool may be an axis of the minimal access tool. For example, the minimal access tool may include a tool axis, which may correspond to a long axis (e.g., distal to proximal) of an elongate member, such as a tool shaft, extending from the rest of the frame. The tool shaft is typically straight, but may be curved or bent. The tool axis typically extends from the distal end of the tool shaft to a proximal region.

Any of the apparatuses described herein may be minimal access tools that are configured to rotate about a tool axis when mounted on a user's body (e.g., arm). Such apparatuses may enhance manipulation of the tool when operating a distal end effector at the distal end of the tool shaft. Thus, rotation at the user's arm may be transferred into roll about the tool axis, permitting roll at a distal end effector without sweeping the tool shaft. For convenience, the term apparatus may refer to a device, a system, or a tool. The terms "tool," "instrument" and "device" may be used interchangeably in this application.

For example, described herein are minimal access tools that generally include: a frame having an elongate tool shaft, the elongate tool shaft having a tool axis; a cuff that is configured to attach to a user's wrist or forearm; and a coupling joint between the cuff and the frame so that there is a roll rotational degree of freedom between the cuff and the frame about the tool axis, wherein, when the cuff is attached to the user's wrist or forearm, the tool axis passes through a center region of the user's wrist.

Although many of the body attachment assemblies described herein may permit rotation of the frame relative to the cuff about the tool axis (e.g., roll rotation), some may rotate just in pitch, yaw or pitch and yaw, and may not permit roll.

Examples of frames are described herein. A frame may generally be a rigid structure to which other structures are attached and supported. Other structures may include controls (e.g., handles, etc.), transmissions (e.g., cables, pulleys, encoders, wiring, etc.), actuators, end effectors (e.g., clamp, grasper, screwdriver, suture passer, etc.), and the like. The frame may be formed of a metal, polymeric, or other material, and may be relatively lightweight. In general, the frames described herein include an elongate tool shaft. The tool shaft, and indeed any region of the frame, may be hollow and may contain, protect, and/or support other components. The frame may be such that its shape and geometry can be adjusted and potentially locked to suit the user preference and need.

A cuff may generally refer to a holder or seat for a user's appendage. The cuff may be shaped to receive and retain an arm (e.g., wrist, forearm, upper arm, etc.) or leg (e.g., ankle, lower leg, upper leg, etc.). A cuff may be tubular or hemitubular, including C-shaped (e.g., having a C-shaped profile). A cuff may be configured to conform to the portion of the user's anatomy to which it will be attached. The cuff may include an internal seating region for holding the body part. The cuff may be rigid, soft, flexible, or elastic. A cuff may comprise a flexible band coupled to the frame. The cuff may be a separate or separable (e.g., removable) portion of the apparatus, or it may be integrated into, and form a part of, another portion of the apparatuses described herein, including the coupling joint. Examples of both separate and integral cuffs are described in greater detail herein.

A coupling joint generally refers to an element for connecting parts of machinery, forming a joint between two rigid bodies, for example, such as the frame and the cuff. As will be described in greater detail below, a coupling joint may be coupling joints that can be used to provide one or more degree of freedom of movement between the structures being coupled. For example, a coupling joint may include a gimbal member, a bearing (e.g., plain bearing, such as a sled, bushing, journal bearing, sleeve bearing, rifle bearing; rolling-element bearing, such as ball bearings and roller bearings; jewel bearings; fluid bearings; magnetic bearings; and flexure bearing), etc.

In general, in the minimal access tools in which the cuff and the frame are coupled by a coupling joint (e.g., a bearing such as a plain bearing or rolling element bearing) the coupling joint may permit rotation about the tool axis (thus the tool axis is the roll axis) and the apparatus may be configured so that the tool axis always extends through the region of the cuff where a user's arm (or other body part such as the user's wrist or forearm) will be held. Thus, even as the user's arm is held in the cuff and the apparatus is rolled around the tool shaft, the tool axis (roll axis) passes through the cuff and through a region of the user's body such as their wrist or forearm that is held within the cuff. These apparatuses are therefore configured so that the roll degree of freedom (DoF) between the attachment site for the apparatus, such as a cuff, and the frame is the specific case in which the roll axis orientation intersects the same portion of a body held within the cuff.

In any of these apparatuses, in addition to a roll degree of freedom (DoF) between the cuff and the frame, additional degrees of freedom may be included between the cuff and the frame, including additional rotational DoF such as pitch and yaw. For example, a minimal access tool as described herein may include: a frame having an elongate tool shaft extending therefrom, the elongate tool shaft having a tool axis; a cuff that is configured to attach to a user's wrist or forearm so that the cuff moves with the user's wrist or forearm; and a coupling joint that couples the cuff to the frame so that there is a roll rotational degree of freedom between the cuff and the frame about the tool axis, wherein the cuff and the frame are further rotationally coupled through the first coupling joint or a second coupling joint so that there is a pitch or yaw rotational degree of freedom between the cuff and the frame about a second axis, further wherein, when the cuff is attached to the user's wrist or forearm, the tool axis passes through a center region of the user's wrist. In general, the minimal access tools described herein may also be referred to as remote access tool, as they may be used to act on an object that is remote from the user at the end of a tool shaft. Although most of the apparatuses described herein are surgical tools, they are not limited to such; and may be used for non-surgical applications, including industrial applications, home use, or the like, in which remote operation of an end effector through an elongate tool shaft is desired.

Thus, in any of these apparatuses, the apparatus may be configured so that the rotational axis for each of the additional rotational degrees of freedom also pass through the same point within a region of the cuff so that the intersection point for these rotational axes will intersect within the user's body part (e.g., wrist and/or forearm) at the same general location when the body part is held within the cuff.

In any of the apparatuses described herein in which a coupling joint between the frame and the cuff is configured to permit roll, the apparatus may be configured to permit continuous roll rotation of the frame with respect to the user's wrist or forearm. Thus, for example, the user's hand extending from the cuff may be used to roll the frame relative to the cuff about the roll (e.g., tool) axis continuously in either a clockwise and/or counterclockwise rotation, permitting continuous rotation of an end effector at the distal end of the tool shaft without sweeping the distal end of the tool shaft. In this instance, the user's hand drives the roll rotation (e.g. by means of a twirling motion of the thumb/fingers or a roll motion of the palm) of the overall device via a handle that is connected to the frame through an input joint. The input joint may have one or more degrees of freedom (between the handle and the frame) but constrains (and therefore transmits) roll from the handle to the frame. Thus, the roll of the device (i.e. the frame and tool shaft about the roll (e.g. tool) axis can be accomplished directly, as opposed to indirectly via a mechanical transmission or electromechanical transmission.

In any of these apparatuses, the coupling joint may comprise one or more bearings (e.g., a plain bearing configured as a sled or a rolling element bearing) configured to slide and/or roll to provide the roll rotational degree of freedom. If the coupling joint is a bearing such as a plain bearing or a rolling element bearing, the bearing may slide or roll in a track. The track may be formed on the cuff, the frame, or on another element (e.g., gimbal). For example, the one or more bearings may comprise a plain bearing configured as a sled.

In any of the variations described herein, the tool, and in particular, but not limited to, the cuff, may include a securement configured to hold the user's body part (e.g., the user's wrist, forearm or upper arm) within the cuff. The securement may help secure the user's body part in the cuff so that the cuff moves with the user's body part. In some variations an additional, separate securement is not necessary; for example, the cuff may be formed of material such that it secures around the body part snugly without additional structure being necessary. In some variations the securement is part of the cuff or integral with the cuff. In some variations the securement is attached to the cuff (e.g., to close it around the body part). For example, a cuff may include a securement configured to hold the user's wrist or forearm within the cuff and the securement may include at least one of: a strap, a snap, a belt, an elastic, a latch and hook connector, a tie, or a clamp.

Any of the apparatuses described herein may include a control such as a handle that can be manipulated by a portion of the user's body distal to the attachment site for the cuff. For example, an apparatus may include a handle coupled to the frame through an input joint having at least one degree of freedom (e.g., having two or more degrees of freedom). The handle may be coupled to the frame through a parallel kinematic input joint having at least two degrees of freedom, such as a parallel kinematic input joint having at least two rotational degrees of freedom, wherein the parallel kinematic input joint constrains roll so that roll is transmitted from the handle to the frame. In general, any appropriate input mechanism or control may be used, such as a handle, pedal, etc., compatible with a motion input (e.g., input joint) and a transmission (e.g., cable transmission) for transmitting the motion input from the control to an end effector.

For example a parallel kinematic input joint having two degrees of freedom may include: at least two independent paths for transmission of motion coupling the handle to the tool frame, wherein the at least two independent paths comprise a first path and a second path; a first intermediate body in the first path that is connected to the tool frame by a first connector and to the handle by a third connector; and a second intermediate body in the second path that is connected to the frame by a second connector and to the handle by a fourth connector; wherein the first connector and the fourth connector both allow rotation in a first rotational direction and restrict rotation in a second rotational direction; further wherein the second and third connectors allow rotation in the second rotational direction and restrict rotation in the first rotational direction.

In this example, which is described in greater detail in U.S. patent application Ser. No. 15/054,068, filed on Feb. 25, 2016, and titled "PARALLEL KINEMATIC MECHANISMS WITH DECOUPLED ROTATIONAL MOTIONS" (previously incorporated by reference in its entirety), a joint (e.g., a coupling joint, a connector, etc.) that constrains a degree of freedom motion (e.g., roll, pitch, yaw) transmits that motion between the rigid bodies that it joins. Thus, for example, any of these apparatuses may include a handle coupled to the frame through an input joint having at least one rotational degree of freedom, wherein the input joint constrains roll rotation so that roll is transmitted from handle to frame.

Any of these apparatuses may include an end effector coupled to the frame through an output joint. The output joint may be a flexible, snake-like output joint. For example, the output may comprise flexible disks attached in a fashion such that the direction of flexure of each element alternates. This output joint can be actuated by pushing or pulling on the disks causing expansion and contraction of its sides. Thus, motion of the input joint may be transmitted to the output joint by a transmission, such as a mechanical transmission (e.g., cable-driven transmission). Alternatively, the output joint may comprise a series links or disks connected serially with alternating rotational axes.

In addition to a roll-rotation coupling joint (e.g., a bearing) adapted to provide roll rotation about the tool axis, one or more additional coupling joint between the cuff and the frame may be configured so that there is a rotational degree of freedom between the cuff and the frame about a second axis. The additional rotational degree of freedom may be pitch, yaw, or pitch and yaw. For example, the coupling joint may also be rotationally coupled so that there is a pitch or yaw rotational degree of freedom between the cuff and the frame about a second axis. As mentioned above, the second (or in some cases third) rotational axis may intersect the tool axis (roll axis) within a part of the user's body part that is held within the cuff.

In any of the apparatuses described herein, the same coupling joint may be configured to provide more than one rotational and/or translational degree of freedom. For example, the same coupling joint may be configured as both a gimbal joint (e.g., rotating about a fixed axis) and as a bearing (e.g., plain bearing such as a sled), to provide roll. Alternatively or additionally, a second or third (or more) coupling joint may be included that provides additional degrees of freedom between the cuff and the frame. In any of these cases, coupling joints may be nested, or arranged sequentially, so that when the coupling joint couple between the frame and the cuff, they are indirectly coupled to either or both the frame and the cuff. For example, a first coupling joint may be coupled directly to the frame and indirectly to the cuff through a second coupling joint, while the second coupling joint may be coupled indirectly to the frame through the first coupling joint and directly to the cuff. Recall as well that in some variations the cuff is integral to one of the coupling joints, so that the cuff is part of the coupling joint itself.

For example, a tool configured for roll rotation about the tool axis may include a second coupling joint between the cuff and the frame so that there is a pitch rotational degree of freedom between the cuff and the frame about a second axis, and the tool may further comprise a third coupling joint between the cuff and the frame so that there is a yaw rotational degree of freedom between the cuff and the frame about a third axis, wherein the coupling joint, the second coupling joint and the third coupling joint are serially connected between the cuff and the frame. The coupling joints may be serially connected in any order.

In another example, a tool configured for roll rotation about the tool axis may include a second coupling joint between the cuff and the frame so that there is a pitch rotational degree of freedom between the cuff and the frame about a second axis, and further wherein the coupling joint is also rotationally coupled so that there is a yaw rotational degree of freedom between the cuff and the frame about a third axis, wherein the coupling joint and the second coupling joint are serially connected between the cuff and the frame.

Another example of an apparatus configured for roll rotation about the tool axis may include a second coupling joint between the cuff and the frame so that there is a pitch rotational degree of freedom between the cuff and the frame about a second axis, the tool further comprising a third coupling joint between the cuff and the frame so that there is a yaw rotational degree of freedom between the cuff and the frame about a third axis, wherein the second axis and the third axis intersect with the tool axis through the center region of the user's wrist when the cuff is attached to the user's wrist or forearm.

Any of the coupling joints described herein may be more specifically configured as gimbals (e.g., as part of a gimbal). As used herein the gimbal refers to each of the pivoting mounts that may form a gimbal assembly. The gimbal may include a gimbal frame that extends completely around a central region or part way (e.g., half) around a central region. The gimbal frame may be, but does not have to be, a ring or arc. Each gimbal may include one pivot joint extending from the gimbal frame (or the frame may receive one or a pair of pivot points); when a pair of pivot points (e.g., pivot pins or holes to receive pivot pins) are included they are separated by 180 degrees around the central region. A gimbal assembly may include multiple gimbals that are arranged (typically, though not necessarily, so that their respective axes of rotation are 90 degree offsets from each other).

For example, an apparatus (e.g., a tool) configured for roll rotation about the tool axis of a tool arm may further include a second coupling joint between the cuff and the frame in which the second coupling joint is configured as first gimbal that is rotationally coupled to the frame to provide either pitch or yaw rotation about a second axis, wherein the second axis intersects with the tool axis through the center region of the user's wrist when the cuff is attached to the user's wrist or forearm. In some variations, an apparatus may include a second coupling joint between the cuff and the frame, the second coupling joint comprising a first gimbal that is rotationally coupled between the cuff and the frame to provide pitch rotation about a second axis, and a third coupling joint between the cuff and the frame, the third coupling joint comprising a second gimbal rotationally coupled between the cuff and the frame to provide yaw rotation about a third axis, wherein the second axis and third axis intersect with the tool axis through the center region of the user's wrist when the cuff is attached to the user's wrist or forearm.

Also described herein are minimal access tools that mount to a user's wrist or forearm so that the tool may roll about a roll axis intersecting (e.g., extending through) the user's wrist or forearm. For example a tool may include: a frame comprising an elongate tool shaft having a tool axis; a cuff that is configured to attach to the user's wrist or forearm; a first gimbal rotationally coupled between the frame and the cuff so that there is a first rotational degree of freedom between the frame and the cuff about a first axis; a bearing between the frame and the cuff and configured to slide relative to the frame or the first gimbal so that there is a roll rotational degree of freedom between the frame and the cuff about the tool axis, wherein, when the cuff is attached to the user's wrist or forearm, the tool axis and the second axis intersect within the user's wrist or forearm.

A minimal access tool that mounts to a user's wrist or forearm so that the tool may roll about a roll axis intersecting the user's wrist or forearm may include: a frame comprising an elongate tool shaft having a tool axis; a cuff having a passage therethrough that is configured to hold a wrist or forearm of the user; a first gimbal rotationally coupled between the frame and the cuff so that there is a first rotational degree of freedom between the frame and the cuff about a first axis; a bearing between the frame and the cuff and configured to slide so that there is a roll rotational degree of freedom between the frame and the cuff about the tool axis, wherein, when the cuff is attached to the user's wrist or forearm, the tool axis and the first axis intersect within the passage through the cuff; and a securement configured to hold the user's wrist or forearm in the cuff so that the cuff moves with the user's wrist or forearm.

A minimal access tool that mounts to a user's wrist or forearm so that the tool may roll about a roll axis that extends through the user's wrist or forearm, the tool comprising: a frame comprising an elongate tool shaft having a tool axis; a cuff that is configured to attach to the user's wrist or forearm; a first gimbal rotationally coupled between the cuff and the frame so that there is a pitch rotational degree of freedom between the frame and the cuff about a first axis; a second gimbal rotationally coupled between the cuff and the frame so that there is a yaw rotational degree of freedom between the frame and the cuff about a second axis; a bearing between the cuff and the frame and configured to slide so that there is a roll rotational degree of freedom between the frame and the cuff about the tool axis, wherein, when the cuff is attached to the user's wrist or forearm, the tool axis, the first axis and the second axis intersect at a point within the user's wrist or forearm; and a securement configured to hold the user's wrist or forearm in the cuff so that the user's hand extends through the first gimbal and the second gimbal and the cuff moves with the user's wrist or forearm.

As mentioned above, and in particular for the minimal access tools that mount to a user's wrist or forearm so that the tool may roll about a roll axis intersecting the user's wrist or forearm and include one or more additional degrees of freedom, when multiple coupling joints are used, e.g., bearings and/or gimbals, the coupling joints may be serially connected in any order. For example, the first gimbal and the bearing may be serially connected between the cuff and the frame. In a variation having a bearing and two gimbals, the first gimbal, the second gimbal and the bearing may be serially connected between the cuff and the frame in any order. For example, the first gimbal may be rotatably coupled to the frame and the bearing may be slideably coupled to the first gimbal. The bearing may be slideably coupled to the frame and the first gimbal rotatably coupled to the bearing.

In some variations the tool further includes a second gimbal rotationally coupled between the frame and the cuff so that there is a second rotational degree of freedom between the frame and the cuff about a second axis, wherein when the cuff is attached to the user's wrist or forearm, the tool axis, the first axis and the second axis intersect at a point within the user's wrist or forearm.

As already mentioned, the cuff may be part of the first gimbal. In any of the apparatuses described herein, the cuff may be configured to removably attach within the first gimbal. Alternatively or additionally, the first gimbal may be configured to removably attach to tool. This may permit the cuff to be attached to the arm and then connected to the tool, or the arm attached to the cuff to be removed from the tool before removing the arm from the cuff, as will be described in greater detail below.

In any of the apparatuses described herein, the bearing may be part of the first gimbal. The bearing may be configured to permit continuous roll rotation of the frame with respect to the user's wrist or forearm. The bearing may be a plain bearing configured as a sled extending in a ring around the cuff or a rolling element bearing extending in a ring the cuff.

Also described herein are methods of using any of the apparatuses described herein. For example, described herein are methods of operating a minimal access tool, wherein the minimal access tool includes a frame comprising an elongate tool shaft having a tool axis, the method comprising: securing a user's forearm or wrist within a cuff so that the user's wrist or forearm extends through a first gimbal and is retained in the cuff wherein there is a roll rotational degree of freedom about the tool axis between the cuff and the frame through a bearing that slides and wherein there is a second rotational degree of freedom between the cuff and the frame through the first gimbal; changing either or both of an angle or a roll position of the user's wrist or forearm relative to the tool axis as the user moves the user's arm, by one or both of: rotating the first gimbal about a second rotational axis, and sliding the bearing to roll about the tool axis, wherein the second rotational axis and the tool axis intersect at a point of intersection that is within the user's wrist or forearm.

In general, during use, the cuff may be attached to a user forearm while the frame provides an extended reference ground for a minimal or remote access device. This type of arrangement may be useful in minimal/remote access steerable devices that are meant to transfer motion inputs from a user's forearm, wrist, hand, and fingers to corresponding motion outputs of an end-effector at a remote location.

The step of securing the user's wrist or forearm may comprise securing the user's forearm or wrist with a securement comprising one or more of: a strap, a snap, a belt, a latch and hook connector, a tie, or a clamp.

Any of these methods may include coupling a distal region of the elongate tool shaft to a mount. In a minimally invasive surgery application, the mount may be a trocar, cannula, or other point that serves as a fulcrum. For example, the method may include coupling a distal region of the elongate tool shaft to a mount, wherein changing either or both the angle or roll position of the user's wrist or forearm relative to the tool axis comprises leaving the distal end of region of the elongate member coupled to the mount as either or both of the angle and roll position of the user's wrist or forearm are changed relative to the elongate tool shaft.

Any of these methods may include manipulating a handle coupled to the tool shaft through an input joint to articulate an end effector coupled to a distal end of the elongate member of the tool frame via an output joint.

The method may include manipulating a handle coupled to the tool frame in pitch, yaw or pitch and yaw rotations, wherein the handle is coupled to the tool frame through a parallel kinematic input joint that transmits pitch and yaw rotation through corresponding rotations of an output joint comprising a multi-link end effector joint.

Also described herein are minimal access tools that include a forearm attachment to a frame to provide rotation in pitch and yaw that may optionally include roll (e.g., roll about the tool axis).

For example, described herein are minimal access tool comprising: a frame having an elongate tool shaft, the elongate tool shaft having a tool axis; a cuff that is configured to attach to a user's wrist or forearm; a coupling joint between the cuff and the frame so that there is a first rotational degree of freedom between the cuff and the frame about a first axis; wherein, when the cuff is attached to the user's wrist or forearm, the first axis passes through a center region of the user's wrist or forearm, and further wherein the tool axis intersects with the first axis at the center region of the user's wrist or forearm; and a securement configured to hold the user's wrist or forearm in the cuff so that the user's hand extends out of the cuff and so that the cuff moves with the user's forearm. In general, any of these apparatuses may be configured so that the multiple rotational axes (e.g., a first rotational axis and a second rotational axis, intersect at a point within user's wrist or arm when the user's wrist or arm is held in the cuff). In any of these variations, the first, second, or third axes may be a pitch axis or a yaw axis.

A minimal access tool for mounting to a user's wrist or forearm may include, the tool comprising: a frame having an elongate tool shaft, the elongate tool shaft having a tool axis; a cuff configured to hold the user's wrist or forearm therein; a first coupling joint between the cuff and the frame, wherein the first coupling joint is configured to rotate about a first axis; a second coupling joint between the cuff and the frame, wherein the second coupling joint is configured to rotate about a second axis, wherein the first axis and the second axis intersect at a point of intersection; and a securement configured to hold the user's wrist or forearm in the cuff so that the user's hand extends through the cuff and cuff moves with the user's wrist or forearm and further wherein the point of intersection is within the user's wrist or forearm. The apparatus may include a third coupling joint coupled between the cuff and the frame, wherein the third coupling joint is configured to rotate about a third axis. In any of these variations, the first axis may be the tool axis.

A minimal access tool for mounting to a user's arm may include: a frame having an elongate tool shaft; a cuff configured to attach to the user's wrist or forearm; a coupling joint between the cuff and the frame that provides at least one rotational or translational motion between the cuff and the frame; a handle configured to receive the user's hand, the handle connected to the frame via an input joint, wherein the input joint is a parallel kinematic input joint that provides at least one degree of freedom; an end-effector connected to the tool shaft via an output joint; and a transmission system to transmit the at least one degree of freedom of the input joint to a corresponding at least one degree of freedom of the output joint.

Any of these apparatuses (e.g., tools) may be configured such that the first coupling joint comprises a bearing configured to slide so that there is a roll rotational degree of freedom between the frame and the cuff about the tool axis. In some variations, the first coupling joint comprises a first gimbal rotationally coupled between the cuff and the frame so that there is a first rotational degree of freedom between the frame and the cuff about the first axis. For example, the second coupling joint may comprise a second gimbal rotationally coupled between the cuff and the frame so that there is a second rotational degree of freedom between the frame and the cuff about the second axis; or the second coupling joint may comprise a bearing configured to slide so that there is a roll rotational degree of freedom between the frame and the cuff about the tool axis. The first coupling joint may be a first gimbal rotatably coupled to the frame and the second coupling joint is a second gimbal that is rotatably coupled to the first gimbal.

Also described herein are methods of operating a minimal access tool having a frame and a tool shaft extending therefrom. For example, a method may include: securing a user's wrist or forearm within a gimbal assembly of the minimal access tool, so that the user's wrist or forearm extends through the gimbal assembly and the user's hand passes beyond the gimbal assembly and may move independently of the gimbal assembly, wherein the gimbal assembly comprises a first coupling joint and a second coupling joint, wherein the first coupling joint is rotationally coupled to the frame to rotate about a first axis, and the second coupling joint is rotationally coupled to the first coupling joint to rotate about a second axis; changing the angle of the user's wrist or forearm relative to the tool shaft by rotating, as the user moves the user's wrist or forearm, one or more of: the first coupling joint about the first axis and the second coupling joint about the second axis, wherein the first axis and the second axis intersect at a point of intersection that is within the user's wrist or forearm.

The step of securing the user's wrist or forearm may comprise securing the user's forearm or wrist with a securement comprising one or more of: a strap, a snap, a belt, a latch and hook connector, a tie, or a clamp. Any of these methods may include coupling a distal region of the elongate tool shaft to a mount. For example, any of these methods may include coupling a distal region of the elongate tool shaft to a mount, wherein changing either or both the angle or roll position of the user's wrist or forearm relative to the tool axis comprises leaving the distal end of region of the elongate member coupled to the mount as either or both of the angle and roll position of the user's wrist or forearm are changed relative to the elongate tool shaft.

The method may include manipulating a handle coupled to the tool shaft through an input joint to actuate or control an end effector joint coupled to a distal end of the elongate member of the tool frame.

The method may include manipulating a handle coupled to the tool frame in pitch, yaw or pitch and yaw rotations, wherein the handle is coupled to the tool frame through a parallel kinematic input joint that transmits pitch and yaw rotation through to an output joint at an end effector. The output joint may be a multi-link joint that allows articulation.

Also described herein are minimal access tools that include both the body attachment elements described above, a frame with a tool shaft, and an output joint at the end of the tool shaft that is actuated by, e.g., a handle coupled to a parallel kinematic input joint having two or more degrees of freedom. For example, described herein are minimal access tools comprising: a frame comprising an elongate tool shaft having a tool axis; a cuff having a passage therethrough that is configured to hold a wrist or forearm of the user; a first gimbal between the cuff and the frame so that there is a pitch rotational degree of freedom between the frame and the cuff about a first axis; a second gimbal between the cuff and the frame so that there is a yaw rotational degree of freedom between the frame and the cuff about a second axis; a bearing between the cuff and the frame, the bearing configured to slide or roll so that there is a roll rotational degree of freedom between the cuff and the frame about the tool axis, wherein the first gimbal, the second gimbal and the third gimbal are serially connected between the cuff and the frame, and further wherein the tool axis, the first axis and the second axis all intersect at a point within passage through the cuff; and a securement configured to hold the user's wrist or forearm in the cuff so that the user's hand extends through the first gimbal and the second gimbal and the cuff moves with the user's wrist or forearm; a handle coupled to the frame through an input joint having at least one degree of freedom; and an end-effector connected to the tool shaft via an output joint; and a transmission system to transmit the at least one degree of freedom of the input joint to a corresponding one or more degrees of freedom of the output joint.

As mentioned above, in any of these apparatuses, including to tool described above, the first gimbal may be nested within the second gimbal. The cuff may be integral to the first gimbal.

In any of these variations, the input joint may comprise a parallel kinematic input joint, including a parallel kinematic input joint having: at least two independent paths for transmission of motion coupling the handle to the tool frame, wherein the at least two independent paths comprise a first path and a second path; a first intermediate body in the first path that is connected to the tool frame by a first connector and to the handle by a third connector; and a second intermediate body in the second path that is connected to the frame by a second connector and to the handle by a fourth connector; wherein the first connector and the fourth connector both allow rotation in a first rotational direction and restrict rotation in a second rotational direction; further wherein the second and third connectors allow rotation in the second rotational direction and restrict rotation in the first rotational direction.

The cuff may be within a channel through the first gimbal; alternatively or additionally, the cuff may be formed from (e.g., integral to) the first gimbal. The cuff may be configured to removably attach within the first gimbal. The tool of claim 1, wherein the bearing may be configured to permit continuous roll rotation of the frame with respect to the user's wrist or forearm. For example, the bearing may be a sled sliding within a track around the cuff. The first gimbal may be configured to removably attach to the tool.

In general, any of the apparatuses described herein may advantageously include a cuff (which may be part of a coupling joint such as a gimbal) that can be removably coupled into and out of the tool. As mentioned briefly above, this may permit the user to easily attach the cuff to their body (e.g., their wrist and/or forearm) and then attach it to the tool, e.g., by snapping into tool so that it may then operate as described and illustrated herein. Similarly, to remove the tool (or to switch between tools having different end effectors, for example), the user may uncouple the cuff (and/or a coupling joint including the cuff) from the tool. These embodiments may be incorporated into any of the apparatuses described herein, but may be particularly effective in variations including gimbals as one or more of the coupling joints, especially where the cuff is formed from one of the input joints (e.g., gimbals).

For example, a forearm attachment device for a minimal access tool may include: a frame comprising an elongate tool shaft having a tool axis; an outer gimbal rotationally coupled to the frame, and an inner gimbal rotationally coupled or coupleable to the outer gimbal, wherein the inner gimbal, when coupled to the outer gimbal, is configured to rotate about a first rotational axis containing the at least one releasable attachment coupling the inner gimbal to the outer gimbal, and wherein the outer gimbal is configured to rotate about a second rotational axis, and wherein the first rotational axis and the second rotational axis intersect at a point of intersection; a cuff within the inner gimbal configured to hold a user's arm therein so that the point of intersection is within the user's arm; and a securement configured to secure the user's arm in the cuff so that the cuff moves with the user's arm.

The releasable coupling may be any appropriate releasable connection, but in particular may be configured to provide tactile and/or audible feedback when coupling/uncoupling. For example, the inner gimbal may be configured to releasably snap into the outer gimbal.

The inner gimbal may comprise at least one projection (e.g., pin, also referred to as a pivot pin) extending from the inner gimbal and configured to releasably mate with the outer gimbal. Alternatively or additionally, the inner gimbal may comprise at least one projection receiver on an outer surface of the inner gimbal configured to receive and releasably mate with a projection (e.g., pin) from the outer gimbal. The inner gimbal may comprise at least one projection (e.g., pin) or projection receiver on an outer surface of the inner gimbal configured to mate with a projection or projection receiver on the outer gimbal, wherein the at least one projection or projection receiver are in the first rotational axis.

The cuff and/or the coupling joint (e.g., gimbal) holding the cuff may be configured to include a release from the tool. For example, when the cuff is part of the inner gimbal that is releasably coupled to the outer gimbal and/or the frame, the inner gimbal may be configured to be compressed to decouple from the outer gimbal. Alternatively or additionally a release control (button, switch, slider, etc.) may be included. Where the gimbal is attached by one or two pivot pins, for example, one of the pivot pins or both may be spring-loaded.

In any of the apparatuses described herein, the apparatus may include a sleeve in addition to the cuff. The sleeve may couple into the cuff and may be applied by the user before coupling to the cuff to enhance comfort and/or fit. For example the apparatus may include a sleeve configured to rigidly attach within an opening formed by the inner gimbal (e.g., a cuff), further wherein the sleeve is configured to couple the user's wrist or forearm to the cuff.

In any of the tools including a releasable cuff portion, the apparatus may be configured for roll rotation, and may include a bearing between the cuff and the frame that is configured to slide so that there is a roll rotational degree of freedom between the frame and the cuff about a long axis of the tool shaft.

Also described herein are methods of using these releasable cuff apparatuses. For example, a method of attaching a minimal access tool to a user's arm may include: securing a user's wrist or forearm within a cuff that is uncoupled from the minimal access tool, so that the user's hand extends out of the cuff while the user's wrist or forearm is secured within the cuff; attaching the cuff into a frame of the minimal access tool, wherein the cuff is part of or coupled to a first coupling joint that can rotate about a first rotational axis relative to the frame; rotating the frame relative to the cuff about the first rotational axis as the user moves the user's wrist or forearm; and rotating the frame relative to the cuff about a second rotational axis as the user moves the user's wrist or forearm, wherein the first rotational axis and the second rotational axis intersect at a point of intersection that is within the user's wrist or forearm.

The first coupling joint may be removable, as discussed above, for inserting the user's arm into the cuff, or the cuff may be removable and inserted into the first coupling joint where it rigidly attaches thereto. The first coupling joint may be a bearing and/or a gimbal, as described herein. The first rotational motion may be in pitch, yaw or roll, and the second rotational motion, which may be performed by a second coupling joint (e.g., bearing or gimbal) or the same first coupling joint.

For example, a method of attaching a minimal access tool to a user's arm may include: securing a user's forearm within an inner gimbal so that the user's forearm extends through the inner gimbal; wherein the inner gimbal member forms part of a gimbal assembly comprising the inner gimbal, a frame and an outer gimbal, wherein the outer gimbal is rotationally coupled to the frame and the inner gimbal is rotationally coupled to the outer gimbal; rotating the inner gimbal about a first rotational axis of the gimbal assembly as the user moves the user's forearm; and rotating the outer gimbal about a second rotational axis of the gimbal assembly as the user moves the user's forearm, wherein the first rotational axis and the second rotational axis intersect at a point of intersection that is within the user's forearm.

The method may also include attaching the inner gimbal member into the gimbal assembly so that the inner gimbal can rotate about the first rotational axis after securing the user's forearm within the inner gimbal. For example, the method may also include snapping the inner gimbal member into the gimbal assembly so that the inner gimbal can rotate about the first rotational axis after securing the user's forearm within the inner gimbal.

A method may also include attaching the inner gimbal member into the gimbal assembly by mating a projection or projection receiver on an outer surface of the inner gimbal with a complementary projection or projection receiver on an inner surface of the outer gimbal so that the inner gimbal can rotate about the first rotational axis through the projection or projection receiver after securing the user's forearm within the inner gimbal.

Any of these methods may include attaching, after securing the user's forearm within the inner gimbal, the inner gimbal member into the gimbal assembly by compressing the inner gimbal so that it fits into the outer gimbal member and releasing the compression to mate the inner gimbal with the outer gimbal so that the inner gimbal can rotate about the first rotational axis. In general, the methods may include securing the user's forearm within the inner gimbal so that the inner gimbal moves with the user's arm.

The cuff may be secured at least partially around a user's forearm so that the cuff moves with the user's forearm, wherein placing the user's forearm within the inner gimbal comprises securing the cuff within the inner gimbal so that the inner gimbal moves with the user's forearm. For example, securing a user's forearm within the inner gimbal may comprise placing the user's forearm into a cuff within the inner gimbal and securing the user's forearm in the cuff using a securement.

The step of rotating the inner gimbal about the first rotational axis may comprise rotating the inner gimbal around a yaw axis. Rotating the outer gimbal around the second rotational axis may comprise rolling the outer gimbal around a pitch axis.

For example, a method of attaching a minimal access tool to a user's forearm may include: coupling an inner gimbal member to a user's forearm so that the user's forearm passes through the inner gimbal; attaching the inner gimbal member coupled to the user's forearm into a gimbal assembly comprising a frame and an outer gimbal, wherein the outer gimbal is rotationally coupled to the frame, so that the inner gimbal is rotationally coupled to the outer gimbal; rotating the inner gimbal about a first rotational axis; and rotating the outer gimbal about a second rotational axis, wherein the first rotational axis and the second rotational axis intersect at a point of intersection that is within the user's forearm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4, 5, 6A-6C, 7A, 7B, 8A, 8B, and 9 show different degrees of freedom on a user's arm (wrist, forearm and fingers).

FIGS. 11 and 12 illustrate orientation of a minimal access tool that may be difficult to achieve with prior art devices, such as those shown in FIGS. 1-3.

FIGS. 13A-13C and 14A-14B illustrate arm movements that may be difficult or impossible to achieve using prior art minimal access tools such as those shown in FIGS. 1-3.

FIGS. 19 and 20 illustrate a first embodiment of forearm attachment assemblies (components) that may be used with a minimal access tool as descried herein. FIG. 19 shows one variation of an assembly of coupling joints including two gimbals and a bearing, that may provide a coupling between a cuff (integrated into the inner gimbal) and a frame allowing rotation in pitch, yaw and roll, where the frame may be configured (as shown in FIG. 21A) for roll about the tool axis. FIG. 20 shows a bearing comprising a plurality of rollers.

FIG. 21A illustrates another example of a forearm attachment assembly integrated into a minimal access tool, showing 3 axes of rotation (pitch, yaw, roll).

FIGS. 21B-21D show translational DoFs: axial (FIG. 21B), horizontal (FIG. 21C), and vertical (FIG. 21D). FIGS. 21E-21G show rotational DoFs: roll (FIG. 21E), pitch (FIG. 21F) and yaw (FIG. 21G).

FIGS. 53A and 53B shows a front and side profiles, respectively, of the gimbal including the cuff opening and a pair of spring-loaded pins that secure it into another gimbal, as illustrated in FIG. 53D so that it may rotate about a rotational axis. FIG. 53C show a sectional view of a second gimbal into which the spring-loaded pins may be inserted.

DETAILED DESCRIPTION

Figure 1:
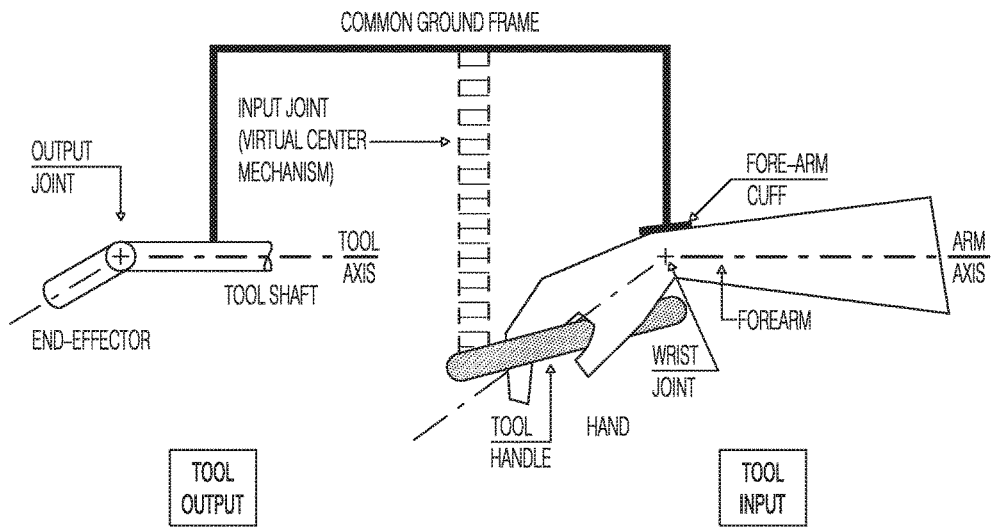
FIGS. 1, 2 and 3 illustrate prior art minimally invasive/remote access tools.
Figure 2:
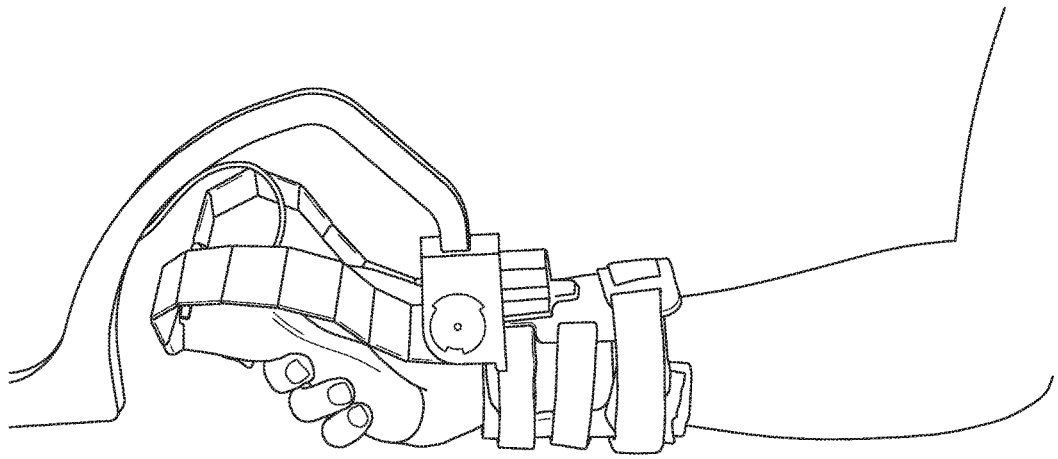
Figure 3:
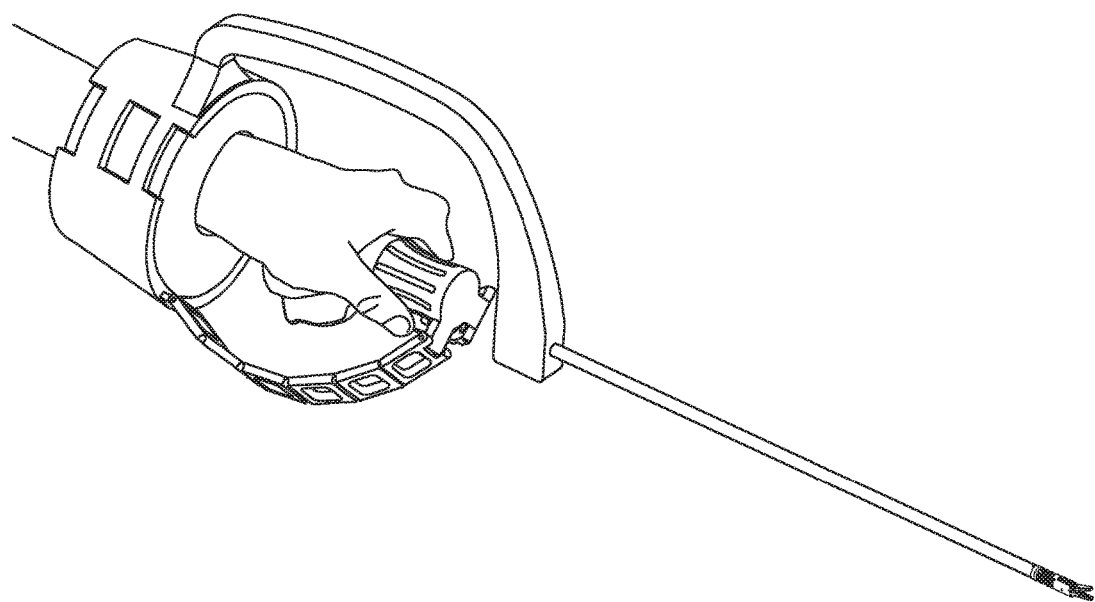
Figure 4:
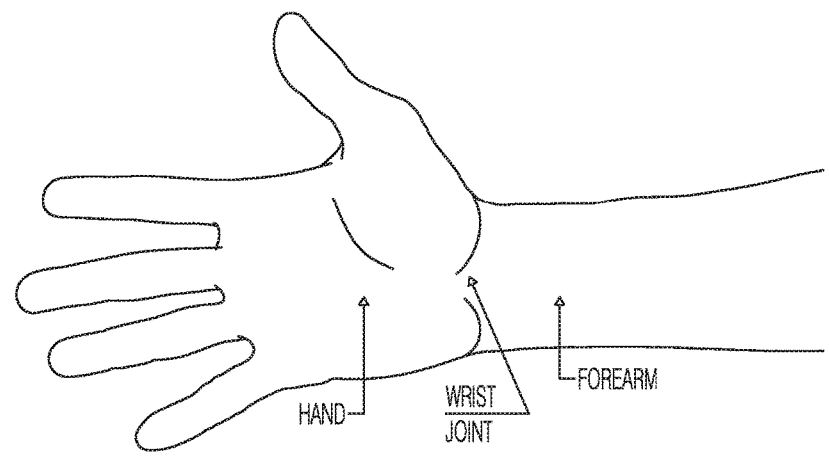
Figure 5:
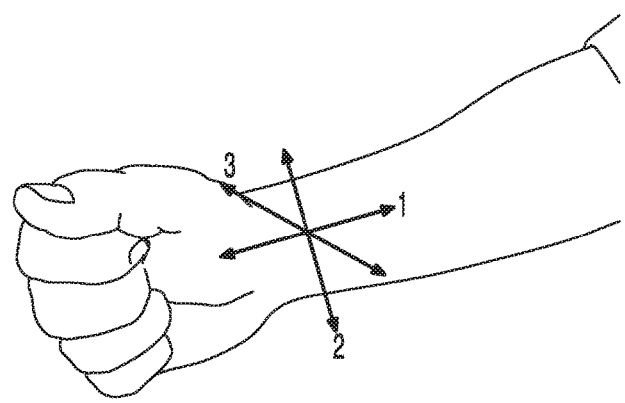
Figures 6A, 6B, 6C:
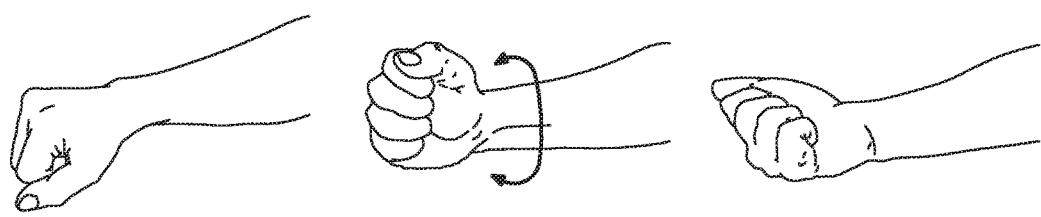
Figure 10:
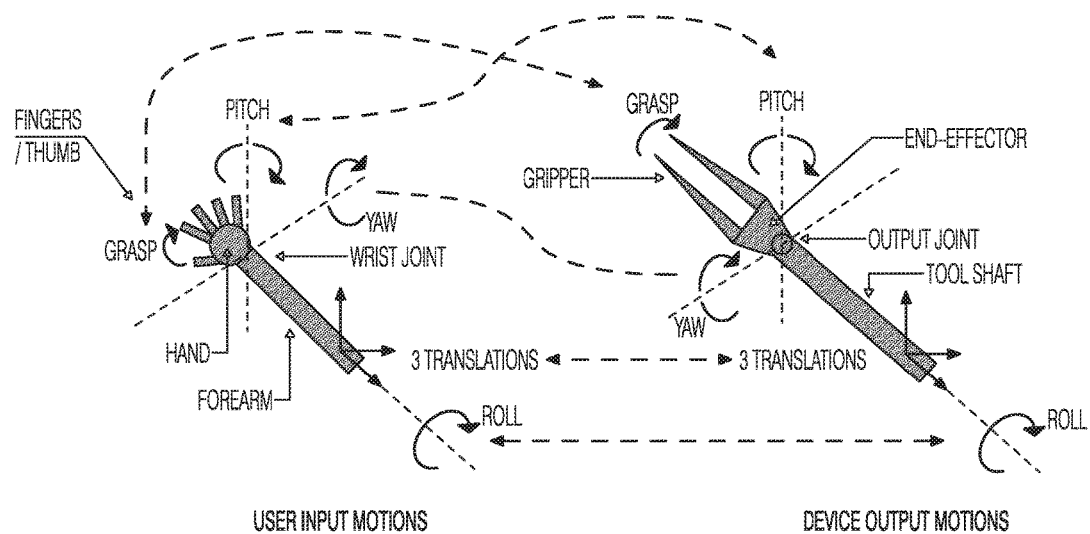
FIG. 10 illustrates the translation of arm movement using a minimally access tool (e.g., remote access tool).
Figure 11:
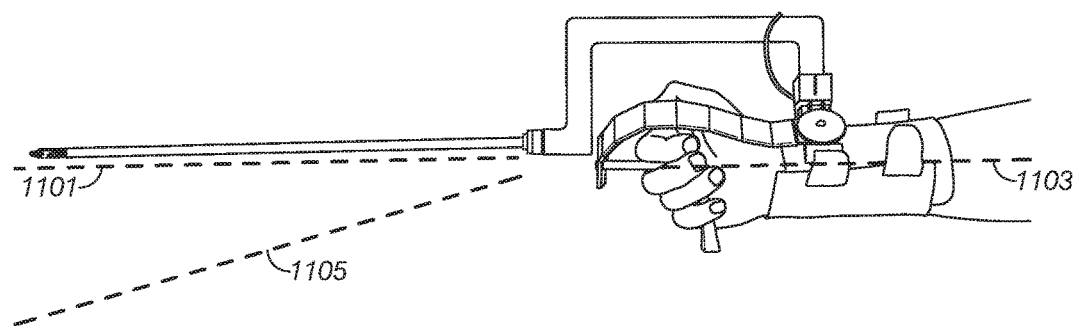

In general, described herein are body attachment apparatuses (e.g., devices, systems, assemblies, tools, etc.) including forearm attachment assemblies that may be used with (and/or integrated into) a minimal access tool to provide up to four degrees of freedom, e.g., three rotational and one translational, between a body attachment such as a cuff that may be part of the forearm attachment assembly and a frame of the tool. These degrees of freedom (DoF) may be achieved via a connection (which may be referred to as a joint and/or mechanism) between the cuff and the frame. This connection may also be referred to herein as a "coupling joint". The remaining two translational motions may be constrained and therefore transmitted directly between the cuff and the frame. For convenience, the body attachment assemblies described herein may be referred to as "arm attachment assemblies" or "forearm attachment assemblies," although they may be adapted for use in other body regions, including the legs (lower leg, ankle, upper leg), or other portions of the arm (wrist, forearm, upper arm). In ordinary usage herein, unless the context makes clear otherwise, a "forearm attachment assembly" may attach to either the wrist or forearm.

Although four degree of freedom variations are described herein, additional variations of these body attachment apparatuses, and therefore of the minimal access tools incorporating them, may instead provide fewer than four DoF. For example, a minimal access tool as described herein may include three rotational degrees of freedom (yaw, pitch and roll), or two rotational degrees of freedom (e.g., yaw and roll, pitch and roll or yaw and pitch). In some variation only one rotational degree of freedom (e.g., roll) is provided.

As mentioned, in general a forearm attachment assembly may be used as part of an apparatus such as a minimal remote access tool. In general, the minimal remote access tool may include a shaft which may be integral and/or rigidly connected to the frame. The frame may be considered the apparatus mechanical ground. Alternatively, in some variations the shaft may be connected to the frame by a joint (e.g., a universal joint).

Some variations of the apparatuses described herein that may be particularly useful are configured such that the tool shaft is integral with or rigidly connected to the frame and has an elongate (long) tool axis. Such variations may include a body (e.g., forearm) attachment assembly that is configured to permit roll between the cuff and the tool shaft, so that the roll axis is the same as the tool axis, and this axis passes through the cuff (e.g., a center region of the user's wrist and/or forearm when operating the apparatus). In some variations the forearm attachment assembly also permits rotation about one or more additional axes, such as pitch or yaw. These additional axes may also intersect the roll axis at a point within the user's wrist and/or forearm. Alternatively, in some variations the roll axis intersects the user's wrist and/or forearm, but the additional pitch and/or yaw axes do not. Thus, although the pitch and yaw rotational DoF between the frame and the cuff have been been described to intersect with the roll axis at the user's wrist, in an alternate embodiment these two axes of rotation may be at a location separate from the user's wrist. For example, a minimal access tool may be configured so that the roll rotation is about a tool axis that passes through the wrist region of the user, but the pitch and yaw degrees of freedom may be between the tool frame and tool shaft, or along any other location along the extent of the tool frame or tool shaft. In such a case the roll, pitch and yaw axes would no longer intersect at one point that lies in the user's wrist region.

A cuff may be part of the body attachment assembly or it may be separate and attachable to the body attachment assembly. For example when the cuff is part of a forearm attachment assembly which links to a minimal access tool, the cuff may be securely attached to the forearm of a user, thereby allowing up to 4 DoF between the user's forearm and the frame of the minimal access tool. The coupling joint(s) forming the forearm attachment assembly portion of the tool may be configured so that the two rotational DoF (pitch and yaw) are centered at the wrist joint of the user, the third rotational DoF (roll) is centered around some desirable axis of the frame (e.g., a tool shaft attached to frame) and the translational DoF is along some desirable axis of the frame (e.g. tool shaft attached to frame). The two translational DoF constrain the upward/downward motion at the forearm and the side to side motion at the forearm.

As described above in reference to FIGS. 4-9, the forearm, as it pertains to the apparatuses herein, may be defined as the distal region of a user's arm leading up to, but not inclusive of, the wrist joint along the arm axis. The forearm may be unconstrained in space and offers 4 DoF; rotation about the arm axis accomplished through rotational pronation and supination, as well as forward/reverse translation, upward/downward translation, and side/side translation (as shown in the figures above). The arm axis intersects the hand axis at the user's wrist joint. The wrist joint is defined as an articulating joint between the user's forearm and hand and grants the user two rotational DoF relative to the forearm accomplished through flexion/extension and deviation. The hand is defined as the member of the user's arm that is just distal, but not inclusive of, the wrist joint. The hand axis is controlled by the articulation at the wrist joint while intersecting the arm axis.

In general, the frame of an apparatuses including a minimal access tool may be a rigid elongate extension which cantilevers (i.e. extends) from the user's forearm and interfaces with the forearm via the coupling joint(s) of the body attachment apparatus and can serve as a ground reference for various other components, e.g., sub-systems, joints, or the like in a remotely steerable tool. The frame helps transmit certain DoF directly from the user input at the forearm and hand. For example, the two translational motions (numbered 2 and 3 in FIG. 5) driven by the user's forearm can be directly transmitted by the frame to a remote location.

The coupling joint serves as the interface between the frame and the cuff. This coupling joint may offer up to 3 rotational DoF and one axial translational DoF, and constrains the remaining translational motions. The ability to constrain the translational motions enables the transmission of these specific motions directly from the forearm to the frame by way of the cuff.

In general, the cuff is the interface between the connection mechanism and the user's forearm. The cuff is a semi-rigid body that provides a secure and comfortable fit to the user's forearm, and captures all the motions of the forearm. The cuff is tethered to the forearm such that it does not hinder the articulation occurring at the user's wrist joint while ensuring that the rotational axes of all the rotational DoF of the coupling joint pass through the user's wrist joint.

In contrast to the attachment mechanisms previously described (e.g., U.S. Pat. No. 8,668,702) the forearm attachments described herein, the forearm attachments described herein typically include a cuff assembly (coupling joint) configured to attach to the forearm and provide one or more degrees of freedom between the frame and the forearm, so that the only some of the possible motions (DoF) of the forearm are transmitted to the frame, and vice versa, as described herein.

Figure 16:
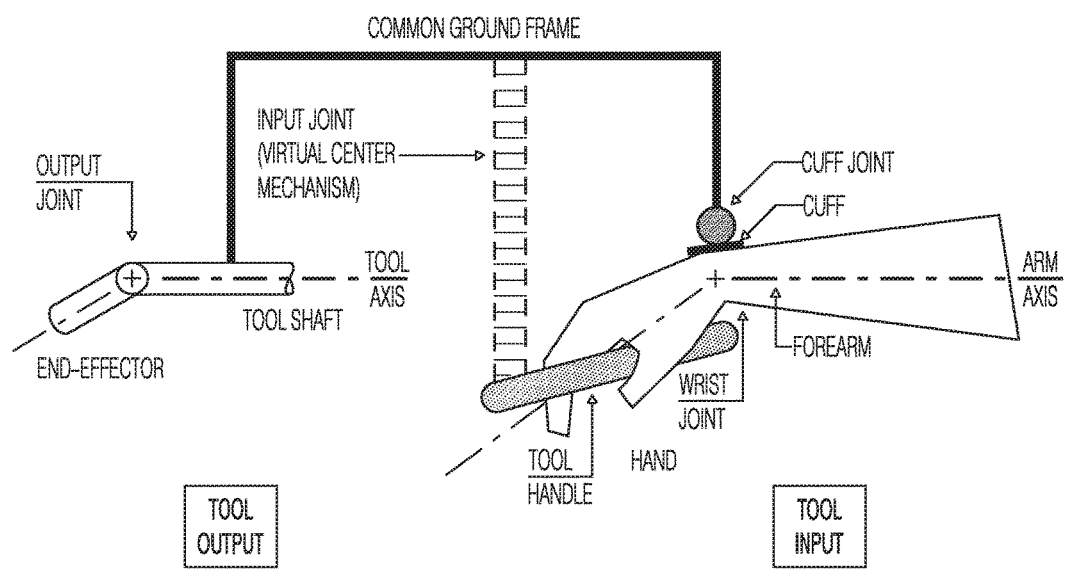

For example, compare FIG. 16 (generically describing an attachment mechanism as described herein) with FIG. 1, above. In FIG. 1, the frame is securely and rigidly attached to the forearm by the fore-arm cuff In contrast, in FIG. 16 the frame is connected to the forearm via a coupling joint. The coupling joint is a joint between a cuff (which is securely yet comfortably attached to the forearm) and the frame. The cuff in FIG. 16 is analogous to the forearm cuff/attachment member in FIG. 1. All other structure of the overall remote/minimal access tool and associated functionality and underlying rationale as explained in the prior patent and in the above background remains the same between FIG. 1 and FIG. 16.

Thus, in general, the apparatuses described herein includes a cuff and one or more coupling joint(s) 1601 that has one or more (e.g., between one and four) degrees of freedom, so that a cuff (or, when the cuff is attached to a user's forearm, the forearm connected to the cuff) may move in at least one degree of freedom relative to the frame. Specifically, in some variations, the coupling joint may include a gimbal, pivot, bearing (e.g., slider, rail, track), or any other movable element to allow the cuff (and/or forearm in the cuff) to move in one or more directions (e.g., axis) relative to the track. The coupling joint may prevent transmission of movement in one or more directions, and thereby transmit these movements. In some variations the coupling joint may include an elastic material allowing limited movement of the cuff (and/or forearm) relative to the frame. The examples provided below illustrate various embodiments of cuff apparatuses (that may have one or more degrees of freedom) that may be used with or incorporated into a minimal access tool.

Figure 17:
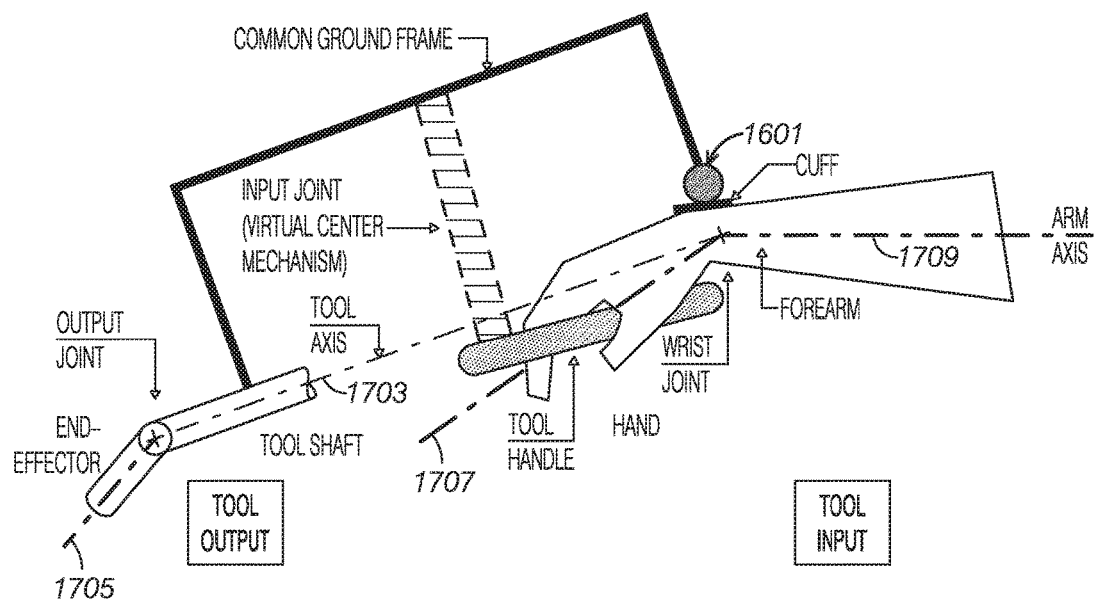

In general, the cuff apparatuses described herein modify how the frame is attached to the forearm, and may overcome the limitations described above. For example, the coupling joints described herein can have up to two rotational degrees of freedom associated with articulation (pitch and yaw). The coupling joint may ensure that these two rotations coincide with the articulation of the user's wrist joint. In other words, the axes of rotation of these two articulating DoF may pass through the user's wrist joint. As shown in FIG. 17 (in a side view), a pitch rotational DoF at the coupling joint 1601 may allow the frame to pitch rotate with respect to the forearm. This in turn allows the tool shaft axis 1703 to be held at an angle with respect to the forearm axis 1709. Thus, the user can orient the tool shaft in a direction required by the application (e.g. a surgical procedure) while keeping his forearm in a comfortable orientation.

Figure 18:
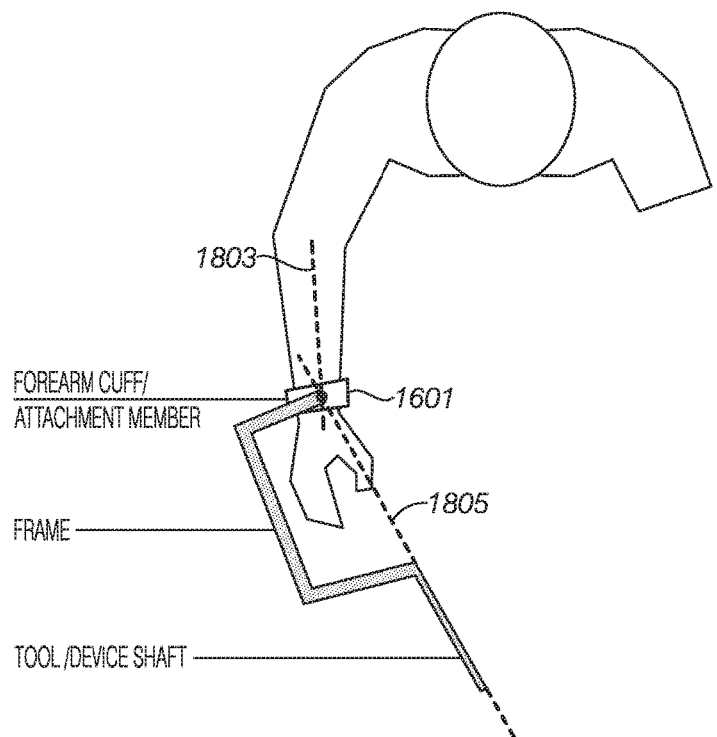

In FIG. 18, in a top view, a yaw rotational DoF at the coupling joint allows the frame to yaw rotate with respect to the forearm. This in turn allows the tool shaft axis 1805 to be held at an angle with respect to the forearm axis 1803. Thus, the user can orient the tool shaft in a direction required by the application (e.g. a surgical procedure) while keeping his forearm in a comfortable orientation.

Furthermore, the coupling joint may additionally have a rotational DoF about an axis of the frame (or tool axis or device axis). Consider such a coupling joint in conjunction with a tool input joint (the virtual center, or VC, mechanism) that does not have a similar roll rotational DoF between the handle and the frame. In other words, the input joint transmits the roll rotational DoF from the handle to the frame. When such a device is interfaced with a user, i.e., the frame of the device is connected to the forearm via the coupling joint, and the user's hand holds or interfaces with the handle, then for any given orientation of the user's wrist (nominal or articulated) and position and orientation of the forearm (nominal or displaced), if the user twirls his fingers without producing any other motion, then this twirl is transmitted from the handle to the frame via the input joint. Since the frame has a roll DoF with respect to the cuff, which in turn is attached to the forearm, the frame exhibits a roll rotation about a frame axis with respect to the forearm.

This arrangement may provide for a significant amount of roll rotation (up to 360 degrees, i.e. a full rotation) about the tool axis. This roll rotation comes from two sources or has two components. First, since the cuff is attached to the forearm, any pronation and supination of the forearm produces roll rotation at the cuff. Even though the frame has a roll rotation DoF with respect to the cuff, the frame moves along with the cuff due to friction at the coupling joint. Second, as the user reaches the limit of his pronation/supination, he can continue to roll the frame about the tool axis via simply twirling his fingers. Now the frame rolls about the tool/device/frame axis with respect to the cuff.

During use, the user may choose to employ either one or both (in any preferred combination) components of roll to achieve the desired application objective (e.g. in a surgical procedure). Since both components of roll happen at the tool frame, these are directly transmitted and exhibited as roll rotation about a tool axis at the end-effector at the tool shaft distal end.

It is important to note that this desired enhanced roll functionality is produced via the specific combination of a roll DoF between the frame and the cuff and a roll constraint (i.e., the ability to transmit) between the handle and the frame.

Similarly, the coupling joint may additionally have a translational DoF along an axis of the frame (or tool axis or device axis). Consider such a coupling joint in conjunction with a tool input joint (the VC mechanism) that does not have a similar translational DoF between the handle and the frame. In other words, the input joint transmits the translational DoF along the tool axis from the handle to the frame. When such a device is interfaced with a user, i.e. the frame of the device is connected to the forearm via the coupling joint, and the user's hand holds or interfaces with the handle, then for any given orientation of the user's wrist (nominal or articulated) and position and orientation of the forearm (nominal or displaced), if the user pecks with his fingers without producing any other motion, then this pecking motion is transmitted from the handle to the frame via the input joint. Since the frame has a translational DoF with respect to the cuff, which in turn is attached to the forearm, the frame exhibits a translational motion along the frame axis with respect to the forearm.

This arrangement provides for an additional amount of axial translation along the tool axis. This axial translation comes from two sources or has two components. First, since the cuff is attached to the forearm, any in and out motion of the forearm (direction 1 in FIG. 5) produces axial translation at the cuff (since the cuff is secured to the forearm). Even though the frame has a translational DoF with respect to the cuff, the frame moves along with the cuff due to friction at the coupling joint. Second, in addition to moving his forearm in and out, the user can continue to axially translate the frame along the tool axis simply via pecking with his fingers while holding the handle. Now the frame axially translates along the tool/device/frame axis with respect to the cuff.

During use, the user may choose to employ either one or both (in any preferred combination) components of axial translation to achieve the desired application objective (e.g. in a surgical procedure). Since both components of axial translation happen at the tool frame, these are directly transmitted and exhibited as axial translation along a tool axis at the end-effector at the tool shaft distal end.

It is important to note that this desired enhanced axial translation functionality is produced via the specific combination of a translational DoF between the frame and the cuff and an axial translation constraint (i.e. the ability to transmit) between the handle and the frame.

Figure 56:
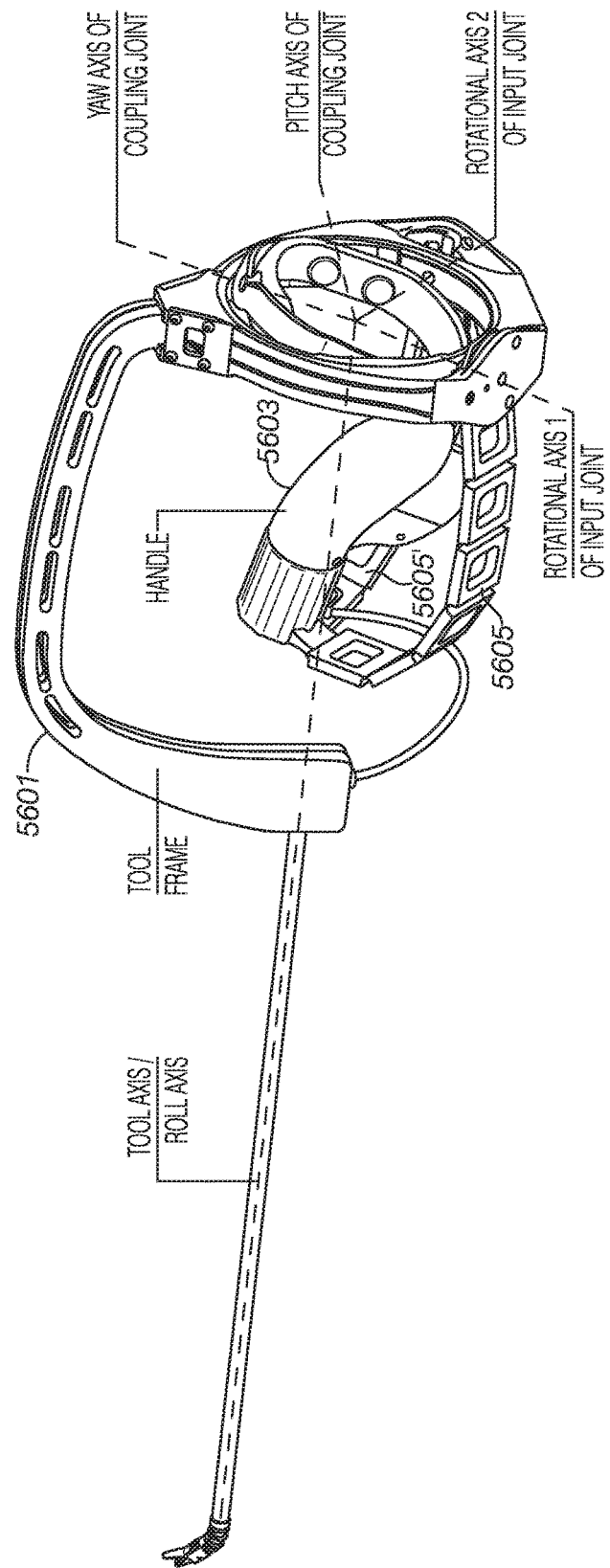
FIG. 56 illustrates one variation of a minimal access device having including a body (e.g., forearm) attachment assembly between the cuff configured to hold an arm and a frame including (or attached to) an elongate tool shaft having a tool axis. This device also includes a parallel kinematic 2 DoF input joint. The axes of rotation of the forearm attachment assembly (a yaw axis of the coupling joint and a pitch axis of the coupling joint, as well as a roll axis of the tool shaft) all intersect at a point of intersection within the user's wrist or forearm; the two axes of rotation of the parallel kinematic input joint also intersect at this same point.

It is necessary to observe that there is a distinct difference between the input joint (i.e., which may be a virtual center mechanism) and the coupling joint(s) of the forearm attachment assemblies described herein, although the two may be desirably used together. The axes of pitch and yaw rotations provided by the input joint are made to be coincident with the user's wrist joint via a virtual center mechanism. The axes of two rotations (pitch and yaw) enabled by the forearm attachment assembly i.e. the coupling joint may also be coincident with the user's wrist joint. This is illustrated, for example, in FIG. 56. In this example, the virtual center mechanism of the parallel kinematic apparatus shown is necessary to drive the output joint (i.e. the end-effector articulating in the pitch and yaw rotational directions with respect to the tool shaft) as the user hand rotates about the user wrist joint with respect to the user forearm to provide input articulation in the pitch and yaw directions. The input joint is a connection between the handle and the frame while the coupling joint is a connection between the cuff and the frame. Both joints share the frame as a common reference ground.

In this example, the parallel kinematic input joint has two degrees of freedom (pitch and yaw) and includes two independent paths for transmission of motion coupling the handle 5603 to the tool frame 5601, wherein the at least two independent paths 5605, 5605' comprise a first path and a second path. A first intermediate body may be present in the first path that is connected to the tool frame by a first connector and to the handle by a third connector; and a second intermediate body is in the second path that is connected to the frame by a second connector and to the handle by a fourth connector; wherein the first connector and the fourth connector both allow rotation in a first rotational direction and restrict rotation in a second rotational direction. Further wherein the second and third connectors allow rotation in the second rotational direction and restrict rotation in the first rotational direction.

In this example, because the VC mechanism allows for 2 DoF about two orthogonal axes input, the third axis of rotation (i.e. roll) is constrained and permitted to drive rotation of the end effector about the tool shaft axis. The rotation of the tool shaft is a direct result of the VC mechanism's ability to rotate the tool frame about the same axis. The coupling joint of the forearm apparatus enables this attribute by decoupling the forearm axis from the tool frame axis and allowing the hand to rotate the tool handle driving the tool shaft and frame about a known tool/frame axis. For this reason, the input joint and the coupling joint share the same common ground, i.e., the tool frame, and are separate entities albeit symbiotic when considering overall device function. Another critical design aspect related to the coupling joint is, not only the coincidence of the pitch and yaw axes of the input joint and the coupling joint with each other and with respect to the user's wrist joint, but also the concentricity of the axis of the roll DoF of coupling joint with respect to the frame/tool axis of the device. This specific feature is critical to enable consistent and predictable roll rotation about this axis so that the end effector can be manipulated as desired by the surgeon. When these axes are not concentric, but eccentric, one axis revolves about the other and results in an unpredictable "lurching" of the tool shaft and end effector.

Summarizing the two points above, in general, the device can have a coupling joint that provides any combination of these four DoF (two articulating rotational DoF (pitch and yaw) centered at the user's wrist joint, rotational roll DoF about a tool/device axis, an axial translational DoF along a device/tool axis). Any motions that are not provided as a DoF are constrained. For example, if all these four DoF are provided then the two translational DoF at the forearm (indicated by directions 2 and 3 in FIG. 5) are constrained and therefore transmitted from the forearm to the frame via the coupling joint. The overall rationale of a one to one mapping of the user's input motions to corresponding output motions at the device end-effector (tool output) is maintained and achieved more effectively.

Any DoF or motion that is provided at the wrist joint may be achieved via very well defined joints (e.g. pivots, pins, slides, slots, etc.) or may be provided simply via a lack of constraint using some soft/elastic attachment (e.g. bands, stretchy Velcro, etc.).

Various embodiments of the coupling joint are described below, with different combinations of DoFs shown and various ways of achieving these DoF.

Embodiment 1

FIG. 19 shows a three axis gimbal (3 DoF), and FIG. 20 shows a spherical roller bearing (3 DoF) that may be used with this variation.

The forearm attachment assembly as previously described comprises a frame, a connection mechanism, and a cuff. One embodiment that offers 3 DoF is shown above. The apparatus interfaces the frame at the instrument interface (10) and makes a secure rigid attachment to the frame. Within the apparatus, rotation of the forearm about the arm axis and rotation about the hand axis are enabled by the rotation axis (12). This is accomplished in one embodiment but not limited to a keyed track system where one surface slides across another with minimal resistance and is confined by the keying system, in this case a T-slot, to this one axis of rotation. Within the apparatus, the axes identified by (14) and (16) are analogous to the two axes of the wrist itself. These axes offer unhindered rotation during wrist flexion/extension (14) as well as wrist deviation (16). This is accomplished in one embodiment but not limited to concentric rings that are pinned along the axis for which they permit rotation. The innermost ring is identified as the cuff which serves as the semi-rigid interface between the user's forearm and the connection mechanism. The cuff is intended to be comfortable to wear and offer a secure fit for varying wrist sizes. Through a compression or tethering system, the cuff is intended to temporarily retain the user's forearm when the user desires to control the steerable device and transmit input through the connection mechanism and virtual center mechanism.

As it relates to minimal access tools, the apparatus with 3 DoF enables the user to be translationally constrained to the common ground at the ground reference established at the wrist joint and unconstrained in all degrees of rotation. This newly established ground reference at the wrist joint allows the user to apply forces to the tool handle and control movements of the end-effector independent of the frame. The ground reference of the wrist joint allows the user to leverage the handle against the ground held constant by the forearm when applying motion forces for input. The internal force feedback loop created between the handle, and forearm is advantageous for any of the minimal access tool devices because it reduces or eliminates forces that may have previously been transmitted from the frame to an external ground such as the trocar cannula and ultimately the patient. By reducing these forces the device may offer less trauma to the patient during particularly suture-intensive MIS procedures.

Embodiment 2

FIG. 21A shows a generic minimal access tool having a frame 2101 including an elongate tool shaft 2100 with a tool axis 2102. A cuff 2108 is formed as part of an inner gimbal 2106. The inner gimbal 2106 and an outer gimbal 2104 and a bearing (shown as a plain bearing configured as a slide 2112) are connected between the frame 2101 and the cuff 2106. In this example, the inner gimbal forms the seat of the cuff and is pivotably connected through a pair of pins to the outer gimbal. The outer gimbal is pivotably connected through a pair of pins to the bearing (slide 2112) and the bearing slides in a track formed by the frame to allow roll rotation. Alternatively a different type of bearing, such as the roll bearing of FIG. 20 may be used. Thus, the body (e.g., forearm) attachment in this example is configured for pitch, yaw and roll DoF, and is arranged so that the roll axis is the same as the tool axis. The tool axis (roll axis), pitch axis of rotation and the yaw axis of rotation all intersect at a point within the opening formed in the cuff to hold the user's wrist or forearm.

Figure 21B:
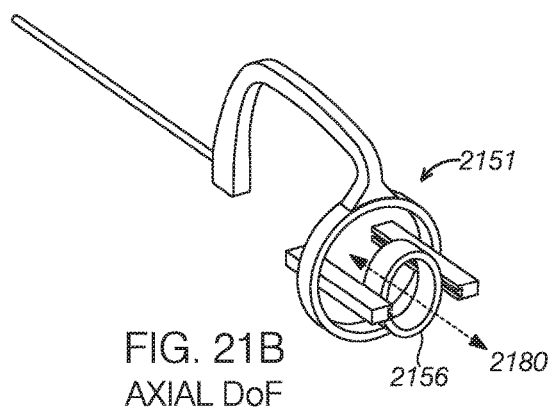
FIGS. 21B-21G schematically illustrate six different degrees of freedom between a generic cuff and a frame.
Figure 21C:
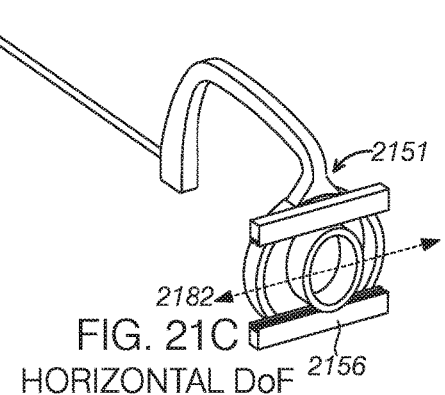
Figure 21D:
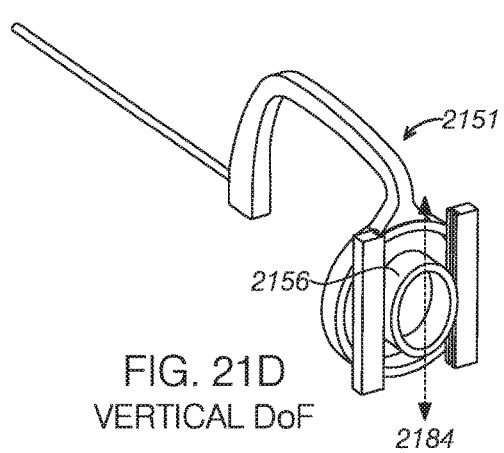
Figure 21E:
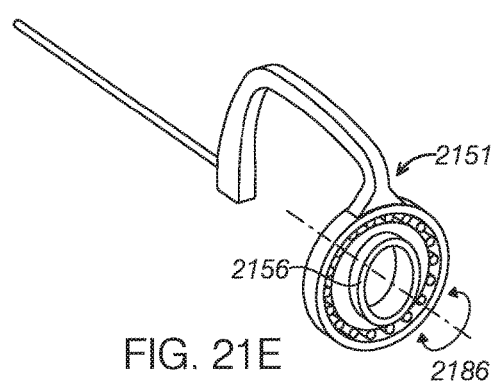
Figure 21F:
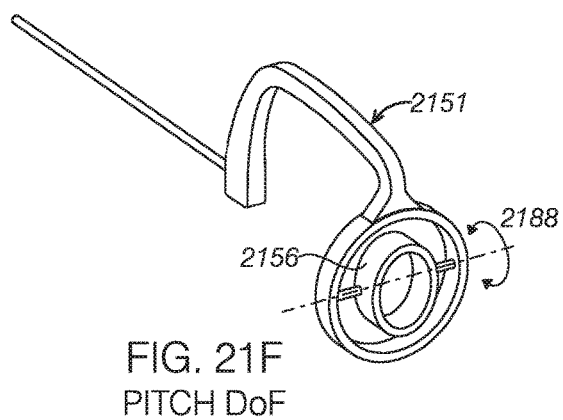
Figure 21G:
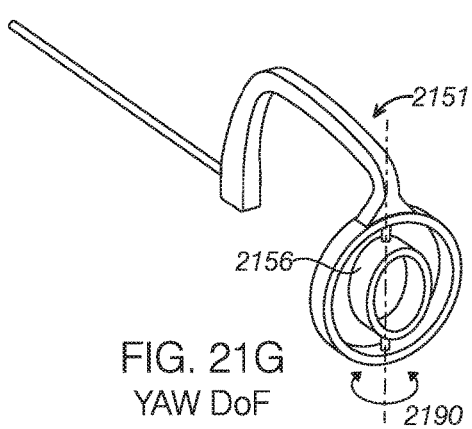

FIGS. 21B-21G generically illustrate degrees of freedom between a cuff 2156 and a frame 2151. There are six total degrees of freedom in this example, three translational, and three rotational. FIG. 21B shows axial translation 2180 between the cuff 2156 and the frame 2151. FIG. 21C shows horizontal translation 2182 between the cuff 2156 and the frame 2151. FIG. 21D shows axial translation 2184 between the cuff 2156 and the frame 2151. FIG. 21E shows a roll rotation 2186 between the cuff 2156 and the frame 2151. FIG. 21F shows a pitch roll rotation 2188 between the cuff 2156 and the frame 2151. FIG. 21G shows a yaw rotation 2190 between the cuff 2156 and the frame 2151.

Embodiment 3

Figure 22:
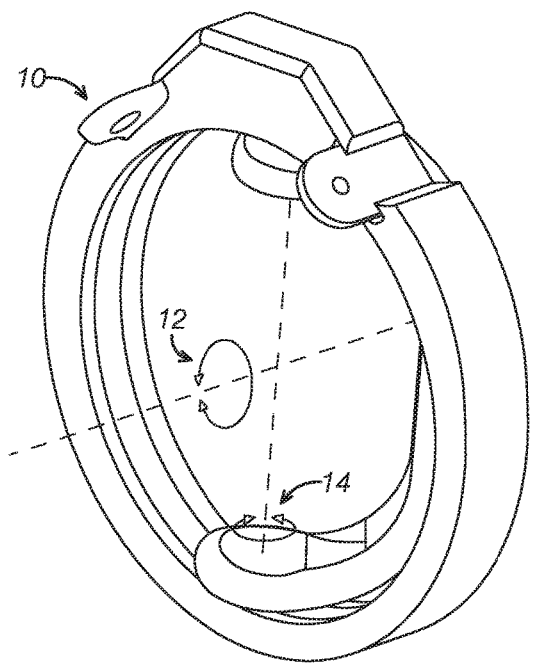
FIGS. 22, 23, 24A-24B, 25, 26, 27, 28, and 29 all illustrate another example of a minimal access tool including a forearm attachment assembly that may be used with a minimal access tool.
Figure 23:
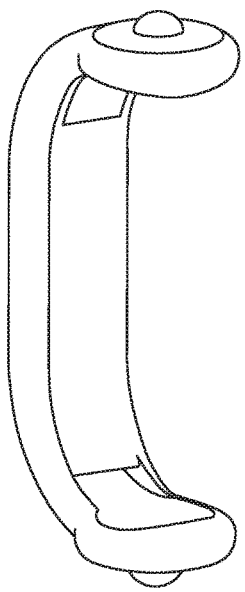

The forearm attachment assembly shown in FIGS. 22 and 23 offers 2 DoF and is similar to the device previously described in Embodiment 2, however it does not enable the deviation rotation of the wrist (16). In this embodiment, a keyed track system is also present however it utilizes a ball-in-track system where the 2 DoF occur at the same instance as opposed to the stacking of concentric rings in the previous example. This loss of one DoF is not necessarily a detriment to the device but it does restrict some motion that the user may require. To limit one DoF does not mean that this axis, the deviation rotation, could be the only axis to be constrained. As it applies to the minimal access tool device described herein, the rotation typically occurring about the deviation axis is minimal, approximately 5-10 degrees. When this axis is constrained the device can be manipulated in space and fully supported by one hand. This is advantageous because surgeons may choose to introduce and remove the tool shaft from the trocar cannula without support (grounding) from their other hand. This is not as easily accomplished with the device previously described (3 DoF apparatus) as the tool frame can fall about this axis until it is grounded by a second point along the tool shaft either by the trocar cannula or the surgeon's opposite hand.

In this embodiment, the cuff is a semi-rigid body that comfortably and securely mounts to the wrist through a tethering system such as Velcro straps or wrist watchband style closure. The cuff maintains the location of the axes of rotation and the wrist center with respect to the forearm, wrist joint, and hand. The cuff enables the user to "snap" in to the ring or track system where the two balls, located at opposite ends of the axis as it runs through the wrist, act as pins to key the user's wrist to the track and also become the articulating surface of rotation. To disengage the cuff, the user simply overcomes the outward spring force of the semi-rigid cuff to "snap" out of the ring. The outward spring force of the cuff retains the cuff and the user's wrist in place provides the connection mechanism with the attributes previously described.

Figure 24A:
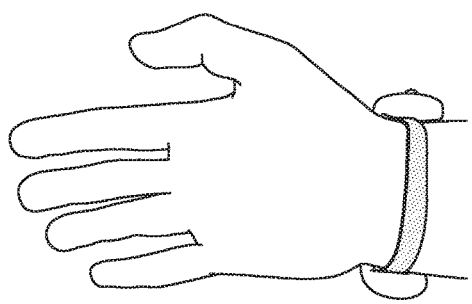
Figure 24B:
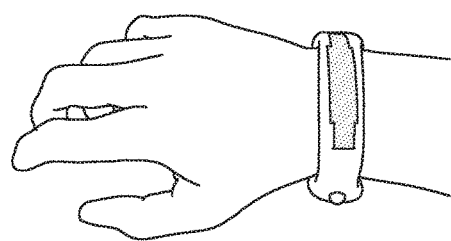
Figure 25:
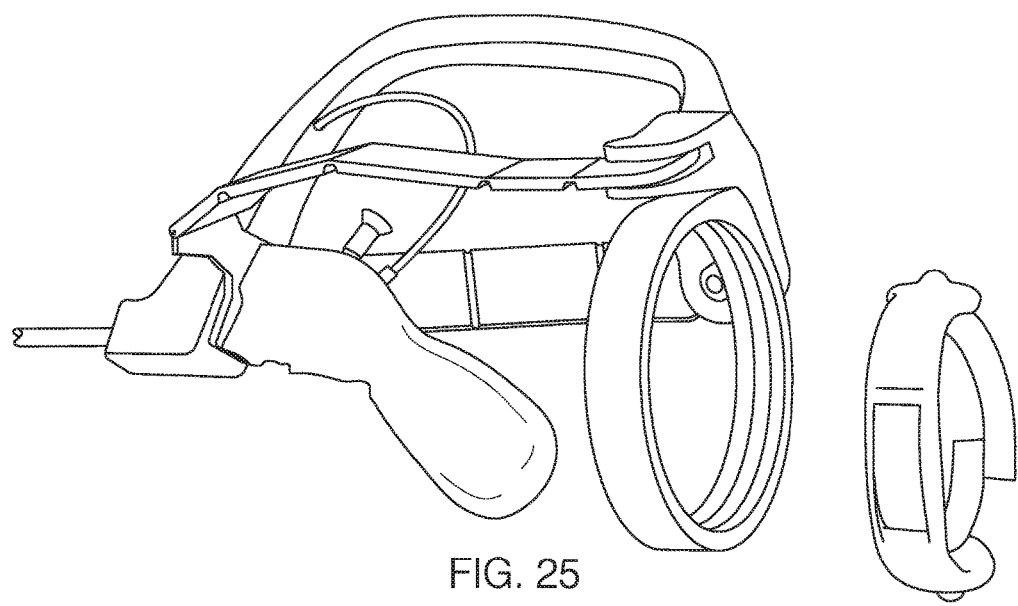
Figure 26:
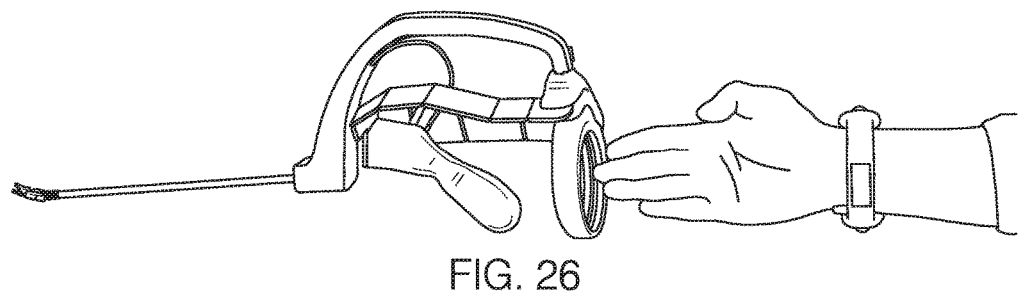
Figure 27:
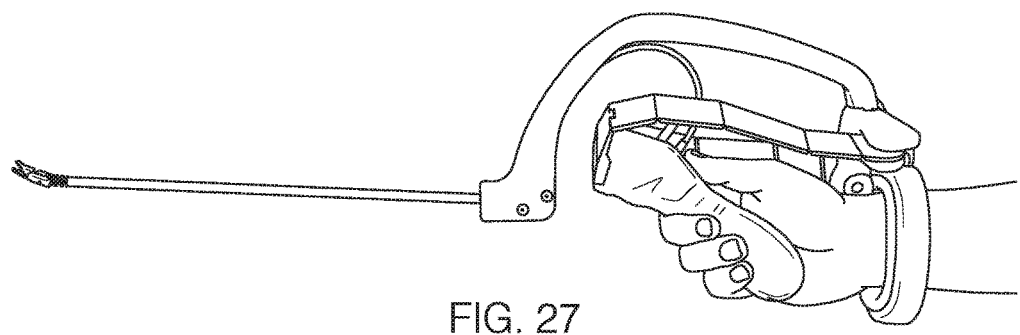
Figure 28:
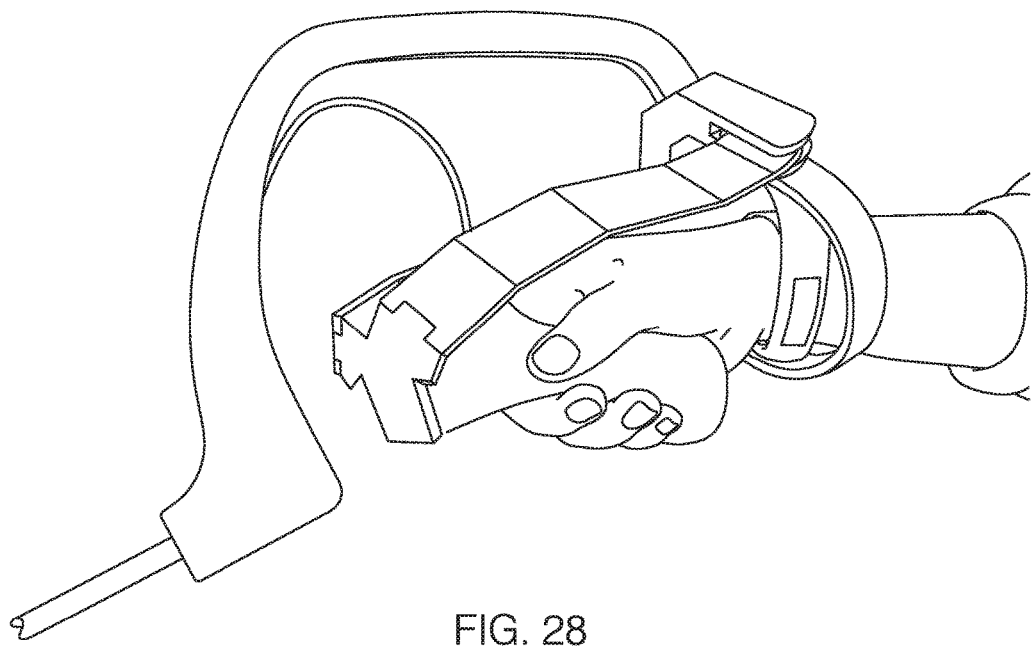
Figure 29:
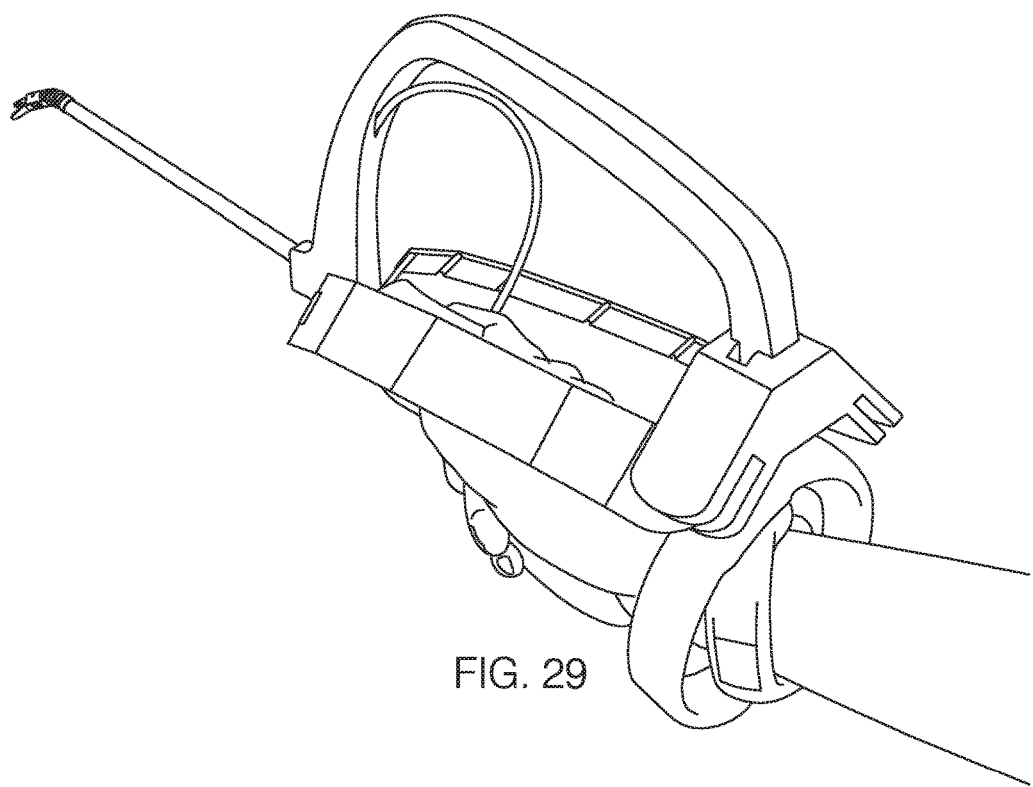

FIGS. 24A and 24B show a wrist cuff installed on the forearm using a Velcro strap. FIG. 25 illustrates the apparatus (including the cuff and coupling joint as described above), with the cuff separate from the frame (and attached ring). FIG. 26 shows the device prior to being interfaced (i.e. mounted/held) with the user. Finally, FIG. 27 shows the device with the cuff installed and interfaced with user. FIG. 28 shows how the coupling joint enables the tool axis to be at a different orientation compared to the forearm axis. FIG. 29 shows how the coupling joint enables the tool axis to be at a different orientation compared to the forearm axis. The coupling joint enables the tool axis to be at a different orientation compared to the forearm axis.

Embodiment 4

Figure 30:
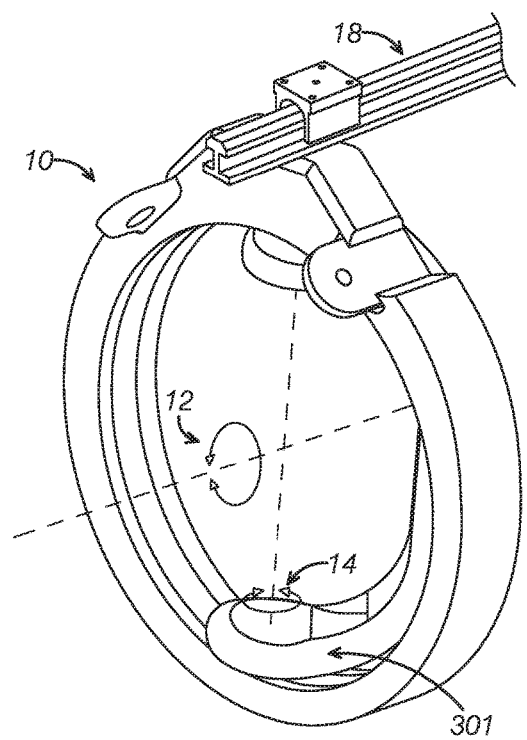
FIG. 30 is another example of a forearm attachment assembly that may be used with a minimal access tool.

FIG. 30 shows a similar variation as embodiment 3, above, but with an additional axial translational DoF provided by the coupling joint as shown in FIG. 30. A linear guide, slot, or bearing (18, in the figure below) provides the axial translation DoF. In this variation the coupling joint 301 is a gimbal that allows rotation in a first axis 14 due to the pair of pins separated by 180 degrees (not visible in FIG. 30). These pins are also configured as bearings that may slide or roll within a track on the frame to provide roll rotation 12 of the hybrid coupling joint. A cuff (not shown) may be formed within the gimbal or it may be attached rigidly to it.

Embodiment 5

Figure 31A:
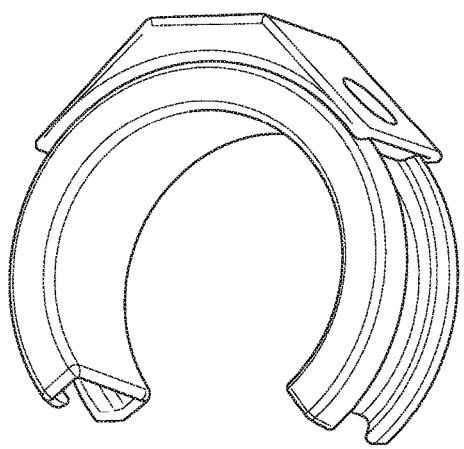
FIGS. 31A-31B is another example of a forearm attachment assembly that may be used with a minimal access tool.
Figure 31B:
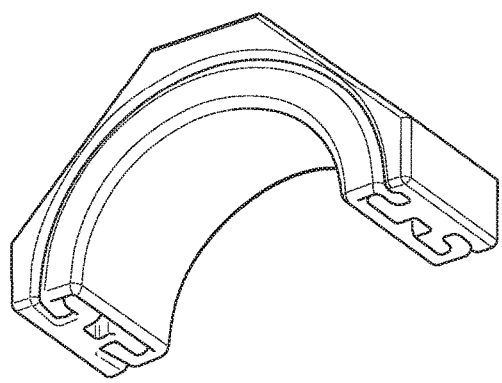

In the variation shown in FIGS. 31A and 31B, the forearm attachment assembly offers one DoF and is similar to the two devices previously described however it does not enable flexion/extension (14) or deviation (16) of the wrist. Limiting to 2 DoF does not mean that these are the only 2 axes to be constrained. This embodiment utilizes a keyed T-slot system where the inner ring slides across the outer ring and confines the rotation about one axis. This option restricts some motion that the user may require.

Embodiment 6

Figure 54A:
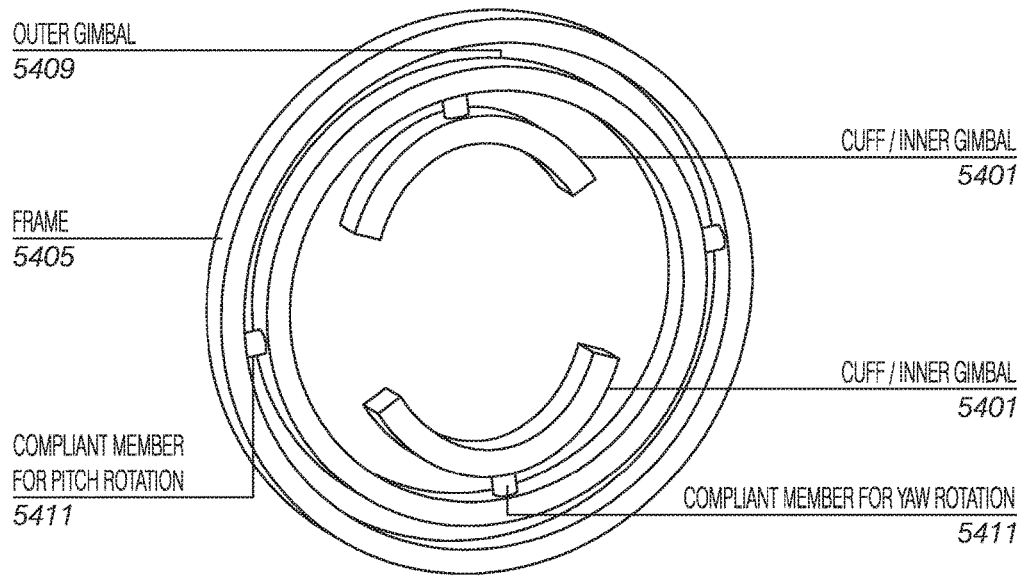
FIGS. 54A and 54B illustrate another variation of a forearm attachment assembly. In this example, the forearm attachment assembly includes a pair of gimbals that are serially connected by a fixed, but compliant member; thus the entire assembly may be formed from a single piece (e.g., by molding, injection molding, etc.). Pivoting about the first and second (e.g., pitch and yaw) axes may be permitted based on the compliance of the connecting regions (tabs).
Figure 54B:
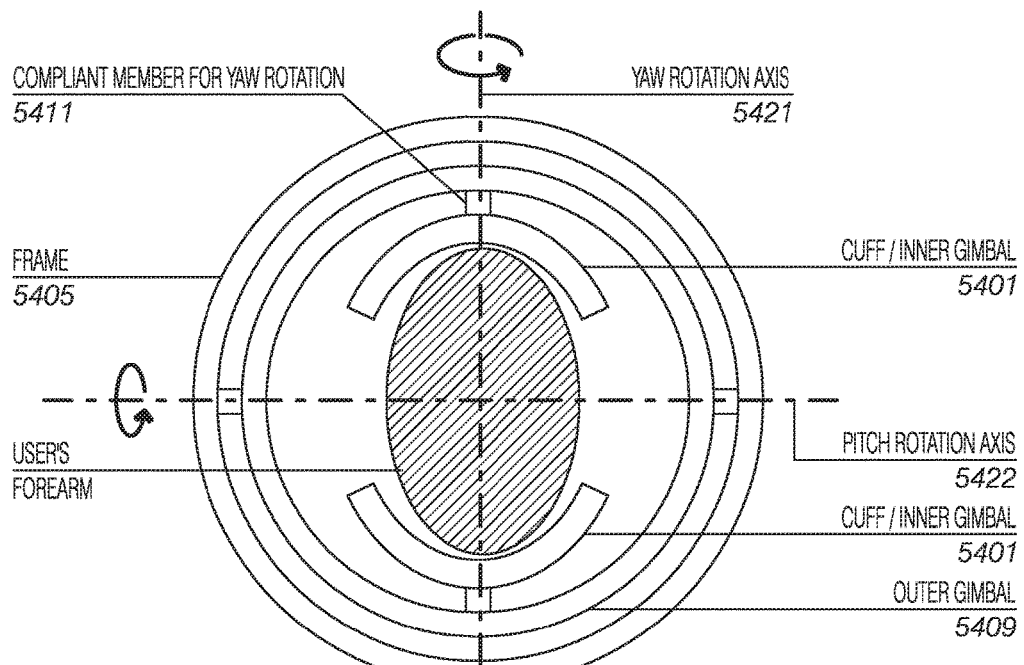
Figure 55:
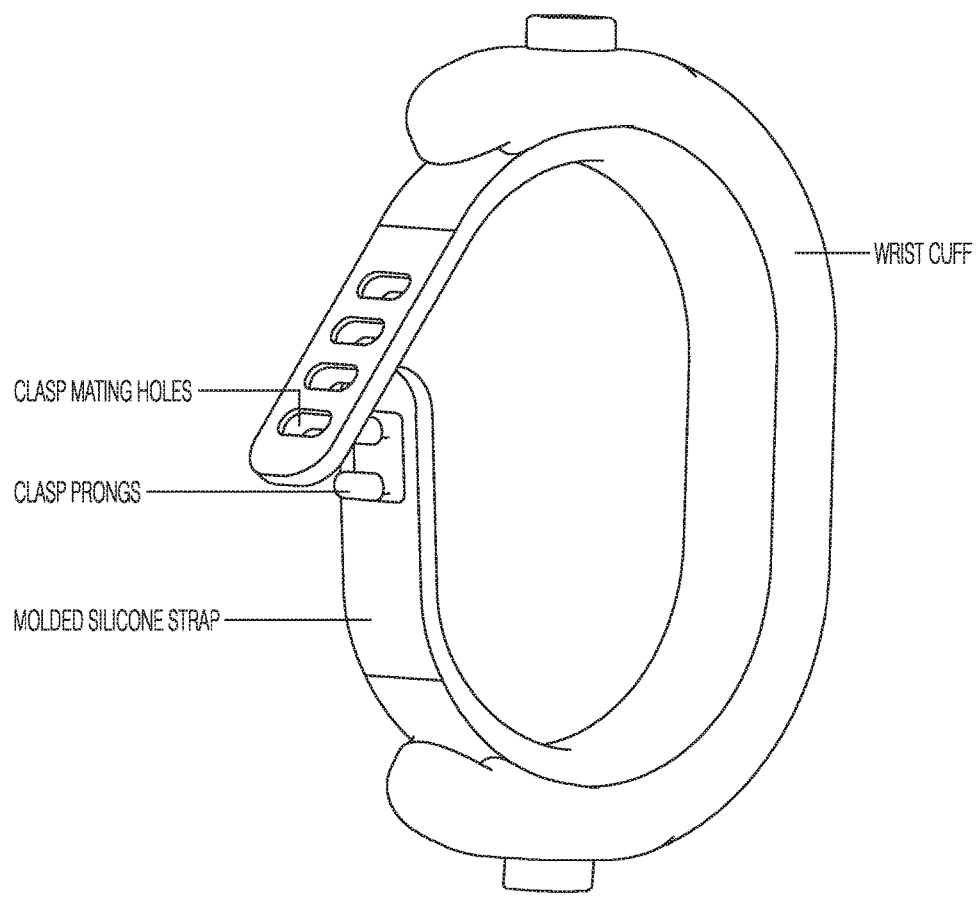
FIG. 55 illustrates another wrist cuff including a securement.

Another example of a forearm attachment assembly (e.g., forearm attachment assembly) is shown in FIGS. 54A-54B, which is configured to allow pitch and yaw rotational movement between a cuff (part of the inner gimbal 5401 in this example) and a frame 5405; a bearing may also be included (e.g., between the cuff and the inner gimbal 5407 or between the frame 5405 and the outer gimbal 5409). In this example, pitch and yaw rotations are enabled for the coupling joint due to the compliance of the connections, tabs 5411, 5413 between cuff and gimbal frame. Since these two rotations need not be continuous, compliant/flexure joints rather than pin joints may be used, as shown.

In FIG. 54B the translation in pitch 5422 and yaw 5421 are shown. This variation of a 2-axis (pitch and yaw) gimbal assembly includes compliant members complying to provide both pitch and yaw rotational degree of freedom. The compliant member between each of cuff/inner gimbal and outer gimbal, and outer gimbal and gimbal frame provide the axis of rotation and realize the design with minimal components. The integral cuff/inner gimbal 5401 and the outer gimbal 5409 are connected by a pair of compliant members 5411 (along the yaw axis between the inner and outer gimbal) providing yaw rotation. Similarly, pair of compliant members 5413 (along the pitch axis) between outer gimbal and gimbal frame provides pitch rotation. These compliant members may be made out of an elastic or plastic or rubbery material which can twist and comply in respective orientations. Based on different design of the compliant members, the pitch rotation axis may be formed by the compliant members between inner gimbal and outer gimbal and the yaw rotation axis may be formed by the compliant members between outer gimbal and gimbal frame.

Figure 32:
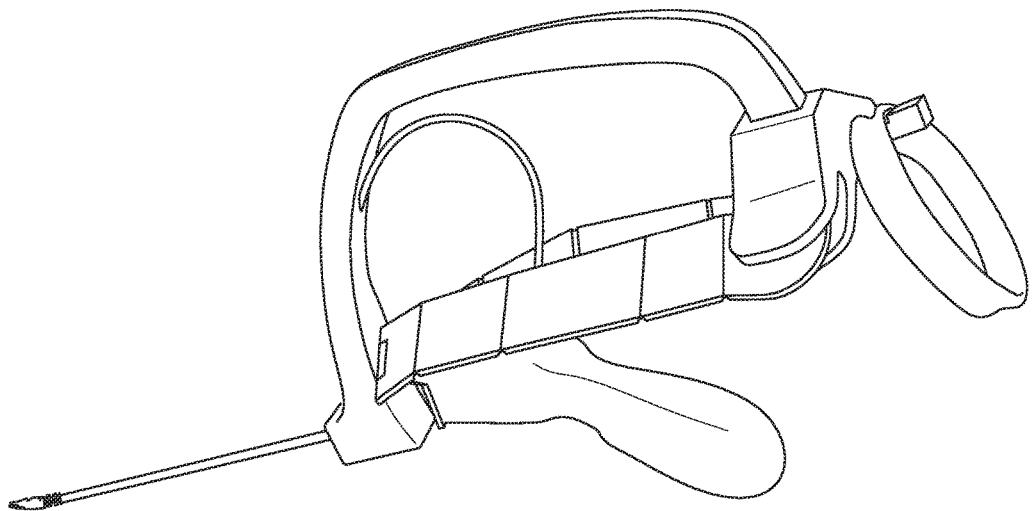
FIGS. 32, 33, 34, 35 and 36 illustrate examples of forearm attachment assemblies that may be used with a minimal access tool.
Figure 33:
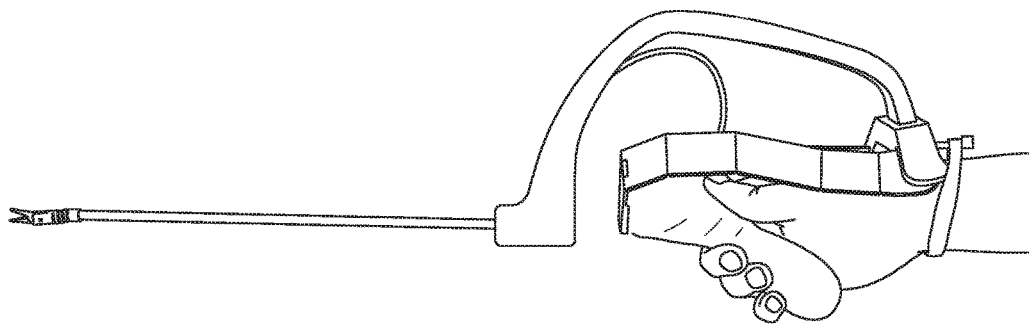

FIGS. 32 and 33 illustrate variations of cuffs that may be considered a single point elastic tether. In this example, the attachment uses a silicone band and offers similar constraints as the single point elastic tether described above.

Figure 34:
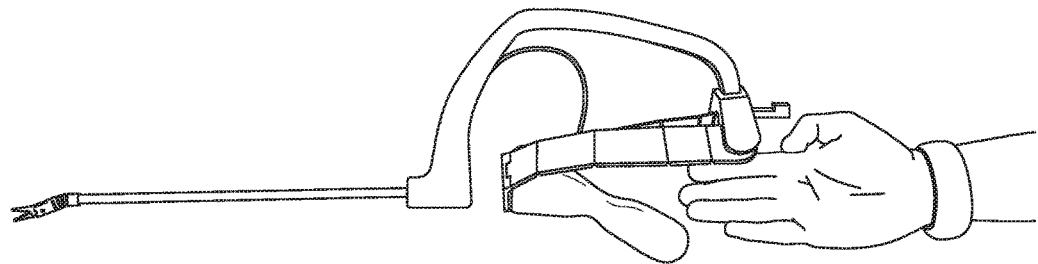
Figure 35:
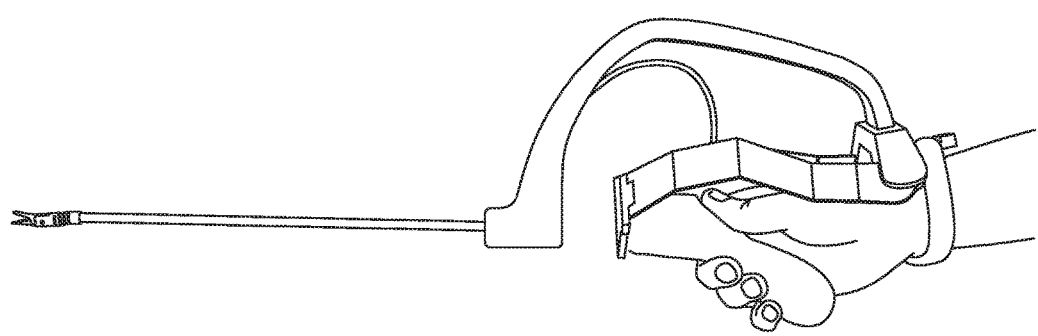

FIGS. 34 and 35 show another example of a single point tether. In this example, the attachment is a Velcro watchband style cuff which applies similar constraints as the single point tethers described above.

Figure 36:
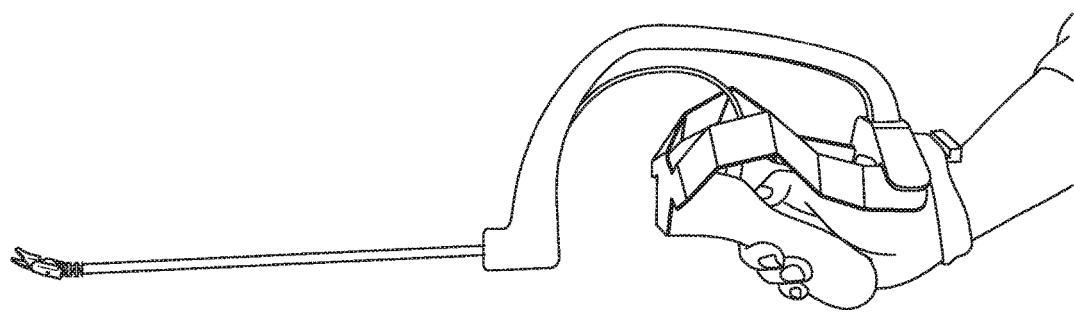

FIG. 36 illustrates how a single point tether based coupling joint may enable the tool axis to be at a different orientation compared to the forearm axis.

Embodiment 7

Figures 37, 38:
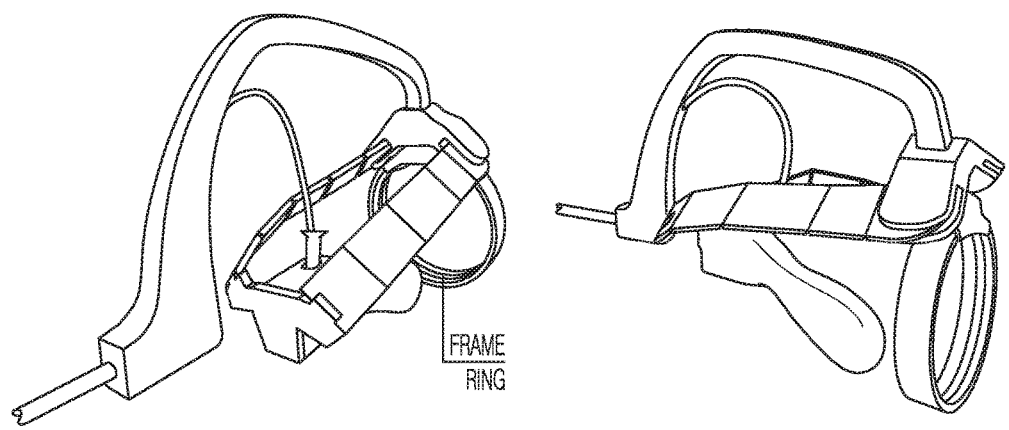
FIGS. 37 and 38 show another example of forearm attachment assembly that may be used with a minimal access tool.

FIGS. 37-38 illustrate another variation. In this embodiment the frame is equipped with a ring that goes around the forearm but does not interface with the forearm via a cuff. This appears to have no joint or connection between the frame and forearm. However, the inside diameter of the ring touches and rides against the periphery of the forearm during use, and can provide the necessary transmission of upward/downward translation and side to side translation between the forearm and the frame. Similarly, the air gap and occasional contact between the forearm and frame allows for the frame to be roll rotated about a frame/device axis with respect to the forearm. The inside diameter of the ring may be padded with an appropriate material to make the interface (when it happens) with the forearm comfortable and minimize any friction during relative sliding between the frame ring and forearm.

Embodiment 8

Another variation may be similar to Embodiment 1 (FIG. 19), above, where the three rotations are produced by a ball and socket joint instead of the three independent rotational joints shown in Embodiment 1. The coupling joint may simply be a ball and socket joint. The limitation of this design would be that it is tricky to get all three axes of rotations associated with the ball and socket joint to be centered at the wrist joint of the user.

Embodiment 9

Figure 39:
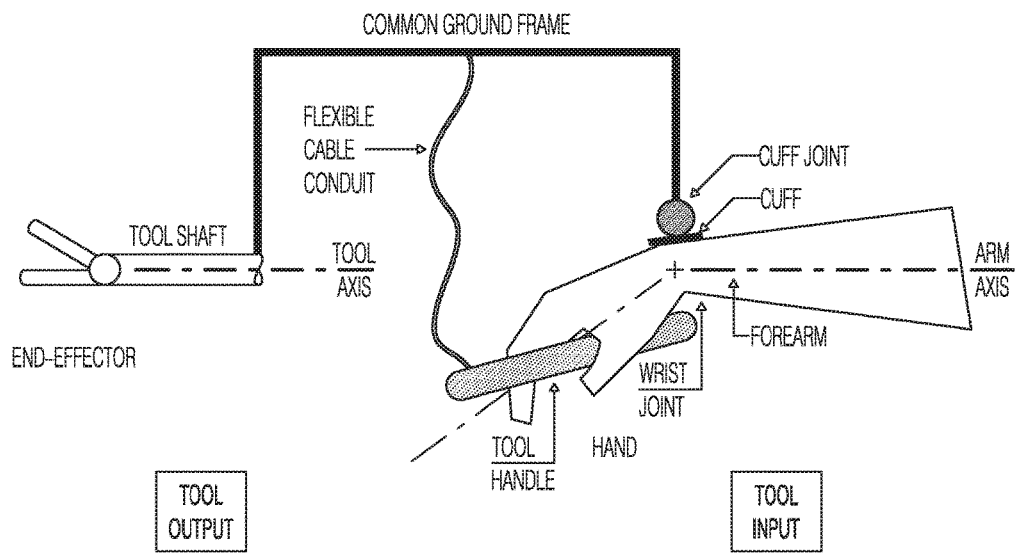
FIG. 39 schematically illustrates an example of forearm attachment assembly that may be used with a minimal access tool.

FIG. 39 illustrates another design, in which the forearm attachment assembly can be relevant to other kinds of minimal access (surgical or other) devices. Consider the basic concept of FIG. 15 and all the associated attributes of the frame, cuff, and coupling joint. The frame can serve as a ground reference for purposes other than what is described for the articulating minimal access device of U.S. Pat. No. 8,668,702.

In FIG. 39, the apparatus includes a handle with a control, such as a switch, button or the like for operating an end effector. In this example, rather consider a device that does not have any articulation (pitch and yaw rotation) at the input joint and only has an open/close motion that has to be transmitted from the user's fingers/thumb to the tool end-effector open/close motion.

In this example, the tool may not include an input joint. Instead, the handle is equipped with a means to produce open/close motion e.g. scissor grip, or pressing a thumb lever, or pressing a finger lever etc. This closure action can be transmitted to the corresponding closure motion of the end-effector via a flexible cable conduit system that goes from the handle to some point on the tool frame or shaft, and then is routed through the frame and shaft to the end-effector. Refer again to FIG. 39.

In a typical non-articulating minimal access device (e.g. a laparoscopic surgical instrument), the tremors associated with the hand are amplified at the end-effector, producing a sub-optimal surgical outcome. In general, natural tremors are greater at the hands/fingers/thumb compared to the forearm. However, with the proposed arrangement, the tool frame is stabilized on the forearm via the forearm attachment assembly, while keep the hands/fingers/thumb free for any other independent action. This ensures lower tremors being transmitted to the end-effector at the distal end of the tool shaft. In this case, one possible independent action of the hands/fingers/thumb can be that of closing a lever at the handle via the thumb/fingers. The fact that the hands/fingers/thumb is connected to the frame via only a flexible cable conduit results in the fact that tremors associated with the hands/fingers/thumb are not transmitted to the frame and therefore the end-effector, for example, see FIGS. 40A-40B.

Figure 40A:
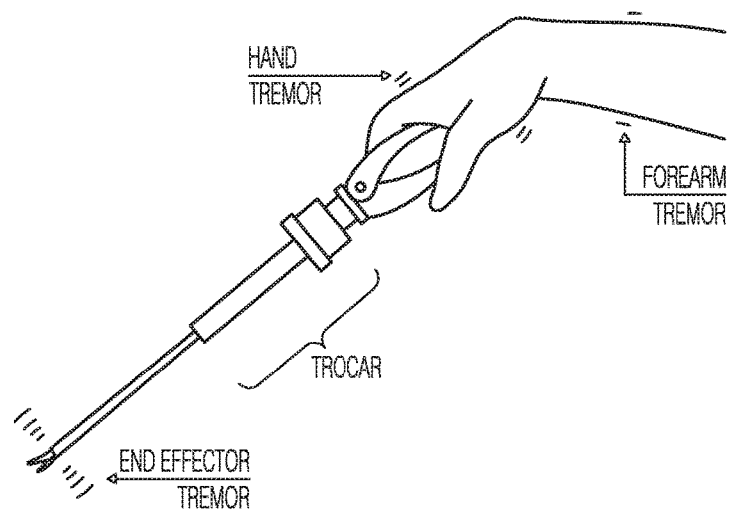
FIGS. 40A-40B illustrate a comparison between the prior art attachment apparatus and the forearm attachment assemblies having one or more degrees of freedom described herein.
Figure 40B:
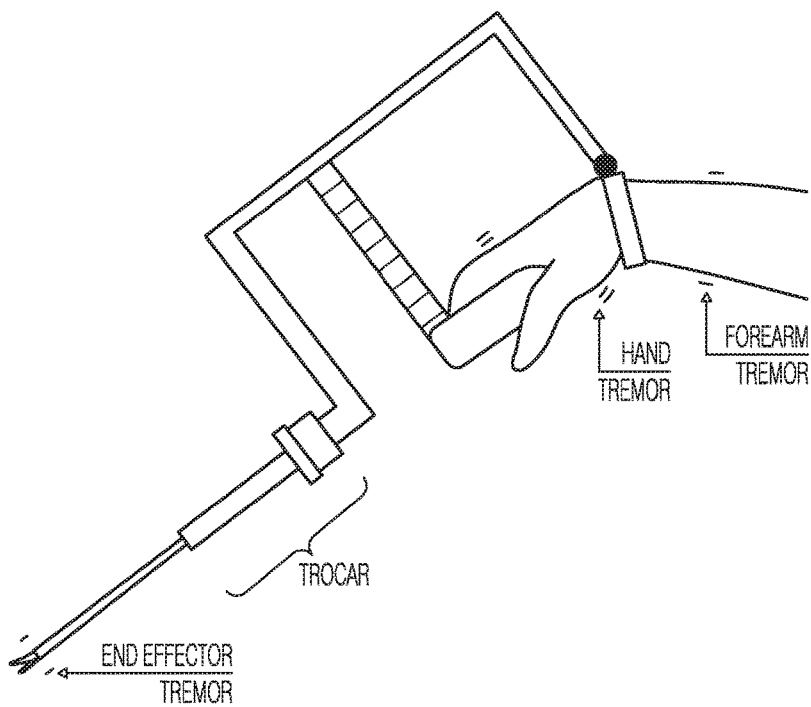

FIG. 40A shows a forearm and hand tremor transmission in a traditional laparoscopic instrument (the number of wiggles/little lines indicate a qualitative magnitude of tremors). FIG. 40B illustrates a forearm and hand tremor transmission in the proposed arrangement (number of wiggles/little lines indicate a qualitative magnitude of tremors). In addition to minimizing the transmission of hand tremors, this arrangement further helps isolate the user's hand movement from the frame, so they do not exert forces on the tool shaft or frame. Many steerable and non-steerable instruments have buttons, levers, triggers or other activation switches that are commonly located on the handle. The user will exert forces to grip the handle and/or activate these switches. In a typical instrument, these forces are transmitted to the entire tool body (shaft and end-effector) and influences the position and movements of the end-effector thereby compromising precision in surgery. The proposed arrangement helps overcome this challenge by isolating or decoupling the motions of the user's hand from that of the tool frame/shaft.

Even though the frame/tool axis and the forearm axis are shown aligned in the above figure, note that as described previously, the coupling joint can have two rotational DoF (pitch and yaw) that will allow the user to orient the frame/tool axis in a direction different from the forearm axis. In this case, since the roll rotation is not transmitted from the handle to the frame (given the absence of an input joint), twirling of fingers will not be transmitted to the frame and therefore to the end-effector.

Embodiment 10

Figure 41:
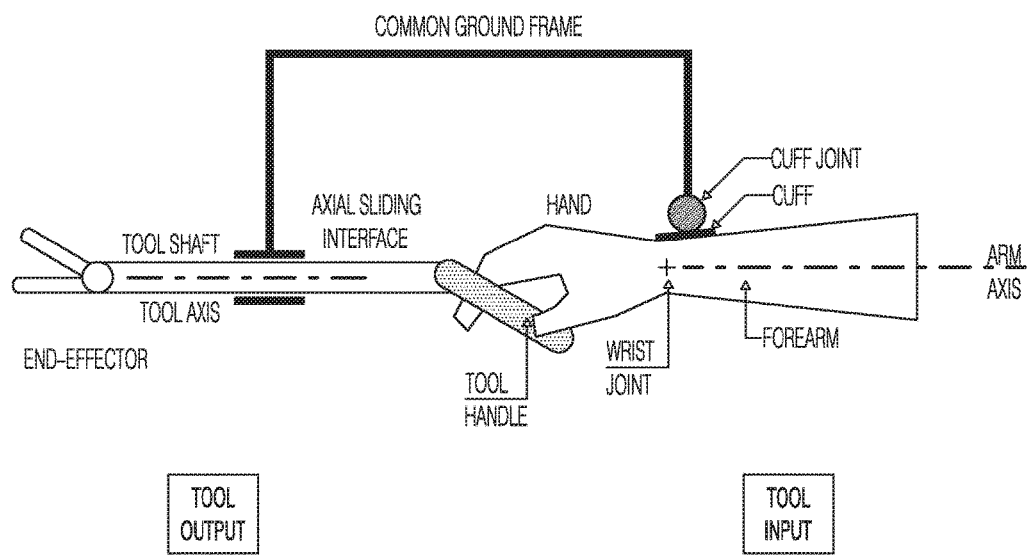
FIG. 41 schematically illustrates another example of a forearm attachment assembly that may be used with a minimal access tool.

FIG. 41 schematically illustrates an embodiment in which the forearm attachment assembly can be relevant to other kinds of minimal access (surgical or other) devices. For example, these devices may not include a tool axis, but may instead hold or support a tool having a tool axis. For example, the frame may include a mount to which a tool may be fit (e.g., a hole, opening, etc.) which may be secured within the mount. Consider the basic concept of FIG. 15 and all the associated attributes of the frame, cuff, and coupling joint. The frame can serve as a ground reference for purposes other than what is described for the articulating minimal access device of U.S. Pat. No. 8,668,702.

Rather consider a device that does not have any articulation (pitch and yaw rotation) at the input joint and only has an open/close motion that has to be transmitted from the user's fingers/thumb to the tool end-effector open/close motion. The tool has a shaft with an axis and a handle that is rigidly connected to the shaft.

Figure 15:
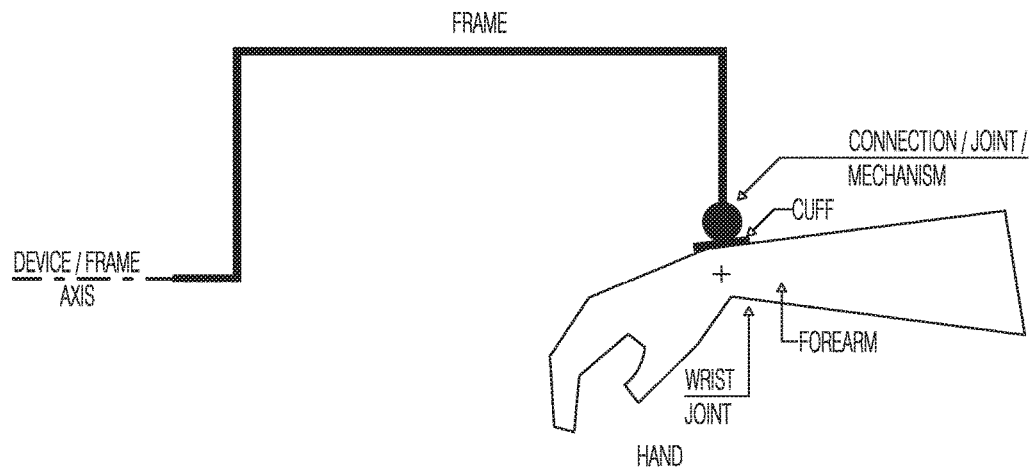
FIGS. 15, 16, 17, and 18 schematically illustrate minimal access tools including a forearm attachment assembly that may allow greater than 1 degree of freedom between the forearm attachment portion (e.g., cuff) and the frame.

The frame of FIG. 15 (which is connected to the fore-arm via the previously described coupling joint) now serves an extended ground support for the tool shaft to help stabilize the tool shaft. Between the frame and the tool shaft, there is an axial sliding joint. This axial sliding joint ensures that the tool axis and the frame axis are aligned with each other and that the tool can translate axially with respect to the frame. This arrangement is different from prior arrangements (e.g. FIG. 16) in the sense that the tool shaft is attached to the handle directly and not to the frame.

Additionally, the handle may be equipped with a means to produce open/close motion e.g. scissor grip, or pressing a thumb lever, or pressing a finger lever etc. This closure action can be transmitted to the corresponding closure motion of the end-effector via a transmission system that goes from the handle to the end-effector via the tool shaft. For example, refer to FIG. 41.

Even though the frame/tool axis and the forearm axis are shown aligned in FIG. 41, note that as described previously, the coupling joint can have two rotational DoF (pitch and yaw) that will allow the user to orient the frame/tool axis in a direction different from the forearm axis. In this case, since the tool shaft is directly connected to the handle, any twirling or pecking motion of the fingers/thumb are directly transmitted to the tool shaft and the end-effector at the distal end of the tool shaft. The coupling joint need not have any additional DoF beyond the pitch and roll rotations.

Figure 42:
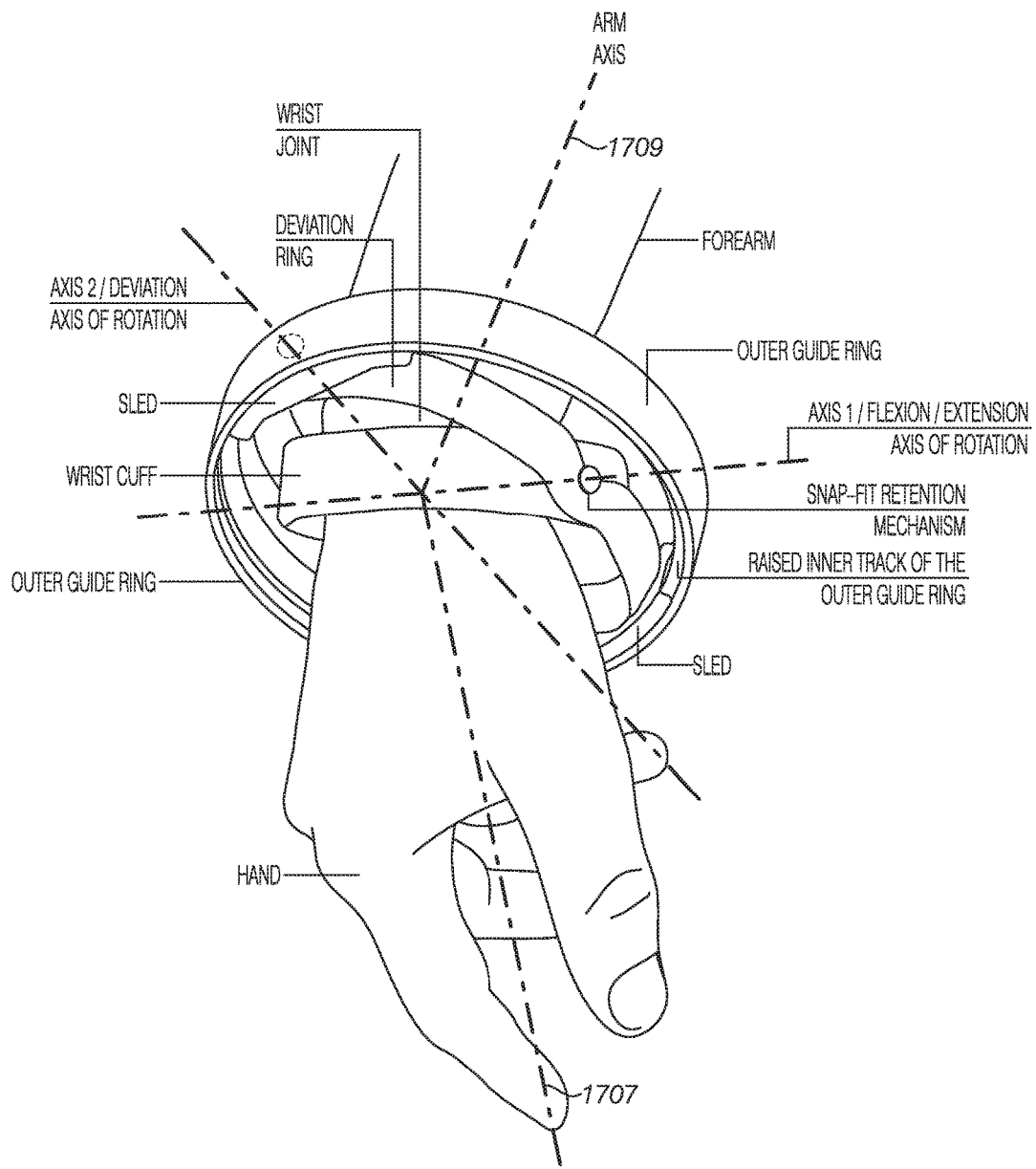
FIG. 42 schematically illustrates one embodiment of the forearm attachment assembly that may be used with a minimal access tool in addition to the user's wrist, forearm, and hand.
Figure 43:
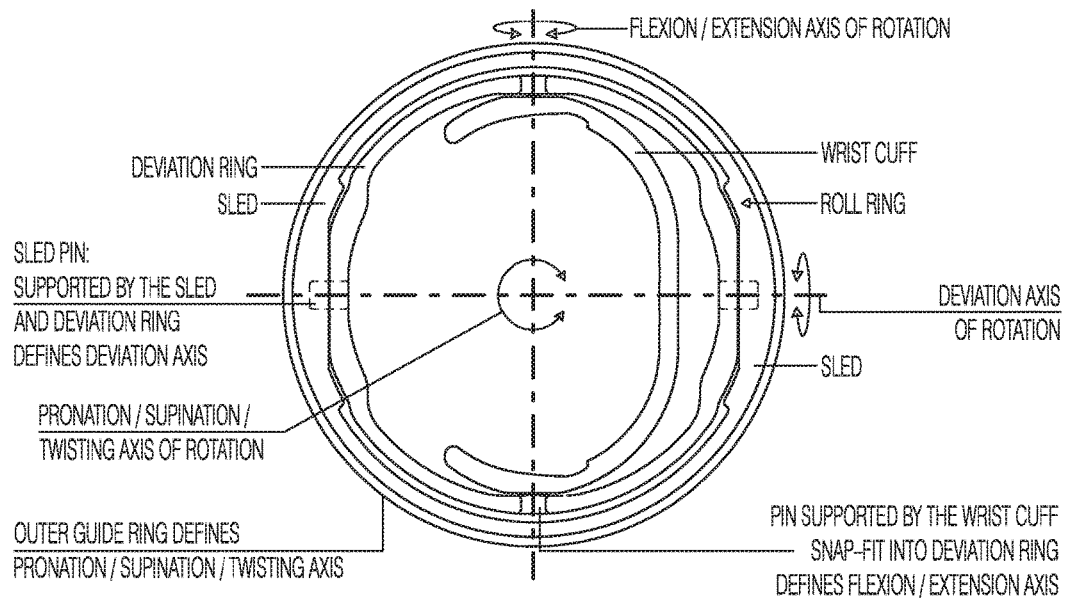
FIG. 43 illustrates the plurality of gimbals, shown as rings, and axes that make up one embodiment of the forearm attachment assembly that may be used with a minimal access tool.

Referring to FIG. 42 and FIG. 43, another embodiment of the forearm attachment assembly, a variation of Embodiment 1, is shown. Much like the apparatus previously described, it provides 3 degrees of freedom (DoF) at the wrist cuff with respect to the common ground (i.e. tool frame). The apparatus can comprise an outer guide ring which is understood to be rigidly affixed to a tool frame. The outer guide ring is a rigid body with a raised inner track which acts as a bearing surface between subsequent rings. The raised track of the outer ring guides and constrains (keys) the subsequent ring which is the roll ring. The raised track of the outer ring further offers a low friction or lubricious bearing surface for uninhibited rotation about the axis defined by the outer ring (Axis 3 in FIG. 44). When this forearm attachment assembly is attached to the forearm of a user, as previously described, the outer ring axis is the same as the tool axis (as shown in FIG. 17) which is the same axis about which the user would drive roll rotation of the frame via pronation, supination, or any twisting occurring at the fingertips.

Figure 44:
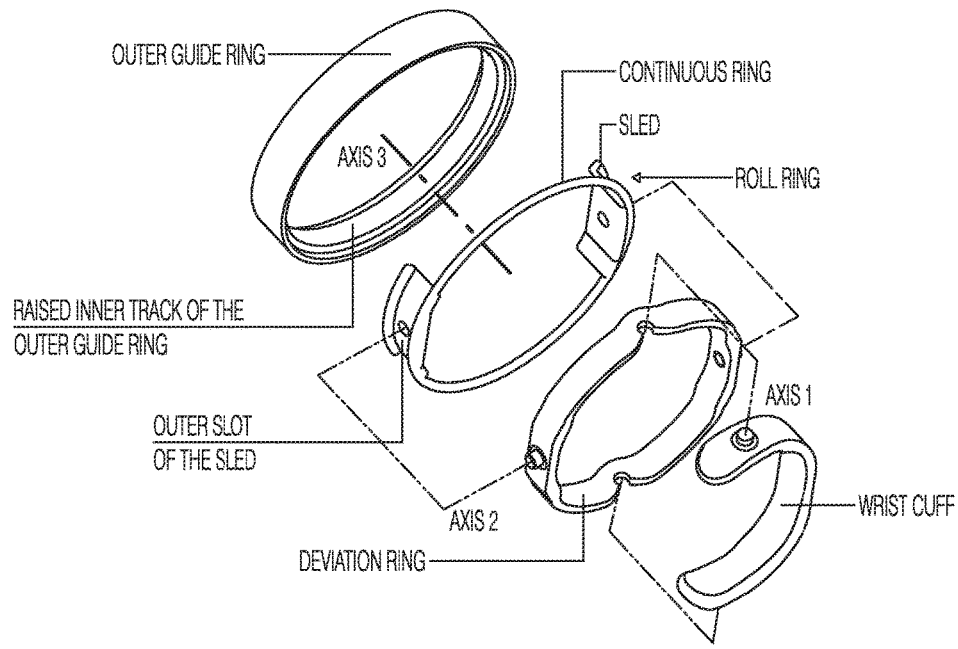
FIG. 44 schematically illustrates the plurality of rings that make up one embodiment of the forearm attachment assembly and the sequence of assembly for the various components that may be used with a minimal access tool.
Figure 48:
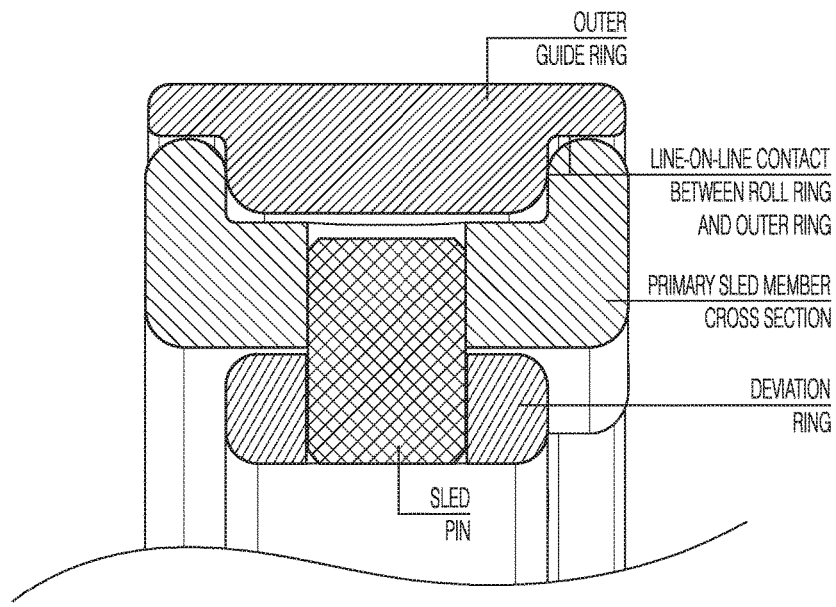
FIG. 48 illustrates a cross-sectional view of one variation of a forearm attach assembly.
Figure 49:
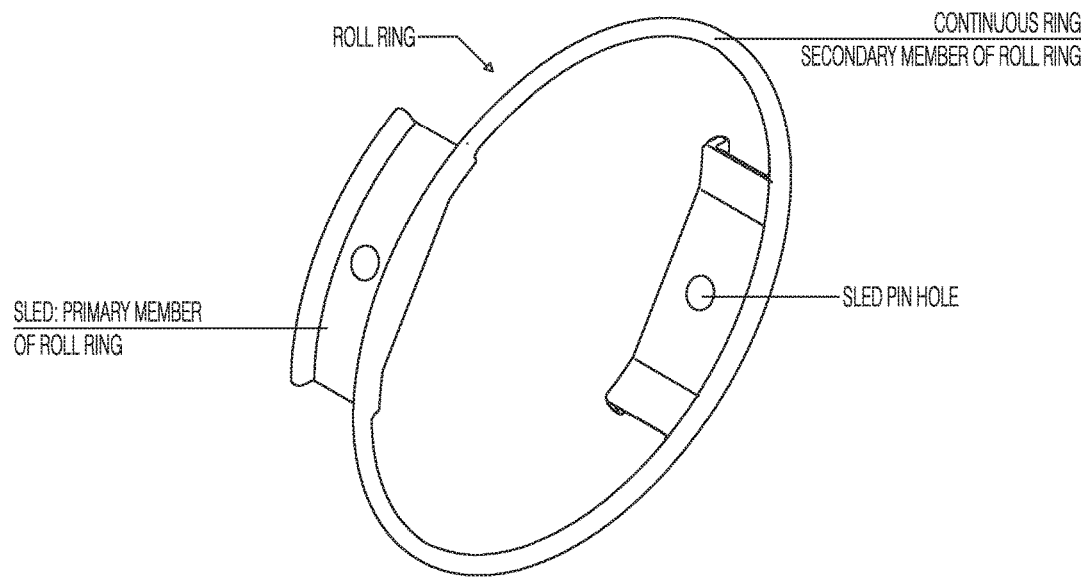
FIG. 49 illustrates the Roll Ring component of the assembly.
Figure 50:
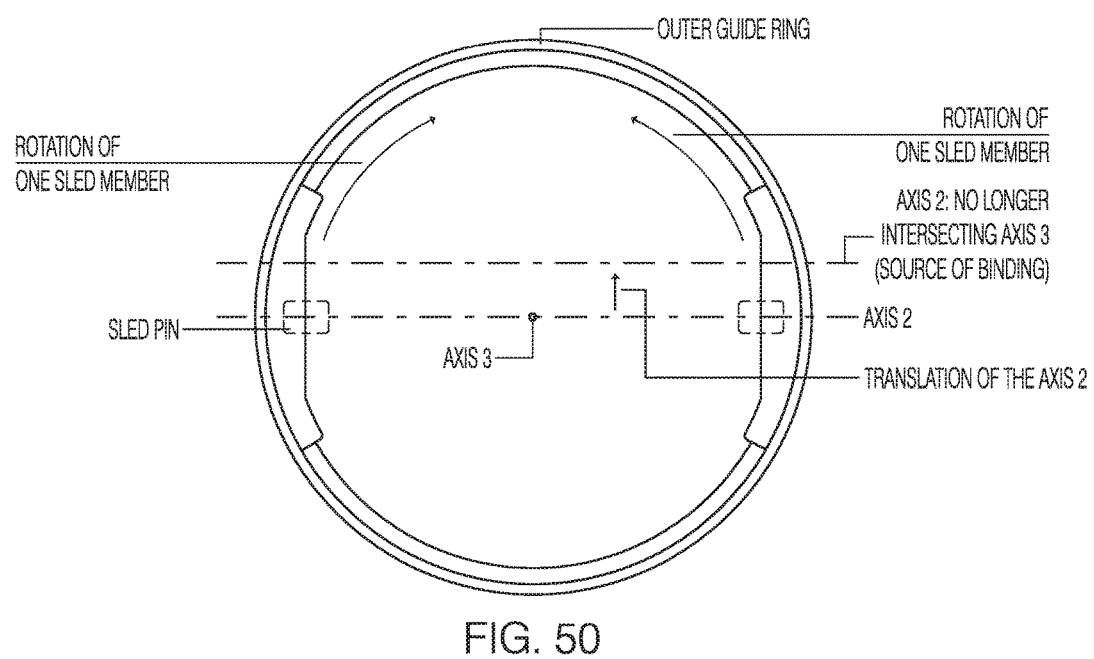
FIG. 50 illustrates the translation of Axis 2 with respect to Axis 3 to demonstrate the source of binding between components.

In one implementation of a bearing, the bearing is a roll ring (See FIG. 49). In this example there can be a slight outward compressive fit between an outer slot of sled on the roll ring and the raised inner track of the outer ring (as shown in FIG. 44). The interface between these two rings is such that only line on line contacts (See FIG. 48) are made where any DoF's are constrained with respect to each ring thus reducing frictional resistances between rings. It is understandable that these contacts might also be surface contacts or multiple point contacts such that frictional resistances are minimized between components. The roll ring (See FIG. 49 and FIG. 44) can comprise one or more primary members (also referred to as sleds) which ride opposite walls of the raised inner track on the outer guide ring. These members contain an outer slot which mates accordingly with the raised inner track of the outer guide ring. Each sled member may support a sled pin (FIG. 48, FIG. 50. FIG. 43) where any given pair of diametrically opposing sled pins define an axis (Axis 2) intersecting the rotational axis (Axis 3) defined by the roll ring rotation about the outer guide ring. As shown in FIG. 43, the roll ring can further comprise a secondary member made up of one or more continuous rings which connect the primary sled members. FIG. 44 shows only one such ring. The continuous ring or rings which support the sleds assist in constraining the sled members to equal rates of rotation about Axis 3 in the same direction (CW or CCW) and prevents any undesirable translation of Axis 2 such that it no longer intersects Axis 3 (See FIG. 50). When the sled members are not connected by a continuous ring there is a possible tendency to rotate and/or translate about Axis 3 at different rates which may cause binding between the outer ring and sled ring. The translation and unequal rate of rotation of the sleds is prevented by the continuous ring since the ring is radially constrained by the outer guide ring.

Figure 45:
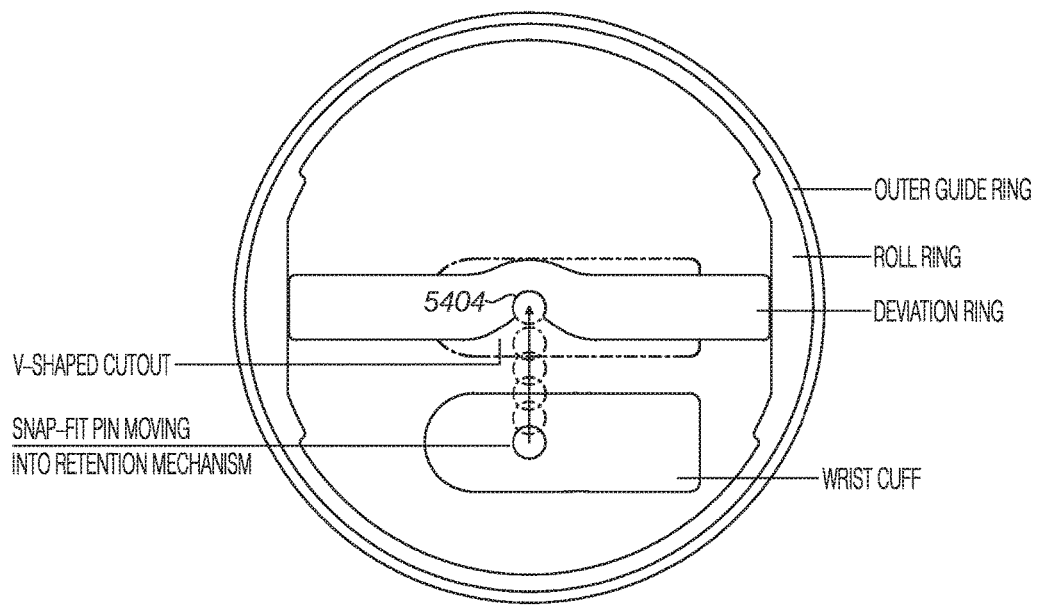
FIG. 45 schematically illustrates a method for one mechanism used to retain the cuff within the deviation ring which may be found on one embodiment of the forearm attachment assembly which may be used with a minimal access tool.

Axis 2, defined by the two pins supported within the roll ring (referred to as sled pins in FIG. 43), is the axis of rotation for the subsequent ring known as the deviation ring. In use, when the forearm attachment assembly is attached to a user forearm, Axis 2 will approximately coincide with the user's deviation axis at their wrist joint (shown in FIGS. 42 and 43). The deviation ring is a rigid body which is free to rotate about Axis 2 defined by the sled pins. Appropriate fits exist between the sled pins and the receiving holes within the deviation ring as well as between the sled pins and the roll ring, such that the deviation ring is free to rotate, with respect to the roll ring, about Axis 2 established by the sled pins. FIG. 44 demonstrates the locations within each of the rings that the sled pins are constrained and thereby establishing an axis of rotation (Axis 2). The deviation ring contains two slightly greater than semi-circular cutouts 5404 which define an axis orthogonal to the axis defined by the sled pins as shown in FIG. 45. The cutouts 5404 on the deviation ring demonstrate one method for quick installation and removal of the subsequent cuff from the deviation ring. The deviation ring can be manufactured from a variety of plastic materials. The slightly greater than semi-circular geometry 5404 and elastic properties of the variety of plastic materials enable a snap-fit mechanism between snap-fit pins of the cuff (referred to as Snap-Fit Pins in FIG. 45, 46) and the receiving holes on the deviation ring, which provides adequate retention with low frictional resistance to rotation. The snap-fit pin design of the cuff may include pressed pins or integrated cylindrical bodies which extend from the cuff to define Axis 1. After the snap-fit pins have snapped into the receiving features on the deviation ring, the interface serves as a rotational joint about Axis 1 (See FIGS. 44 and 46). Adequate retention of the corresponding pins within this mechanism is necessary as this forearm attachment assembly supports the overall weight of any device or instrument attached to the common ground/tool frame/outer ring and overcomes resistances between the tool frame/outer ring and wrist cuff attached to the user forearm. Each semi-circular cutout 5404 can be preceded by a V-shaped cutout which acts as a guide ramp for the corresponding snap-fit pins as the user aligns the pins and secures the subsequent cuff into the deviation ring. The retention structure described herein is only one example for retention. The retention structure includes but is not limited to a ball-in-track, spring-pin/thru hole, clasp style, snap-fit style, axially aligned pairs of magnets, or other arrangements of magnets, or any other structure which may offer only 1 rotational DoF and potentially 1 translational DoF along the axis of rotation while constraining all other DoF. The retention structure may take many other forms without deviating from the scope of the disclosure.

Figure 46:
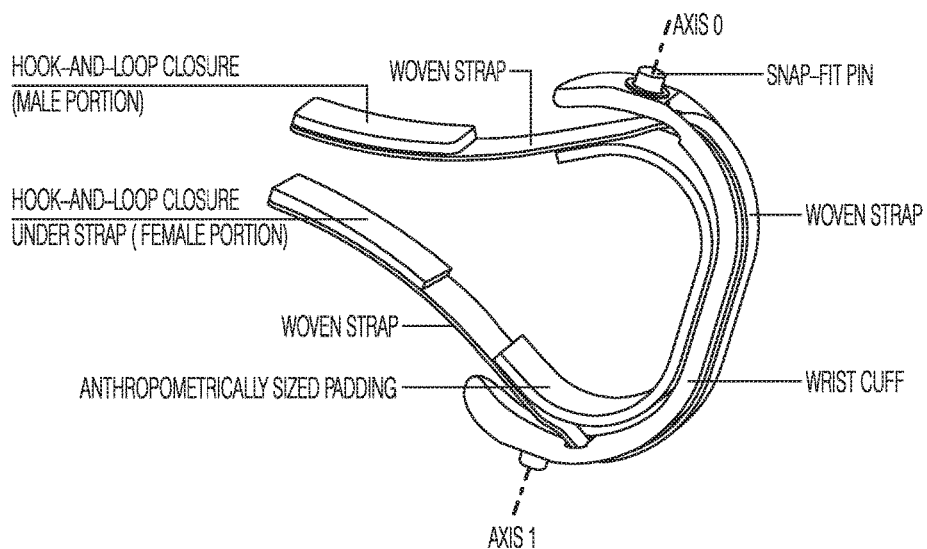
FIG. 46 illustrates a perspective view of one embodiment of the cuff and the various components that comprise the fitted strap for affixing the cuff to the user's forearm during use with a minimal access tool. In this example, the cuff is formed as a part of the gimbal and includes a fitted strap for affixing the cuff to the user's forearm during use with a minimal access tool.

Axis 1 defined by the two snap-fit pins which snap into the deviation ring, is the axis of rotation for the subsequent ring known as the wrist cuff. In use, when the forearm attachment assembly is attached to a user forearm, Axis 1 will approximately coincide with the user's flexion/extension axis at their wrist joint (as shown in FIGS. 42 and 43). The wrist cuff is a rigid body which is free to rotate, with respect to the deviation ring, about Axis 1 defined by two pins protruding from opposite ends of its curvature when they are constrained to their corresponding cutouts on the deviation ring. The specific geometry of both the wrist cuff and the deviation ring allows the user to insert their hand through the deviation ring and install the wrist cuff into the retention mechanism thereby constraining the user's wrist to the intersection point of the 3 axes of the forearm attachment assembly. The intent of the wrist cuff is to interface with the user's wrist as comfortably and securely as possible. These requirements can be met by a woven strap which is adhered to the outer surface of the cuff and continues through two channels to the inside of the wrist cuff (See FIG. 46). The woven strap terminates at a specific length on each end that it may be secured without excess for any wrist size by a hook-and-loop (Velcro) closure mechanism by overlapping the male and female portion of the hook-and-loop respectively. The woven strap is wrapped about the user's forearm as previously defined, under slight tension to provide a secure fit. Secure fit for each user can be determined by selecting the appropriate sized strap which includes a padding. The padding includes but is not limited to three sizes, small, medium, and large based on anthropometric data which measured wrist widths and breadth. The padding not only acts as a cushion for the user's wrist, its primary function is to act as a shim and align various wrist sizes to the center of the cuff ultimately keeping the center axes of the user's wrist, forearm, and hand coincident with the intersection of the wrist attachment apparatus' axes. The woven strap with hook-and-loop closure and the padding described herein is just one example for affixing the user's forearm to the cuff. There are many attachment options for affixing the user's forearm to the cuff including, but not being limited to, any combination of a woven strap, molded silicone band, metal link band or elastic strap with any clasp, prong, press-fit, or snap-fit type mechanism, ratcheting mechanism, etc. which may accommodate a variety of wrist sizes while providing adequate tethering to the wrist. See FIG. 46, showing a cuff including an integrated securement (snaps).

As mentioned above, the pins coupling the gimbals described above to the frame and/or to other coupling joints (e.g., other gimbals) may permit removal of the coupling joint(s) e.g., gimbals, from the tool, so that, for example, a user may put the cuff over the hand and onto the wrist or forearm, so that it can be attached thereto. Once attached, it can be inserted into to tool, for example, snapping into the frame or other other coupling joint(s). FIGS. 53A-53D illustrate another example of coupling joint forming a cuff (e.g. a gimbal with integral cuff) that can be releasably attached/detached from a tool (e.g., from an outer gimbal). In this example, a rigid cuff is formed onto a C-shaped gimbal body with a pair of spring-loaded pins 5302, 5302' along the rotational axis. This gimbal with a cuff can be securely placed on the user's forearm. This can be followed by inserting the cuff (now seated on the forearm) along the forearm axis into a ramp feature 5306 on the outer gimbal such that both the spring loaded pins get pressed by running on the ramp feature. As the cuff translates further along the forearm axis, the pins that were compressed by the reaction force from the inner gimbal come back to their nominal position secures the cuff such that the axis passing through the center of both the pins (rotational axis on cuff) coincide with the axis passing through the center of both the slot/holes on the outer gimbal (rotational axis on inner gimbal) to form the common rotational axis between the cuff and outer gimbal. This provided proper securement of cuff with the outer gimbal and still maintains the rotational DOF about first rotational axis. To disengage cuff from outer gimbal, the user presses the pin by compressing the spring in it and then translating the cuff back along the same forearm axis.

Another alternative embodiment of an outer gimbal design might comprise a recessed inner track within which a roll ring is constrained to only one degree of rotation about the axis described above. Also referring to FIG. 44, we see a sequential arrangement of components from Outer Guide ring to the Wrist Cuff, which sequentially produces Axis 3, Axis 2, and Axis 1. However, one may envision a different sequence of components that will result in a different sequence of these three axes between Outer Ring and Wrist Cuff. For example the axis sequence could be Axis 3, Axis 1, Axis 2 or Axis 2, Axis 1, Axis 3, etc.

Figure 47:
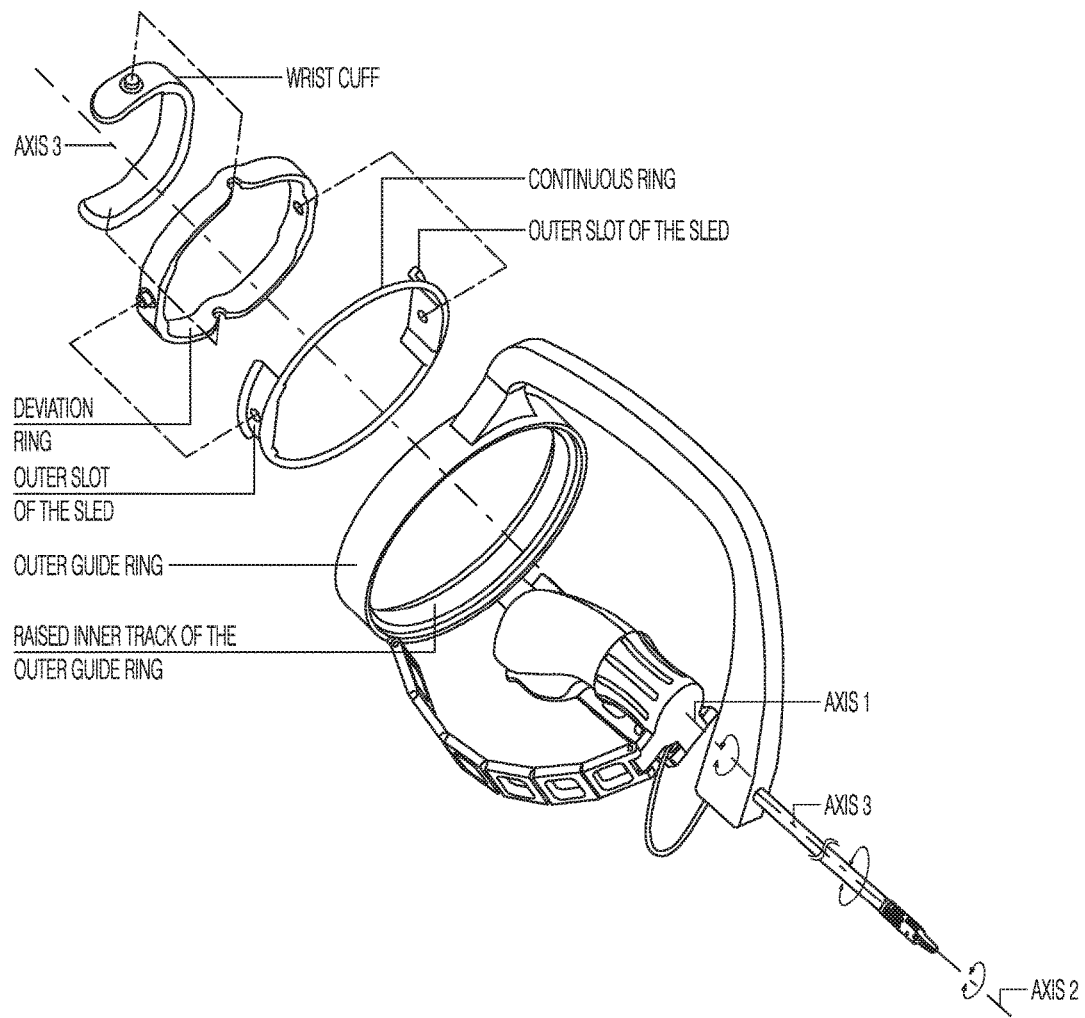
FIG. 47 illustrates an overall laparoscopic instrument with a particular embodiment of the forearm attach apparatus (exploded view) installed for use as a minimal access tool.

Now refer to FIG. 47, these figures show the forearm attachment assembly in conjunction with a surgical tool/instrument. In use, a surgeon will strap on the wrist cuff to his forearm. He will then insert his hand through the deviation ring (which is already assembled with the roll ring, which is already assembled with the outer ring), and will snap the snap-fit pins of the wrist cuff into the corresponding receiving features in the deviation ring. The outer ring is rigidly coupled/attached to the tool frame, which in turn is coupled/attached to the tool shaft. The surgeon's hand/palm holds the tool handle. Once the tool is interfaced with the user in this manner, the tool shaft axis can be oriented in any arbitrary direction with respect to the user's forearm axis (refer to FIGS. 17 and 18). Furthermore, as the surgeon holds the handle and rotates the handle about his forearm axis (1709 in FIG. 17) or hand axis (1707 in FIG. 17) using either a pronation/supination action of his forearm or twirl action of his fingers, this rotation is transmitted from the handle to tool frame/outer ring via the input joint (a VC mechanism in this case). This rotation of the tool frame about the tool axis is guided by the rotational sliding joint (about Axis 3) between the outer ring and roll ring. Thus, the tool axis and Axis 3 become coincident. The Axis 3 joint provided by the forearm attachment assembly allows a smooth, defined, and low-friction/resistance roll rotation of the entire tool frame about the user's hand and forearm. FIGS. 52A-52G further illustrate many variations of the forearm attachment assembly with a surgical tool/instrument, e.g., a surgical tool including an end effector, a serpentine output joint, and an input joint that is a parallel kinematic, 2 DOF input joint.

An additional aspect of this invention involves appropriate weight distribution of the overall tool and in particular the frame and outer ring, such that the center of gravity (CG) lies on or close to the tool axis (i.e. Axis 3). This ensures that as the surgeon rolls the entire tool about Axis 3 driving this roll by his hand, he feels as little resistance to roll due to gravity as possible. If indeed the CG was off-axis, then during certain stretches/portions of the roll, the surgeon would be trying to lift the weight of the overall tool against gravity, while during other stretches/portions the tool would fall under its own weight as it rolls. Also when the CG traverse in the vertical up condition, there would be an over the top falling feeling (which can be distracting to the surgeon). Therefore an important design goal and performance metric for the overall tool is that we design the overall tool such that the weight is balanced, i.e. CG is at or close to tool axis i.e. Axis 3. This may dictate the design/size/shape/geometry of the outer ring and tool frame.

Another aspect of device level functionality enabled by the forearm mount apparatus is that it helps to isolate the wrist articulation motion (two rotations) and twirling motion of a surgeon from the forearm motions (three translations, plus forearm pronation/supination i.e. roll rotation). The former corresponds to finer and more delicate motion, while the latter correspond to power moves. Such separation of fine/delicate motions and coarse/power motions are of great help to the surgeon while performing complex procedures.

Figure 51:
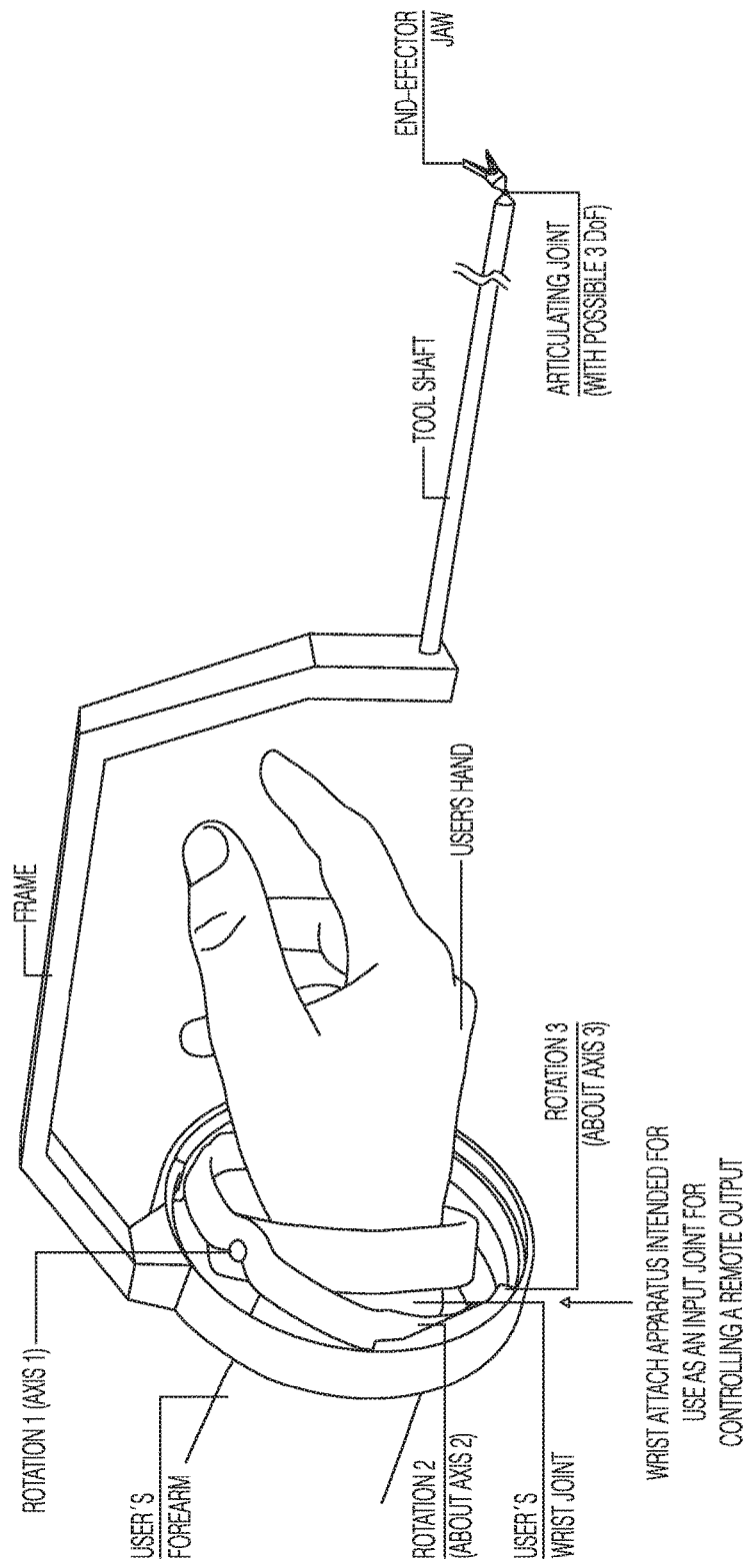
FIG. 51 illustrates the three-axis gimbal type arrangement may be used by a user for controlling a remote end-effector in remote access tool e.g. a surgical tool.
Figure 52A:
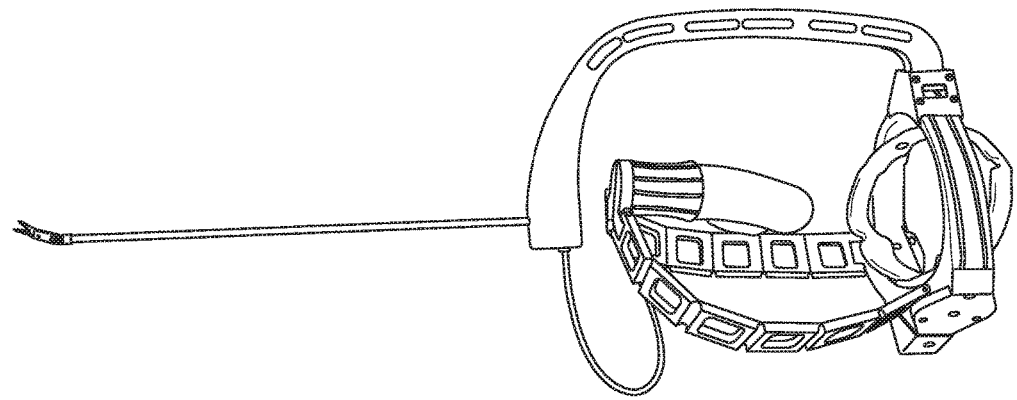
FIGS. 52A-52G illustrate an exemplary minimum access tool including a body (e.g., forearm) attachment assembly as described herein, having pitch, yaw and roll rotation, as described herein. This example includes a parallel kinematic input joint having two DoF.
Figure 52B:
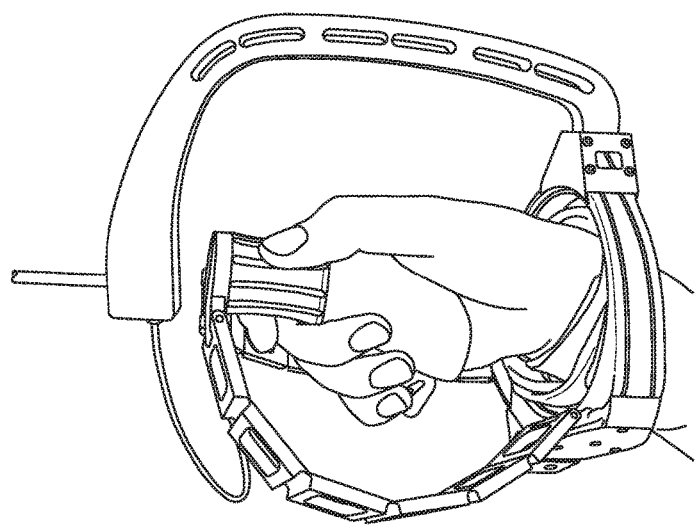
Figure 52C:
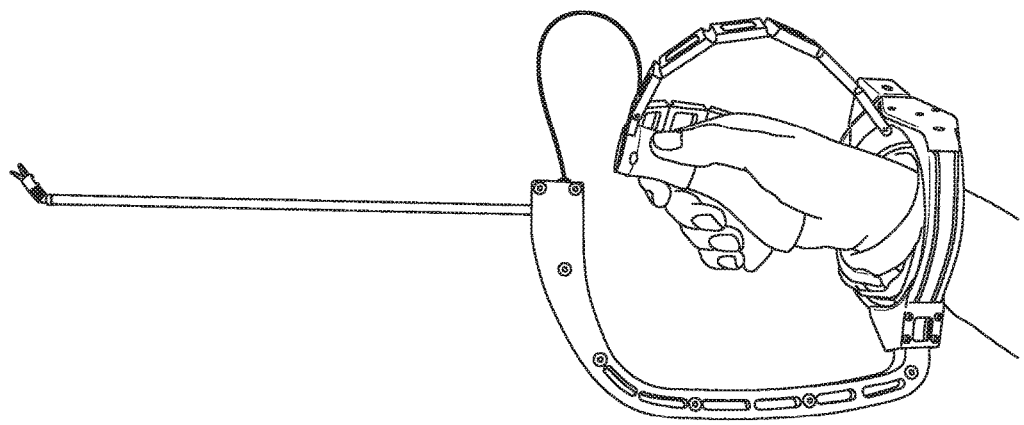
Figure 52D:
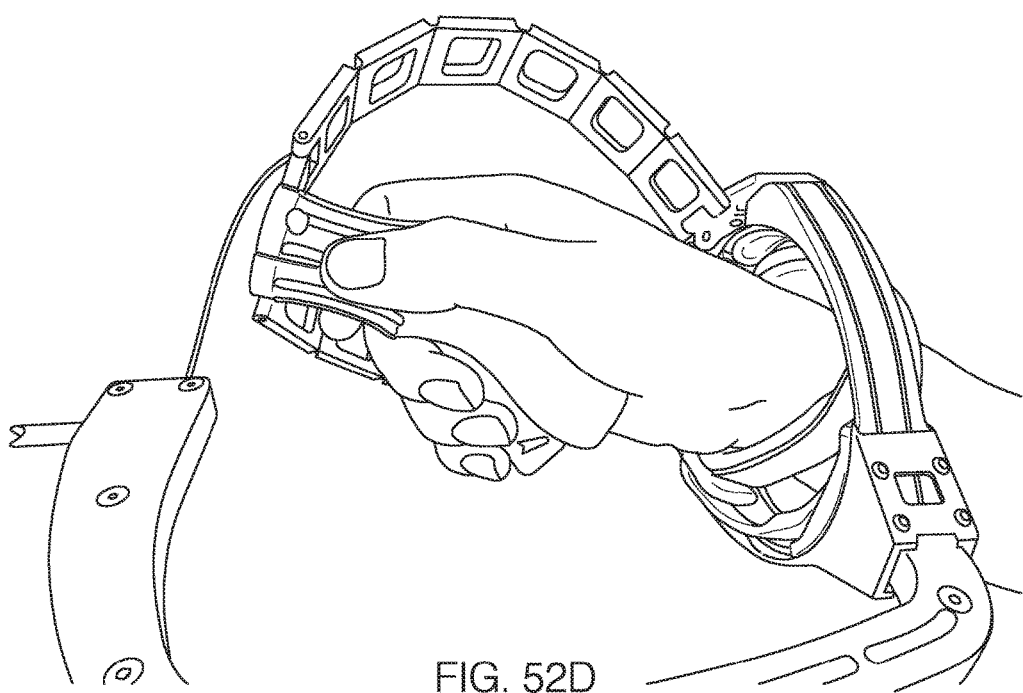
Figure 52E:
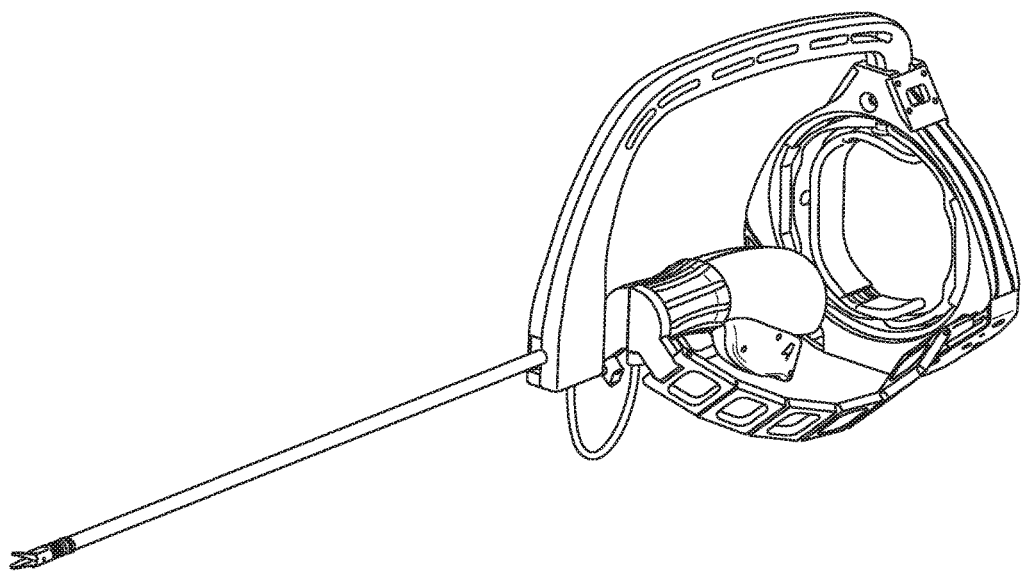
Figure 52F:
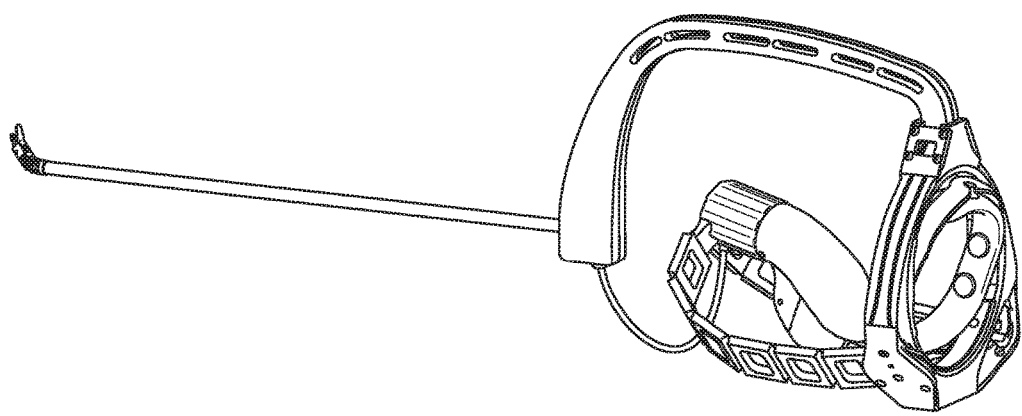
Figure 52G:
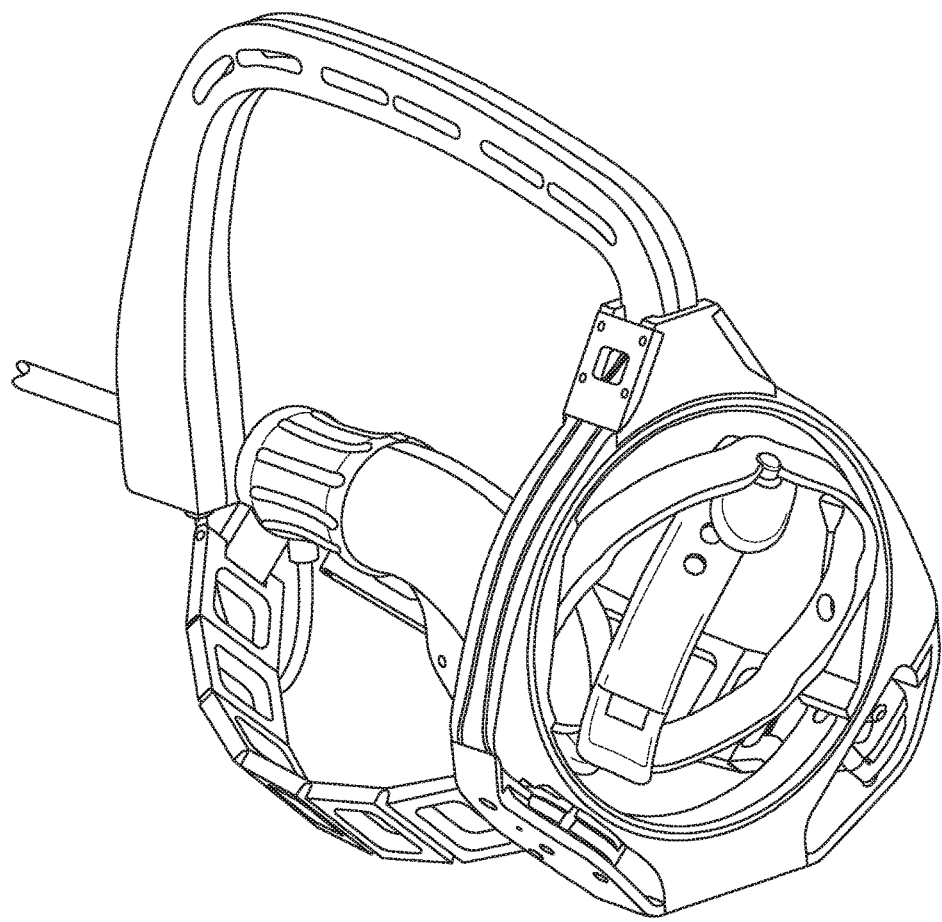
Figures 53A, 53B, 53C:
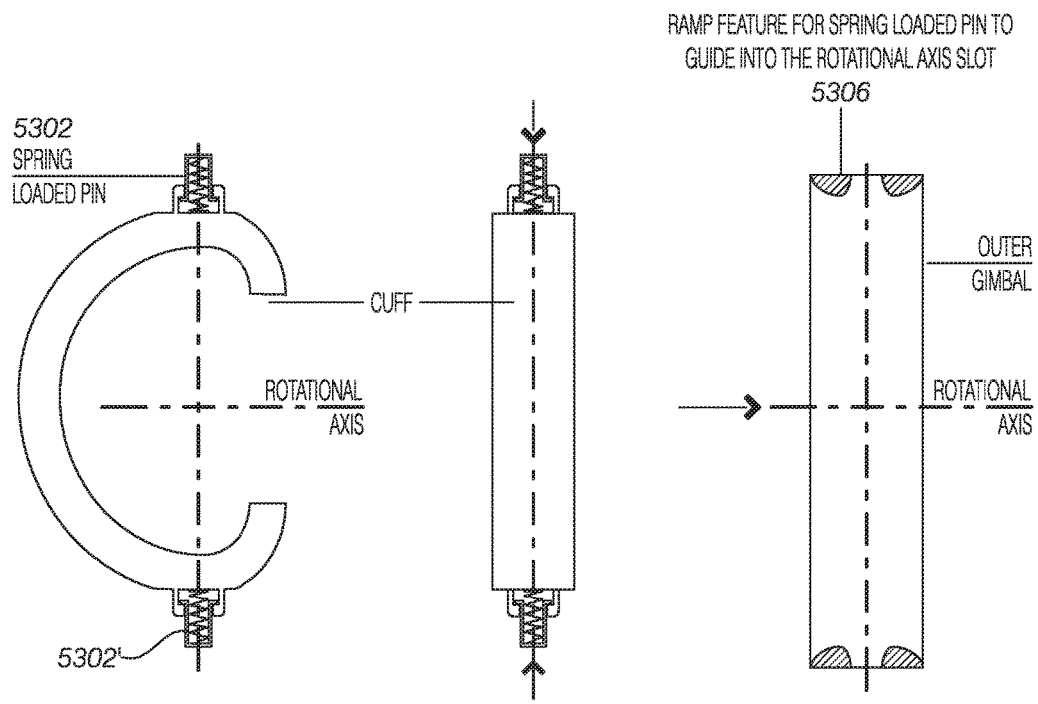
FIGS. 53A-53D illustrate another variation of a cuff that is integrated into a coupling joint (configured in this example as a gimbal) that is removably attachable/detachable from the tool (e.g., a minimal access tool).
Figure 53D:
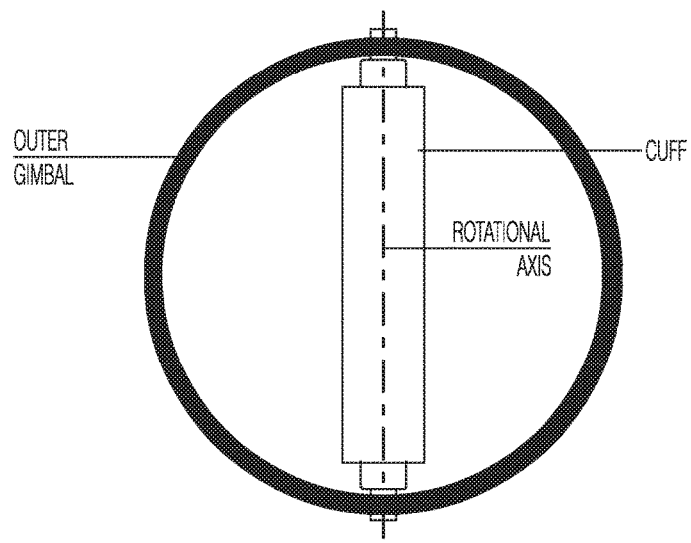

In yet another application/use (different from FIG. 47) of the forearm attach apparatus embodiment of FIGS. 42 and 43, the three-axis gimbal type arrangement may be used by a user for controlling a remote end-effector in remote access tool e.g. a surgical tool (See FIG. 51)

The wrist cuff can be attached to the forearm of the user, and therefore the frame has 3 rotational DoF with respect to the wrist and forearm of the user. User may articulate and rotate his forearm with respect to the frame to generate the three rotations about their respective axes in the forearm attachment joint. Some or all three of these rotations/DoF (about Axis 1, Axis 2, and Axis 3) of the apparatus may be captured mechanically or electronically and transmitted to corresponding rotations/DoF at a remote end-effector. See FIG. 51.

Note that in this case, the forearm attachment joint serves as the input joint of the remote access tool and there is no additional input joint between a tool handle held in the hand and the tool frame (as was the case in FIG. 47). Also, note that this is an example of a serial kinematic (S-K) input joint.

However, the key unique functionality of this arrangement of S-K input joint is that it leaves the hand free to hold any other device, while all the rotations/DoF are generated by action of the forearm. Also, the forearm has lower tremors compared to the handle and is capable of generating higher driving forces.

Even though in all embodiments described here, the cuff is attached to the forearm and thus, the cuff, the coupling joint, and the frame may be borne by the forearm, other embodiments in which the cuff is attached at the hand (i.e. at a location distal with respect to the wrist joint) or attached at the wrist joint of the user may also be used.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A minimal access tool that mounts to a user so that the tool may roll about the user's forearm, the tool comprising:
   a frame comprising an elongate tool shaft having a tool axis;
   a cuff having a passage therethrough that is configured to hold a wrist or forearm of the user;
   a first gimbal rotationally coupled between the frame and the cuff so that there is a first rotational degree of freedom between the frame and the cuff about a first axis;
   a bearing between the frame and the cuff and configured to slide or roll so that there is a roll rotational degree of freedom between the frame and the cuff about the tool axis;
   wherein, when the cuff is attached to the user's wrist or forearm, the tool axis and the first axis intersect within the passage through the cuff.

2. The tool of claim 1, wherein the first gimbal is rotatably coupled to the frame and the bearing is slideably coupled to the first gimbal.

3. The tool of claim 1, wherein the bearing is slideably coupled to the frame and the first gimbal is rotatably coupled to the bearing.

4. The tool of claim 1, further comprising a second gimbal rotationally coupled between the frame and the cuff so that there is a second rotational degree of freedom between the frame and the cuff about a second axis, wherein, when the cuff is attached to the user's wrist or forearm, the tool axis, the first axis and the second axis intersect at a point within the user's wrist or forearm.

5. The tool of claim 1, wherein the cuff is part of the first gimbal.

6. The tool of claim 1, wherein the cuff is configured to removably attach within the first gimbal.

7. The tool of claim 1, wherein the bearing is part of the first gimbal.

8. The tool of claim 1, wherein the bearing is configured to permit continuous roll rotation of the frame with respect to the user's wrist or forearm.

9. The tool of claim 1, wherein the bearing comprises a plain bearing, a bush bearing, or a rolling element bearing extending in a ring around the cuff.

10. The tool of claim 1, wherein wherein the cuff comprises a C-shaped member.

11. The tool of claim 1, further comprising a securement configured to hold the user's wrist or forearm in the cuff so that the cuff moves with the user's wrist or forearm.

12. The tool of claim 1, further comprising a securement configured to hold the user's wrist or forearm within the cuff so that the cuff moves with the user's arm or forearm, and further wherein the securement comprises at least one of: a strap, a snap, a belt, a latch and hook connector, a tie, or a clamp.

13. The tool of claim 1, further comprising a handle coupled to the frame through an input joint having at least one degree of freedom.

14. The tool of claim 1, further comprising a handle coupled to the frame through a parallel kinematic input joint having at least two degrees of freedom.

15. The tool of claim 1, further comprising a handle coupled to the frame through an input joint having at least two rotational degrees of freedom, wherein a parallel kinematic input joint constrains roll of the handle relative to the frame so that roll is transmitted from the handle to the frame.

16. The tool of claim 1, further comprising an end effector joint coupled to the tool shaft through an output joint.

17. The tool of claim 1, wherein the first gimbal is configured to removably attach to the tool.

18. A minimal access tool that mounts to a user so that the tool may roll about the user's forearm, the tool comprising:
   a frame comprising an elongate tool shaft having a tool axis;
   a cuff that is configured to attach to the user's wrist or forearm;
   a first gimbal rotationally coupled between the cuff and the frame so that there is a pitch rotational degree of freedom between the frame and the cuff about a first axis;
   a second gimbal rotationally coupled between the cuff and the frame so that there is a yaw rotational degree of freedom between the frame and the cuff about a second axis;
   a bearing between the cuff and the frame and configured to slide or roll so that there is a roll rotational degree of freedom between the frame and the cuff about the tool axis,
   wherein, when the cuff is attached to the user's wrist or forearm, the tool axis, the first axis and the second axis intersect at a point within the user's wrist or forearm; and
   a securement configured to hold the user's wrist or forearm in the cuff so that the user's hand extends through the first gimbal and the second gimbal and the cuff moves with the user's wrist or forearm.

19. The tool of claim 18, wherein the first gimbal, the second gimbal and the bearing are serially connected in any order between the cuff and the frame.

20. A method of operating a minimal access tool, wherein the minimal access tool includes a frame comprising an elongate tool shaft having a tool axis, the method comprising:
   securing a user's forearm or wrist within a cuff so that the user's wrist or forearm extends through a first gimbal and is retained in the cuff wherein there is a roll rotational degree of freedom about the tool axis between the cuff and the frame through a bearing that rolls or slides and wherein there is a second rotational degree of freedom between the cuff and the frame through the first gimbal;

changing either or both of an angle or a roll position of the user's wrist or forearm relative to the tool axis as the user moves the user's arm, by one or both of: rotating the first gimbal about a second rotational axis, and sliding the bearing to roll about the tool axis, wherein the second rotational axis and the tool axis intersect at a point of intersection that is within the user's wrist or forearm.

21. The method of claim 20, wherein securing the user's wrist or forearm comprises securing the user's forearm or wrist with a securement comprising one or more of: a strap, a snap, a belt, a latch and hook connector, a tie, or a clamp.

22. The method of claim 20, further comprising coupling a distal region of the elongate tool shaft to a mount.

23. The method of claim 20, further comprising coupling a distal region of the elongate tool shaft to a mount, wherein changing either or both the angle or roll position of the user's wrist or forearm relative to the tool axis comprises leaving the distal end of region of the elongate member coupled to the mount as either or both of the angle and roll position of the user's wrist or forearm are changed relative to the elongate tool shaft.

24. The method of claim 20, further comprising manipulating a handle coupled to the tool shaft through an input joint to articulate an end effector coupled to a distal end of the elongate member of the tool frame via an output joint.

25. The method of claim 20, further comprising manipulating a handle coupled to the tool frame in pitch, yaw, or pitch and yaw rotations, wherein the handle is coupled to the tool frame through a parallel kinematic input joint that transmits the pitch, yaw, or pitch and yaw rotations to corresponding rotations of an output joint at an end effector.

\* \* \* \* \*

UNITED STATES PATENT AND TRADEMARK OFFICE
CERTIFICATE OF CORRECTION

PATENT NO. : 9,629,689 B2
APPLICATION NO. : 15/130915
DATED : April 25, 2017
INVENTOR(S) : Gregory Brian Bowles et al.

It is certified that error appears in the above-identified patent and that said Letters Patent is hereby corrected as shown below:

In the Drawings

Sheet 19, FIG. 40B, delete "(PRIOR ART)"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*